United States Patent
Hoves et al.

(10) Patent No.: US 9,475,775 B2
(45) Date of Patent: Oct. 25, 2016

(54) BENZAZEPINE DICARBOXAMIDE COMPOUNDS

(71) Applicant: Hoffmann-La Roche Inc., Little Falls, NJ (US)

(72) Inventors: Sabine Hoves, Habach (DE); Lisha Wang, Riehen (CH); Hongying Yun, Shanghai (CN); Weixing Zhang, Shanghai (CN); Wei Zhu, Shanghai (CN)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 15/061,105

(22) Filed: Mar. 4, 2016

(65) Prior Publication Data

US 2016/0257653 A1    Sep. 8, 2016

(30) Foreign Application Priority Data

Mar. 6, 2015  (CN) ................ PCT/CN2015/073775
Dec. 4, 2015  (CN) ................ PCT/CN2015/096404

(51) Int. Cl.
| | |
|---|---|
| *C07D 233/16* | (2006.01) |
| *C07D 401/12* | (2006.01) |
| *C07D 403/12* | (2006.01) |
| *C07D 417/12* | (2006.01) |
| *C07D 413/12* | (2006.01) |
| *A61K 31/55* | (2006.01) |
| *C07D 223/16* | (2006.01) |

(52) U.S. Cl.
CPC ........... *C07D 223/16* (2013.01); *C07D 401/12* (2013.01); *C07D 403/12* (2013.01); *C07D 413/12* (2013.01); *C07D 417/12* (2013.01)

(58) Field of Classification Search
None
See application file for complete search history.

(56) References Cited

U.S. PATENT DOCUMENTS

| | | | |
|---|---|---|---|
| 2003/0187016 A1 | 10/2003 | Crooks et al. | |
| 2013/0202629 A1* | 8/2013 | Carson | A61K 31/52 424/184.1 |

FOREIGN PATENT DOCUMENTS

| | | |
|---|---|---|
| WO | 92/15582 A1 | 9/1992 |
| WO | 2005/076783 A2 | 8/2005 |
| WO | 2007/024612 A2 | 3/2007 |
| WO | 2009/111337 A1 | 9/2009 |
| WO | 2010/054215 A1 | 5/2010 |
| WO | 2010/093436 A2 | 8/2010 |
| WO | 2011/017611 A1 | 2/2011 |
| WO | 2011/022509 A2 | 2/2011 |
| WO | 2011/068233 A1 | 6/2011 |
| WO | 2011/139348 A2 | 11/2011 |
| WO | 2012/045090 A2 | 4/2012 |
| WO | 2012/066336 A1 | 5/2012 |
| WO | 2012/167081 A1 | 12/2012 |
| WO | 2013/033345 A1 | 3/2013 |
| WO | 2013/067597 A1 | 5/2013 |
| WO | 2013/166110 A1 | 11/2013 |

OTHER PUBLICATIONS

Hennessy et al., "Targeting Toll-Like Receptors: Emerging Therapeutics?" Nature Reviews: Drug Discovery 9:292-307 (Apr. 2010).
Holldack, "Toll-Like Receptors as Therapeutic Targets for Cancer" Drug Discovery Today 19(4):379-382 (Apr. 2014).
International Search Report for PCT/EP2015/058465, dated May 26, 2015.
ISR for PCT/EP2016/054487.
Kowai et al., "The Role of Pattern-Recognition Receptors in Innate Immunity: Update on Toll-Like Receptors" Nature Immunology 11(5):373-384 (May 2010).
Kawai et al., "Toll-Like Receptors and Their Crosstalk with Other Innate Receptors in Infection and Immunity" Immunity 34:637-650 (May 27, 2011).
Uematsu et al., "Toll-Like Receptors and Type I Interferons" Journal of Biological Chemistry 282(21):15319-15323 (May 25, 2007).
Written Opinion for PCT/EP2015/058465.
Written Opinion for PCT/EP2016054487.

* cited by examiner

*Primary Examiner* — Yevegeny Valenrod

(57) ABSTRACT

This invention relates to novel benzazepine dicarboxamide compounds of the formula

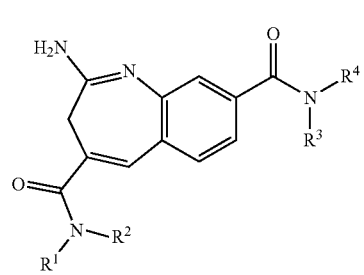

wherein $R^1$ to $R^4$ are as defined in the description and in the claims, as well as pharmaceutically acceptable salts thereof. These compounds are TLR agonists and may therefore be useful as medicaments for the treatment of diseases such as cancer, autoimmune diseases, inflammation, sepsis, allergy, asthma, graft rejection, graft-versus-host disease, immunodeficiencies, and infectious diseases.

19 Claims, No Drawings

BENZAZEPINE DICARBOXAMIDE COMPOUNDS

FIELD OF THE INVENTION

The present invention relates to novel benzazepine dicarboxamide compounds having pharmaceutical activity, their manufacture, pharmaceutical compositions containing them and their potential use as medicaments.

In particular, the present invention relates to compounds of the formula

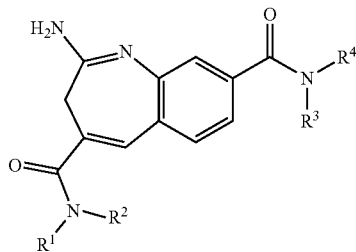

wherein $R^1$ to $R^4$ are as described below, or to pharmaceutically acceptable salts thereof.

The compounds are TLR agonists. More particularly, the compounds are TLR8 agonists and may be useful for the treatment and prevention (e.g. vaccination) of cancer, autoimmune diseases, inflammation, sepsis, allergy, asthma, graft rejection, graft-versus-host disease, immunodeficiencies, and infectious diseases.

Toll-like receptors (TLRs) are a family of membrane-spanning receptors that are expressed on cells of the immune system like dendritic cells, macrophages, monocytes, T cells, B cells, NK cells and mast cells but also on a variety of non-immune cells such as endothelial cells, epithelial cells and even tumor cells (Kawai et al., Immunity, 2011, 34, 637-650, Kawai et al., Nat. Immunol., 2010, 11, 373-384). TLRs that recognize bacterial and fungal components are expressed on the cell surface (i.e. TLR1, 2, 4, 5 and 6), while others that recognize viral or microbial nucleic acids like TLR3, 7, 8 and 9 are localized to the endolysosomal/phagosomal compartment (Henessy et al. Nat. Rev. Drug Discovery 2010, 9, 293-307) and predominantly found to be expressed by cells of the myeloid lineage. TLR ligantion leads to activation of NF-κB and IRF-dependent pathways with the specific activation sequence and response with respect to the specific TLR and cell type. While TLR7 is mainly expressed in all dendritic cells subtypes (DC and here highly in pDC, plasmacytoid DC) and can be induced in B cells upon IFNα stimulation (Bekeredjian-Ding et al. J. Immunology 2005, 174:4043-4050), TLR8 expression is rather restricted to monocytes, macrophages and myeloid DC. TLR8 signaling via MyD88 can be activated by bacterial single stranded RNA, small molecule agonists and lately discovered microRNAs (Chen et al. RNA 2013, 19:737-739). The activation of TLR8 results in the production of various pro-inflammatory cytokines such as IL-6, IL-12 and TNF-α as well as enhanced expression of co-stimulatory molecules, such as CD80, CD86, and chemokine receptors (Cros et al. Immunity 2010, 33:375-386). In addition, TLR8 activation can induce type I interferon (IFNβ) in primary human monocytes (Pang et al. BMC Immunology 2011, 12:55).

Small molecule agonists for both the TLR7 and TLR8 receptor as well as analogs modified for use as vaccine adjuvants or conjugates have been identified in many patents (i.e. WO1992015582, WO2007024612, WO2009111337, WO2010093436, WO2011017611, WO2011068233, WO2011139348, WO2012066336, WO2012167081, WO2013033345, WO2013166110, and US2013202629). Clinical experience has been obtained mainly for TLR7 agonists, but only very few clinical studies focused on using highly specific TLR8 agonists. To date, the only FDA (U.S. Food and Drug Administration)-approved small molecule drug is the TLR7 agonist imiquimod (ALDARA™) as a topical agent for the treatment of genital warts, superficial basal cell carcinoma and actinic keratosis. Systemic application however of the early TLR7 agonists like resiquimod has been abandoned due to intolerable cardiotoxicity observed upon global chemokine stimulation at therapeutic levels (Holldack, Drug Discovery Today, 2013, 1-4). Knowledge about TLR8 agonists is less advanced and mostly restricted to data with early mixed TLR7/8 agonists like resiquimod. For the resiquimod agonist, however, the stimulatory capacity of the TLR7 is superior compared to the activation of the TLR8, so that most of the effects of resiquimod are dominated by the effect of TLR7 activity. More recently, TLR8 specific compounds like VTX-2337 have been described by VentiRX Pharmaceuticals (i.e. WO 2007024612), allowing for the first time to analyse the specific role of TLR8 without activation of TLR7 at the same time. At present there is still a need for small molecule TLR8 agonists, specifically those with improved potency or selectivity.

The present invention is directed to benzazepines with improved cellular potency over known TLR8 agonists of this type for use in the treatment of cancer, preferably solid tumors and lymphomas, and for other uses including the treatment of certain skin conditions or diseases, such as atopic dermatitis, the treatment of infectious diseases, preferably viral diseases, and for use as adjuvants in vaccines formulated for use in cancer therapy or by desensitizing of the receptors by continuous stimulation in the treatment of autoimmune diseases.

Of note, these new compounds have improved cellular potency at TLR8 compared to known TLR8 agonists such as VTX-2337. In addition these compounds are highly specific towards TLR8 and possess only low or even no activity towards TLR7. Thus, they are expected to possess advantageous properties compared to combined TLR7/8 agonists due to the more restricted expression pattern of TLR8 resulting in less servere side effects when administered systemically.

SUMMARY OF THE INVENTION

The present invention relates to benzazepine-4-carboxamide compounds of the formula

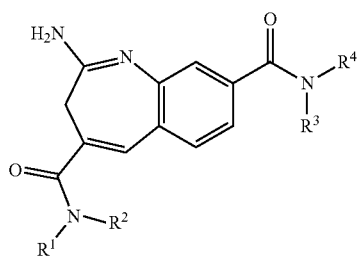

wherein $R^1$ is $C_{3-7}$-alkyl or $C_{3-7}$-cycloalkyl, $R^2$ is selected from the group consisting of $C_{1-7}$-alkyl, hydroxy-$C_{1-7}$-alkyl, $C_{2-7}$-alkenyl, $C_{3-7}$-alkinyl, amino-$C_{1-7}$-alkoxy-$C_{1-7}$-alkyl, amino-$C_{1-7}$-alkoxy-$C_{1-7}$-alkoxy-$C_{1-7}$-alkyl, halogen-$C_{1-7}$-alkyl, $C_{3-7}$-cycloalkyl-$C_{1-7}$-alkyl and phenyl-$C_{1-7}$-alkyl, wherein phenyl is unsubstituted or substituted by amino-$C_{1-7}$-alkyl;

$R^3$ is hydrogen;

$R^4$ is selected from the group consisting of phenyl, said phenyl being unsubstituted or substituted by one or two groups selected from the group consisting of $C_{1-7}$-alkyl, halogen, halogen-$C_{1-7}$-alkyl, $C_{1-7}$-alkoxy, hydroxy-$C_{1-7}$-alkyl, amino-$C_{1-7}$-alkyl, $C_{1-7}$-alkyl-amino-$C_{1-7}$-alkyl, di-$C_{1-7}$-alkyl-amino-$C_{1-7}$-alkyl, amino-$C_{2-7}$-alkenyl, $C_{1-7}$-alkyl-amino-$C_{2-7}$-alkenyl, di-$C_{1-7}$-alkyl-amino-$C_{2-7}$-alkenyl, amino-$C_{2-7}$-alkinyl, $C_{1-7}$-alkyl-amino-$C_{2-7}$-alkinyl, benzyloxycarbonylamino-$C_{1-7}$-alkyl, amino-$C_{1-7}$-alkoxy, amino-$C_{1-7}$-alkoxy-$C_{1-7}$-alkoxy, amino-$C_{1-7}$-alkoxy-$C_{1-7}$-alkyl, amino-$C_{1-7}$-alkoxy-$C_{1-7}$-alkoxy-$C_{1-7}$-alkyl, $C_{1-7}$-alkylsulfonyl heterocyclylcarbonyl and phenyl-$C_{1-7}$-alkyl, wherein phenyl is unsubstituted or substituted by $C_{1-7}$-alkoxy or amino-$C_{1-7}$-alkyl, or heteroaryl, said heteroaryl being a 5- or 6-membered aromatic ring containing one, two or three heteroatoms selected from N, O or S and being unsubstituted or substituted by one or two groups selected from the group consisting of $C_{1-7}$-alkyl, halogen, halogen-$C_{1-7}$-alkyl, $C_{1-7}$-alkoxy, hydroxy-$C_{1-7}$-alkyl, amino-$C_{1-7}$-alkyl, $C_{1-7}$-alkyl-amino-$C_{1-7}$-alkyl, di-C alkyl-amino-$C_{1-7}$-alkyl, amino-$C_{2-7}$-alkenyl, $C_{1-7}$-alkyl-amino-$C_{2-7}$-alkenyl, di-$C_{1-7}$-alkyl-amino-$C_{2-7}$-alkenyl, amino-$C_{2-7}$-alkinyl, $C_{1-7}$-alkyl-amino-$C_{2-7}$-alkinyl, di-$C_{1-7}$-alkyl-amino-$C_{2-7}$-alkinyl, benzyloxycarbonylamino-$C_{1-7}$-alkyl, amino-$C_{1-7}$-alkoxy, amino-$C_{1-7}$-alkoxy-$C_{1-7}$-alkoxy, amino-$C_{1-7}$-alkoxy-$C_{1-7}$-alkyl, amino-$C_{1-7}$-alkoxy-$C_{1-7}$-alkoxy-$C_{1-7}$-alkyl, $C_{1-7}$-alkylsulfonyl heterocyclylcarbonyl and phenyl-$C_{1-7}$-alkyl, wherein phenyl is unsubstituted or substituted by $C_{1-7}$-alkoxy or amino-$C_{1-7}$-alkyl, or pharmaceutically acceptable salts thereof.

The invention is also concerned with processes for the manufacture of compounds of formula I.

The invention also relates to pharmaceutical compositions comprising a compound of formula I as described above and a pharmaceutically acceptable carrier and/or adjuvant.

A further aspect of the invention is the use of compounds of formula I as therapeutic active substances for the treatment of diseases that can be mediated with TLR agonists, in particular TLR8 agonists. The invention thus relates to a method for the treatment of a disease that can be mediated with TLR agonists such as for example cancer and autoimmune or infectious diseases.

DETAILED DESCRIPTION OF THE INVENTION

Unless otherwise defined, all technical and scientific terms used herein have the same meaning as commonly understood by one of ordinary skill in the art to which this invention belongs. Furthermore, the following definitions are set forth to illustrate and define the meaning and scope of the various terms used to describe the invention.

The nomenclature used in this application is based on IUPAC systematic nomenclature, unless indicated otherwise.

The term "compound(s) of this invention" and "compound(s) of the present invention" refers to compounds of formula I and solvates or salts thereof (e.g., pharmaceutically acceptable salts).

The term "substituent" denotes an atom or a group of atoms replacing a hydrogen atom on the parent molecule.

The term "halogen" refers to fluoro, chloro, bromo and iodo, with fluoro, chloro and bromo being of particular interest. More particularly, halogen refers to fluoro.

The term "alkyl", alone or in combination with other groups, refers to a branched or straight-chain monovalent saturated aliphatic hydrocarbon radical of one to twenty carbon atoms, particularly one to sixteen carbon atoms, more particularly one to ten carbon atoms. More particularly, the term "alkyl" also embraces lower alkyl groups as described below.

The term "lower alkyl" or "$C_{1-7}$-alkyl", alone or in combination, signifies a straight-chain or branched-chain alkyl group with 1 to 7 carbon atoms, in particular a straight or branched-chain alkyl group with 1 to 6 carbon atoms and more particularly a straight or branched-chain alkyl group with 1 to 4 carbon atoms. Examples of straight-chain and branched $C_{1-7}$ alkyl groups are methyl, ethyl, propyl, isopropyl, butyl, isobutyl, tert-butyl, the isomeric pentyls, the isomeric hexyls and the isomeric heptyls, in particular methyl and ethyl. The term "$C_{2-7}$-alkyl" refers to a straight-chain or branched-chain alkyl group with 2 to 7 carbon atoms as defined above, however the methyl or methylene group is excluded.

The term "lower alkenyl" or "$C_{2-7}$-alkenyl" signifies a straight-chain or branched chain hydrocarbon residue comprising an olefinic bond and 2 to 7, preferably 3 to 6, particularly preferred 3 to 4 carbon atoms. Examples of alkenyl groups are ethenyl, 1-propenyl, 2-propenyl, isopropenyl, 1-butenyl, 2-butenyl, 3-butenyl and isobutenyl, in particular 2-propenyl (allyl).

The term "lower alkinyl" or "$C_{2-7}$-alkinyl" signifies a straight-chain or branched chain hydrocarbon residue comprising a triple bond and 2 to 7 carbon atoms. Examples of lower alkinyl groups are ethinyl and 1-propinyl (—C≡C—CH$_3$).

The term "cycloalkyl" or "$C_{3-7}$-cycloalkyl" denotes a saturated carbocyclic group containing from 3 to 7 carbon atoms, such as cyclopropyl, cyclobutyl, cyclopentyl, cyclohexyl or cycloheptyl, more particularly cyclopropyl.

The term "lower cycloalkylalkyl" or "$C_{3-7}$-cycloalkyl-$C_{1-7}$-alkyl" refers to lower alkyl groups as defined above wherein at least one of the hydrogen atoms of the lower alkyl group is replaced by a cycloalkyl group. Among the lower cycloalkylalkyl groups of particular interest is cyclopropylmethyl.

The term "lower alkoxy" or "$C_{1-7}$-alkoxy" refers to the group R'—O—, wherein R' is lower alkyl and the term "lower alkyl" has the previously given significance. Examples of lower alkoxy groups are methoxy, ethoxy, n-propoxy, isopropoxy, n-butoxy, isobutoxy, sec.-butoxy and tert-butoxy, in particular methoxy.

The term "lower alkoxyalkyl" or "$C_{1-7}$-alkoxy-$C_{1-7}$-alkyl" refers to lower alkyl groups as defined above wherein at least one of the hydrogen atoms of the lower alkyl group is replaced by a lower alkoxy group. Among the lower alkoxyalkyl groups of particular interest are methoxymethyl, 2-methoxyethyl and 2-ethoxyethyl, with 2-ethoxyethyl being of most particular interest.

The term hydroxy or hydroxyl means the group —OH.

The term "lower hydroxyalkyl" or "hydroxy-$C_{1-7}$-alkyl" refers to lower alkyl groups as defined above wherein at least one of the hydrogen atoms of the lower alkyl group is replaced by a hydroxy group. Among the particular interesting lower hydroxyalkyl groups are hydroxymethyl or hydroxyethyl.

The term "lower halogenalkyl" or "halogen-$C_{1-7}$-alkyl" refers to lower alkyl groups as defined above wherein at least one of the hydrogen atoms of the lower alkyl group is replaced by a halogen atom, particularly fluoro or chloro, most particularly fluoro. Among the lower halogenalkyl groups of particular interest are trifluoromethyl, difluoromethyl, trifluoroethyl, 2,2-difluoroethyl, fluoromethyl and chloromethyl, with trifluoromethyl being of more particular interest.

The term "heterocyclylcarbonyl" means the group —C(O)—Het, wherein Het is a heterocyclyl group as defined hereinafter. A heterocyclylcarbonyl group of particular interest is pyrrolidin-1-ylcarbonyl.

"Amino" refers to the group —$NH_2$. The term "$C_{1-7}$-alkylamino" means a group —NHR, wherein R is lower alkyl and the term "lower alkyl" has the previously given significance. The term "di-$C_{1-7}$-alkylamino" means a group —NRR', wherein R and R' are lower alkyl groups as defined above.

The term "lower aminoalkyl" or "amino-$C_{1-7}$-alkyl" refers to lower alkyl groups as defined above wherein at least one of the hydrogen atoms of the lower alkyl group is replaced by an amino group. Among the particular interesting lower aminoalkyl groups are aminomethyl or 2-aminoethyl.

The term "lower alkylaminoalkyl" or "$C_{1-7}$-alkylamino-$C_{1-7}$-alkyl" refers to lower alkyl groups as defined above wherein at least one of the hydrogen atoms of the lower alkyl group is replaced by an $C_{1-7}$-alkylamino group. Among the particular interesting lower alkylaminoalkyl groups are ethylaminomethyl or 2-ethylaminoethyl.

The term "lower dialkylaminoalkyl" or "di-$C_{1-7}$-alkylamino-$C_{1-7}$-alkyl" refers to lower alkyl groups as defined above wherein at least one of the hydrogen atoms of the lower alkyl group is replaced by an di-$C_{1-7}$-alkylamino group. Among the particular interesting lower alkylaminoalkyl groups are dimethylaminomethyl or dimethylaminoethyl.

The term "lower aminoalkenyl" or "amino-$C_{3-7}$-alkenyl" refers to lower alkenyl groups as defined above wherein at least one of the hydrogen atoms of the lower alkenyl group is replaced by an amino group. Among the particular interesting lower aminoalkenyl groups is 3-amino-1-propenyl.

The term "lower aminoalkinyl" or "amino-$C_{3-7}$-alkinyl" refers to lower alkinyl groups as defined above wherein at least one of the hydrogen atoms of the lower alkinyl group is replaced by an amino group. A lower aminoalkinyl group of particular interest is 3-amino-1-propinyl.

The term "lower aminoalkoxy" or "amino-$C_{1-7}$-alkoxy" refers to lower alkoxy groups as defined above wherein at least one of the hydrogen atoms of the lower alkoxy group is replaced by an amino group. Among the particular interesting lower aminoalkoxy groups are aminomethoxy or aminoethoxy.

The term "lower aminoalkoxyalkyl" or "amino-$C_{1-7}$-alkoxy-$C_{1-7}$-alkyl" refers to lower alkoxyalkyl groups as defined above wherein at least one of the hydrogen atoms of the lower alkoxy group is replaced by an amino group. Among the particular interesting lower aminoalkoxyalkyl groups are 2-aminoethoxymethyl or 2-aminoethoxyethyl.

The term "lower aminoalkoxyalkoxyalkyl" or "amino-$C_{1-7}$-alkoxy-$C_{1-7}$-alkoxy-$C_{1-7}$-alkyl" refers to lower alkoxyalkyl groups as defined above wherein at least one of the hydrogen atoms of the lower alkoxyalkyl group is replaced by a lower aminoalkoxy group. Among the particular interesting lower aminoalkoxyalkoxyalkyl groups are 2-aminoethoxy-ethoxymethyl or 2-aminoethoxy-ethoxyethyl.

The term "lower aminoalkoxyalkoxy" or "amino-$C_{1-7}$-alkoxy-$C_{1-7}$-alkoxy" refers to lower alkoxy groups as defined above wherein at least one of the hydrogen atoms of the lower alkoxy group is replaced by a lower aminoalkoxy group. Among the particular interesting lower aminoalkoxyalkoxy groups are 2-aminoethoxy-methoxy or 2-aminoethoxy-ethoxy.

The term "lower alkylamino-alkoxy-alkyl" or "$C_{1-7}$-alkylamino-$C_{1-7}$-alkoxy-$C_{1-7}$-alkyl" refers to lower alkoxyalkyl groups as defined above wherein at least one of the hydrogen atoms of the lower alkoxy group is replaced by an alkylamino group. Among the particular interesting lower alkylaminoalkoxyalkyl groups are 2-methylaminoethoxymethyl or 2-methylamino-ethoxyethyl.

The term "lower alkylsulfonyl" or "$C_{1-7}$-alkylsulfonyl" means the group —$S(O)_2$—R, wherein R is a lower alkyl group as defined above. A lower alkylsulfonyl group of particular interest is methylsulfonyl.

The term "benzyloxycarbonylamino-$C_{1-7}$-alkyl" refers to an amino-$C_{1-7}$-alkyl group as defined herein before, wherein one hydrogen atom of the amino group is substituted by a benzyloxycarbonyl or phenylmethyloxycarbonyl group.

The term "lower phenylalkyl" or "phenyl-$C_{1-7}$-alkyl" refers to lower alkyl groups as defined above wherein at least one of the hydrogen atoms of the lower alkyl group is replaced by a phenyl ring. Lower phenylalkyl groups of particular interest are phenylmethyl and 2-phenylethyl, with 2-phenylethyl being of particular interest.

The term "heteroaryl" in general refers to an aromatic 5- or 6-membered ring which comprises one, two, three or four atoms selected from nitrogen, oxygen and/or sulfur, or to bicyclic aromatic groups comprising from 5 to 12 ring atoms, in which one or both rings can contain one, two or three atoms selected from nitrogen, oxygen or sulfur. Examples of heteroaryl groups are furanyl, pyridyl, pyrazinyl, pyrimidinyl, pyridazinyl, thienyl, isoxazolyl, thiazolyl, isothiazolyl, thiadiazolyl, oxazolyl, imidazolyl, pyrazolyl, triazolyl, oxadiazolyl, oxatriazolyl, tetrazolyl, pentazolyl, or pyrrolyl, or bicyclic groups such as quinolinyl, isoquinolinyl, cinnolinyl, pyrazolo[1,5-a]pyridyl, imidazo[1,2-a]pyridyl, quinoxalinyl, benzothiazolyl, benzotriazolyl, indolyl, indazolyl, and 3,4-dihydro-2H-pyrido[3,2-b][1,4]oxazinyl. Heteroaryl groups of particular interest are furanyl, pyridyl, pyrazinyl, pyrimidinyl, pyridazinyl, thienyl, isoxazolyl, thiazolyl, isothiazolyl, thiadiazolyl, oxazolyl, imidazolyl, pyrazolyl, triazolyl, oxadiazolyl, oxatriazolyl, tetrazolyl, pentazolyl, or pyrrolyl. More particularly, heteroaryl groups are selected from the group consisting of imidazolyl, pyrazolyl, oxazolyl, thiazolyl, pyridyl, pyridazinyl and pyrimidinyl.

The term "heterocyclyl" refers to a saturated or partly unsaturated 3-, 4-, 5-, 6- or 7-membered ring which can comprise one, two or three heteroatoms selected from N, O and S. Examples of heterocyclyl rings include piperidinyl, piperazinyl, azetidinyl, azepinyl, pyrrolidinyl, pyrazolidinyl, imidazolinyl, imidazolidinyl, oxazolidinyl, isoxazolidinyl, morpholinyl, thiazolidinyl, isothiazolidinyl, oxiranyl, thiadiazolylidinyl, oxetanyl, dioxolanyl, dihydrofuranyl, tetrahydrofuranyl, dihydropyranyl, tetrahydropyranyl, and thiomorpholinyl. Of particular interest is the pyrrolidinyl group.

The term "pharmaceutically acceptable" denotes an attribute of a material which is useful in preparing a pharmaceutical composition that is generally safe, non-toxic, and neither biologically nor otherwise undesirable and is acceptable for veterinary as well as human pharmaceutical use.

Compounds of formula I can form pharmaceutically acceptable salts. The term "pharmaceutically acceptable salts" refers to those salts which retain the biological effectiveness and properties of the free bases or free acids, which are not biologically or otherwise undesirable. Pharmaceutically acceptable salts include both acid and base addition salts. The salts are for example acid addition salts of compounds of formula I with physiologically compatible mineral acids, such as hydrochloric acid, hydrobromic acid, nitric acid, carbonic acid, sulfuric acid, sulfurous acid or phosphoric acid; or with organic acids, such as methanesulfonic acid, ethanesulfonic acid, p-toluenesulfonic acid, formic acid, acetic acid, propionic acid, glycolic acid, pyruvic acid, oxylic acid, lactic acid, trifluoroacetic acid, citric acid, fumaric acid, maleic acid, malonic acid, tartaric acid, benzoic acid, cinnamic acid, mandelic acid, embonic acid, succinic acid or salicylic acid. In addition, pharmaceutically acceptable salts may be prepared from addition of an inorganic base or an organic base to the free acid. Salts derived from an inorganic base include, but are not limited to, the sodium, potassium, lithium, ammonium, calcium, magnesium, zinc, copper, manganese and aluminium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, histidine, caffeine, procaine, hydrabamine, choline, betaine, ethylendiamine, glucosamine, methylglucamine, theobromine, piperazine, N-ethylpiperidine, piperidine and polyamine resins. The compound of formula I can also be present in the form of zwitterions. Pharmaceutically acceptable salts of compounds of formula I of particular interest are the sodium salts or salts with tertiary amines.

The compounds of formula I can also be solvated, e.g., hydrated. The solvation can be effected in the course of the manufacturing process or can take place e.g. as a consequence of hygroscopic properties of an initially anhydrous compound of formula I (hydration). The term "pharmaceutically acceptable salts" also includes physiologically acceptable solvates.

The term "agonist" denotes a compound that enhances the activity of another compound or receptor site as defined e.g. in Goodman and Gilman's "The Pharmacological Basis of Therapeutics, 7th ed." in page 35, Macmillan Publ. Company, Canada, 1985. A "full agonist" effects a full response whereas a "partial agonist" effects less than full activation even when occupying the total receptor population. An "inverse agonist" produces an effect opposite to that of an agonist, yet binds to the same receptor binding-site.

The term "half maximal effective concentration" ($EC_{50}$) denotes the plasma concentration of a particular compound required for obtaining 50% of the maximum of a particular effect in vivo.

The term "therapeutically effective amount" denotes an amount of a compound of the present invention that, when administered to a subject, (i) treats or prevents the particular disease, condition or disorder, (ii) attenuates, ameliorates or eliminates one or more symptoms of the particular disease, condition, or disorder, or (iii) prevents or delays the onset of one or more symptoms of the particular disease, condition or disorder described herein. The therapeutically effective amount will vary depending on the compound, disease state being treated, the severity or the disease treated, the age and relative health of the subject, the route and form of administration, the judgment of the attending medical or veterinary practitioner, and other factors.

In detail, the present invention relates to compounds of the formula

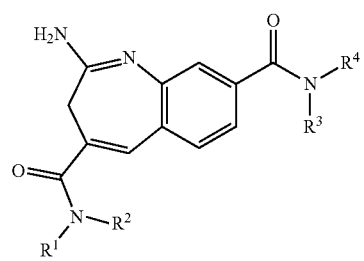

wherein
$R^1$ is $C_{3-7}$-alkyl or $C_{3-7}$-cycloalkyl,
$R^2$ is selected from the group consisting of $C_{1-7}$-alkyl, hydroxy-$C_{1-7}$-alkyl, $C_{2-7}$-alkenyl, $C_{3-7}$-alkinyl, amino-$C_{1-7}$-alkoxy-$C_{1-7}$-alkyl, amino-$C_{1-7}$-alkoxy-$C_{1-7}$-alkoxy-$C_{1-7}$-alkyl, halogen-$C_{1-7}$-alkyl, $C_{3-7}$-cycloalkyl-$C_{1-7}$-alkyl and phenyl-$C_{1-7}$-alkyl, wherein phenyl is unsubstituted or substituted by amino-$C_{1-7}$-alkyl;
$R^3$ is hydrogen;
$R^4$ is selected from the group consisting of
  phenyl, said phenyl being unsubstituted or substituted by one or two groups selected from the group consisting of $C_{1-7}$-alkyl, halogen, halogen-$C_{1-7}$-alkyl, $C_{1-7}$-alkoxy, hydroxy-$C_{1-7}$-alkyl, amino-$C_{1-7}$-alkyl, $C_{1-7}$-alkyl-amino-$C_{1-7}$-alkyl, di-$C_{1-7}$-alkyl-amino-$C_{1-7}$-alkyl, amino-$C_{2-7}$-alkenyl, $C_{1-7}$-alkyl-amino-$C_{2-7}$-alkenyl, di-$C_{1-7}$-alkyl-amino-$C_{2-7}$-alkenyl, $C_{1-7}$-alkyl-amino-$C_{2-7}$-alkinyl, di-$C_{1-7}$-alkyl-amino-$C_{2-7}$-alkinyl, benzyloxycarbonylamino-$C_{1-7}$-alkyl, amino-$C_{1-7}$-alkoxy, amino-$C_{1-7}$-alkoxy-$C_{1-7}$-alkoxy, amino-$C_{1-7}$-alkoxy-$C_{1-7}$-alkyl, amino-$C_{1-7}$-alkoxy-$C_{1-7}$-alkoxy-$C_{1-7}$-alkyl, $C_{1-7}$-alkylsulfonyl heterocyclylcarbonyl and phenyl-$C_{1-7}$-alkyl, wherein phenyl is unsubstituted or substituted by $C_{1-7}$-alkoxy or amino-$C_{1-7}$-alkyl, or
  heteroaryl, said heteroaryl being a 5- or 6-membered aromatic ring containing one, two or three heteroatoms selected from N, O or S and being unsubstituted or substituted by one or two groups selected from the group consisting of $C_{1-7}$-alkyl, halogen, halogen-$C_{1-7}$-alkyl, $C_{1-7}$-alkoxy, hydroxy-$C_{1-7}$-alkyl, amino-$C_{1-7}$-alkyl, $C_{1-7}$-alkyl-amino-$C_{1-7}$-alkyl, di-$C_{1-7}$-alkyl-amino-$C_{1-7}$-alkyl, amino-$C_{2-7}$-alkenyl, $C_{1-7}$-alkyl-amino-$C_{2-7}$-alkenyl, di-$C_{1-7}$-alkyl-amino-$C_{2-7}$-alkenyl, amino-$C_{2-7}$-alkinyl, $C_{1-7}$-alkyl-amino-$C_{2-7}$-alkinyl, di-$C_{1-7}$-alkyl-amino-$C_{2-7}$-alkinyl, benzyloxycarbonylamino-$C_{1-7}$-alkyl, amino-$C_{1-7}$-alkoxy, amino-$C_{1-7}$-alkoxy-$C_{1-7}$-alkoxy, amino-$C_{1-7}$-alkoxy-$C_{1-7}$-alkyl, amino-$C_{1-7}$-alkoxy-$C_{1-7}$-alkoxy-$C_{1-7}$-alkyl, $C_{1-7}$-alkylsulfonyl heterocyclylcarbonyl and phenyl-$C_{1-7}$-alkyl, wherein phenyl is unsubstituted or substituted by $C_{1-7}$-alkoxy or amino-$C_{1-7}$-alkyl,
or pharmaceutically acceptable salts thereof In one aspect, the invention relates to compounds of formula I, wherein $R^1$ is $C_{1-7}$-alkyl.

In particular, the invention is concerned with compounds of formula I, wherein $R^1$ is propyl or butyl. More particularly, $R^1$ is propyl.

In another aspect, the invention refers to compounds of formula I, wherein $R^2$ is selected from the group consisting of $C_{1-7}$-alkyl, $C_{2-7}$-alkenyl, $C_{3-7}$-alkinyl, halogen-$C_{1-7}$-alkyl, $C_{3-7}$-cycloalkyl-$C_{1-7}$-alkyl and hydroxy-$C_{1-7}$-alkyl. In another aspect, the invention refers to compounds of formula I, wherein $R^2$ is selected from the group consisting of $C_{1-7}$-alkyl, $C_{3-7}$-alkinyl, halogen-$C_{1-7}$-alkyl, $C_{3-7}$-cycloalkyl-$C_{1-7}$-alkyl and hydroxy-$C_{1-7}$-alkyl. In a further aspect, $R^2$ is selected from the group consisting of $C_{1-7}$-alkyl, $C_{3-7}$-alkinyl and hydroxy-$C_{1-7}$-alkyl. In particular, $R^2$ is $C_{1-7}$-alkyl or hydroxy-$C_{1-7}$-alkyl. More particularly, $R^2$ is $C_{1-7}$-alkyl. More particularly, $R^2$ is selected from the group consisting of propyl, 3-hydroxypropyl, cyclopropylmethyl and 3,3,3-trifluoropropyl.

In a particular aspect, the invention relates to compounds of formula I, wherein $R^1$ and $R^2$ are $C_{1-7}$-alkyl, particularly propyl.

In a further aspect, the invention relates to compounds of formula I, wherein $R^4$ is a 5- or 6-membered heteroaryl ring containing one, two or three heteroatoms selected from N, O or S and being unsubstituted or substituted by one or two groups selected from the group consisting of $C_{1-7}$-alkyl, halogen, halogen-$C_{1-7}$-alkyl, $C_{1-7}$-alkoxy, hydroxy-$C_{1-7}$-alkyl, amino-$C_{1-7}$-alkyl, $C_{1-7}$-alkyl-amino-$C_{1-7}$-alkyl, di-$C_{1-7}$-alkyl-amino-$C_{1-7}$-alkyl, amino-$C_{2-7}$-alkenyl, $C_{1-7}$-alkyl-amino-$C_{2-7}$-alkenyl, di-$C_{1-7}$-alkyl-amino-$C_{2-7}$-alkenyl, amino-$C_{2-7}$-alkinyl, $C_{1-7}$-alkyl-amino-$C_{2-7}$-alkinyl, di-$C_{1-7}$-alkyl-amino-$C_{2-7}$-alkinyl, benzyloxycarbonylamino-$C_{1-7}$-alkyl, amino-$C_{1-7}$-alkoxy, amino-$C_{1-7}$-alkoxy-$C_{1-7}$-alkoxy, amino-$C_{1-7}$-alkoxy-$C_{1-7}$-alkyl, amino-$C_{1-7}$-alkoxy-$C_{1-7}$-alkoxy-$C_{1-7}$-alkyl, $C_{1-7}$-alkylsulfonyl, heterocyclylcarbonyl and phenyl-$C_{1-7}$-alkyl, wherein phenyl is unsubstituted or substituted by $C_{1-7}$-alkoxy or amino-$C_{1-7}$-alkyl.

In another aspect, the invention refers to compounds of formula I, wherein $R^4$ is a 5- or 6-membered heteroaryl ring containing one, two or three heteroatoms selected from N, O or S and being unsubstituted or substituted by one or two groups selected from the group consisting of $C_{1-7}$-alkyl, halogen, halogen-$C_{1-7}$-alkyl, $C_{1-7}$-alkoxy, hydroxy-$C_{1-7}$-alkyl, amino-$C_{1-7}$-alkyl, amino-$C_{2-7}$-alkenyl, amino-$C_{2-7}$-alkinyl, amino-$C_{1-7}$-alkoxy, amino-$C_{1-7}$-alkoxy-$C_{1-7}$-alkoxy, amino-$C_{1-7}$-alkoxy-$C_{1-7}$-alkoxy-$C_{1-7}$-alkyl, $C_{1-7}$-alkylsulfonyl and heterocyclylcarbonyl.

In one aspect, the invention relates to compounds of formula I, wherein $R^4$ is a 5- or 6-membered heteroaryl ring containing one, two or three heteroatoms selected from N, O or S and being substituted by one or two groups selected from the group consisting of $C_{1-7}$-alkyl, halogen, $C_{1-7}$-alkoxy, hydroxy-$C_{1-7}$-alkyl, amino-$C_{1-7}$-alkyl, amino-$C_{2-7}$-alkenyl, amino-$C_{2-7}$-alkinyl, benzyloxycarbonylamino-$C_{1-7}$-alkyl, amino-$C_{1-7}$-alkoxy and phenyl-$C_{1-7}$-alkyl, wherein phenyl is unsubstituted or substituted by $C_{1-7}$-alkoxy or amino-$C_{1-7}$-alkyl. In a further aspect, $R^4$ is a 5- or 6-membered heteroaryl ring containing one, two or three heteroatoms selected from N, O or S and being substituted by one or two groups selected from the group consisting of $C_{1-7}$-alkyl, halogen, $C_{1-7}$-alkoxy, hydroxy-$C_{1-7}$-alkyl, amino-$C_{1-7}$-alkyl, amino-$C_{2-7}$-alkenyl, amino-$C_{2-7}$-alkinyl, amino-$C_{1-7}$-alkoxy, amino-$C_{1-7}$-alkoxy-$C_{1-7}$-alkoxy-$C_{1-7}$-alkyl and heterocyclylcarbonyl.

In particular, the invention relates to compounds of formula I, wherein $R^4$ is a 5- or 6-membered heteroaryl ring containing one, two or three heteroatoms selected from N, O or S. More particularly, the invention relates to heteraryl as defined herein before, wherein heteroaryl is selected from the group consisting of imidazolyl, pyrazolyl, oxazolyl, thiazolyl, pyridyl, pyridazinyl and pyrimidinyl, said heteroaryl being unsubstituted or substituted by one or two groups selected from the group consisting of $C_{1-7}$-alkyl, halogen, halogen-$C_{1-7}$-alkyl, $C_{1-7}$-alkoxy, hydroxy-$C_{1-7}$-alkyl, amino-$C_{1-7}$-alkyl, $C_{1-7}$-alkyl-amino-$C_{1-7}$-alkyl, di-$C_{1-7}$-alkyl-amino-$C_{1-7}$-alkyl, amino-$C_{2-7}$-alkenyl, $C_{1-7}$-alkyl-amino-$C_{2-7}$-alkenyl, di-$C_{1-7}$-alkyl-amino-$C_{2-7}$-alkenyl, $C_{1-7}$-alkyl-amino-$C_{2-7}$-alkinyl, di-$C_{1-7}$-alkyl-amino-$C_{2-7}$-alkinyl, benzyloxycarbonylamino-$C_{1-7}$-alkyl, amino-$C_{1-7}$-alkoxy, amino-$C_{1-7}$-alkoxy-$C_{1-7}$-alkoxy, amino-$C_{1-7}$-alkoxy-$C_{1-7}$-alkyl, amino-$C_{1-7}$-alkoxy-$C_{1-7}$-alkoxy-$C_{1-7}$-alkyl, $C_{1-7}$-alkylsulfonyl, heterocyclylcarbonyl and phenyl-$C_{1-7}$-alkyl, wherein phenyl is unsubstituted or substituted by $C_{1-7}$-alkoxy or amino-$C_{1-7}$-alkyl. In a particular aspect, the 5- or 6-membered heteroaryl ring is pyridyl.

In one aspect, the invention relates to compounds of formula I, wherein $R^4$ is unsubstituted heteroaryl selected from selected from the group consisting of imidazolyl, pyrazolyl, oxazolyl, thiazolyl, pyridyl, pyridazinyl and pyrimidinyl.

In another aspect, the invention relates to compounds of formula I, wherein $R^4$ is phenyl, said phenyl being unsubstituted or substituted by one or two groups selected from the group consisting of $C_{1-7}$-alkyl, halogen, halogen-$C_{1-7}$-alkyl, $C_{1-7}$-alkoxy, hydroxy-$C_{1-7}$-alkyl, amino-$C_{1-7}$-alkyl, $C_{1-7}$-alkyl-amino-$C_{1-7}$-alkyl, di-$C_{1-7}$-alkyl-amino-$C_{1-7}$-alkyl, amino-$C_{2-7}$-alkenyl, $C_{1-7}$-alkyl-amino-$C_{2-7}$-alkenyl, di-$C_{1-7}$-alkyl-amino-$C_{2-7}$-alkenyl, amino-$C_{2-7}$-alkinyl, $C_{1-7}$-alkyl-amino-$C_{2-7}$-alkinyl, di-$C_{1-7}$-alkyl-amino-$C_{2-7}$-alkinyl, benzyloxycarbonylamino-$C_{1-7}$-alkyl, amino-$C_{1-7}$-alkoxy, amino-$C_{1-7}$-alkoxy-$C_{1-7}$-alkoxy, amino-$C_{1-7}$-alkoxy-$C_{1-7}$-alkyl, amino-$C_{1-7}$-alkoxy-$C_{1-7}$-alkoxy-$C_{1-7}$-alkyl, $C_{1-7}$-alkylsulfonyl, heterocyclylcarbonyl and phenyl-$C_{1-7}$-alkyl, wherein phenyl is unsubstituted or substituted by $C_{1-7}$-alkoxy or amino-$C_{1-7}$-alkyl.

In one aspect, the invention relates to compounds of formula I, wherein $R^4$ is phenyl, said phenyl being unsubstituted or substituted by one or two groups selected from the group consisting of $C_{1-7}$-alkyl, halogen, halogen-$C_{1-7}$-alkyl, $C_{1-7}$-alkoxy, hydroxy-$C_{1-7}$-alkyl, amino-$C_{1-7}$-alkyl, amino-$C_{2-7}$-alkenyl, amino-$C_{2-7}$-alkinyl, amino-$C_{1-7}$-alkoxy, amino-$C_{1-7}$-alkoxy-$C_{1-7}$-alkoxy, amino-$C_{1-7}$-alkoxy-$C_{1-7}$-alkoxy-$C_{1-7}$-alkyl, $C_{1-7}$-alkylsulfonyl and heterocyclylcarbonyl.

In particular, the invention relates to compounds of formula I, wherein $R^4$ is phenyl, said phenyl being unsubstituted or substituted by one or two groups selected from the group consisting of $C_{1-7}$-alkyl, halogen, halogen-$C_{1-7}$-alkyl, $C_{1-7}$-alkoxy, amino-$C_{1-7}$-alkyl, amino-$C_{1-7}$-alkoxy, amino-$C_{1-7}$-alkoxy-$C_{1-7}$-alkoxy, amino-$C_{1-7}$-alkoxy-$C_{1-7}$-alkyl, amino-$C_{1-7}$-alkoxy-$C_{1-7}$-alkoxy-$C_{1-7}$-alkyl, $C_{1-7}$-alkylsulfonyl and heterocyclylcarbonyl.

In one aspect, compounds of formula I of the invention are those, wherein $R^4$ is phenyl substituted by one group selected from the group consisting of $C_{1-7}$-alkyl, halogen, halogen-$C_{1-7}$-alkyl, $C_{1-7}$-alkoxy, amino-$C_{1-7}$-alkyl, amino-$C_{1-7}$-alkoxy, amino-$C_{1-7}$-alkoxy-$C_{1-7}$-alkoxy, amino-$C_{1-7}$-alkoxy-$C_{1-7}$-alkyl, amino-$C_{1-7}$-alkoxy-$C_{1-7}$-alkoxy-$C_{1-7}$-alkyl, $C_{1-7}$-alkylsulfonyl and heterocyclylcarbonyl.

In a particular aspect, the invention relates to compounds of formula I, wherein $R^4$ is

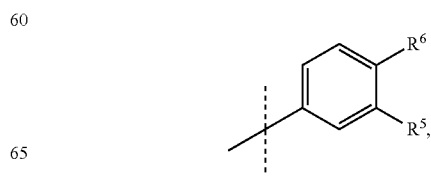

wherein one of $R^5$ or $R^6$ is selected from the group consisting of $C_{1-7}$-alkyl, halogen, halogen-$C_{1-7}$-alkyl, $C_{1-7}$-alkoxy, amino-$C_{1-7}$-alkyl, amino-$C_{1-7}$-alkoxy, amino-$C_{1-7}$-alkoxy-$C_{1-7}$-alkoxy, amino-$C_{1-7}$-alkoxy-$C_{1-7}$-alkyl, amino-$C_{1-7}$-alkoxy-$C_{1-7}$-alkoxy-$C_{1-7}$-alkyl, $C_{1-7}$-alkylsulfonyl and heterocyclylcarbonyl, and the other one of $R^5$ and $R^6$ is hydrogen.

In another aspect, the invention refers to compounds of formula I, wherein $R^4$ is unsubstituted phenyl.

In a further aspect, the invention relates to compounds of formula I, wherein $R^1$ is $C_{3-7}$-alkyl or $C_{3-7}$-cycloalkyl, $R^2$ is selected from the group consisting of $C_{1-7}$-alkyl, $C_{2-7}$-alkenyl, $C_{3-7}$-alkinyl, hydroxy-$C_{1-7}$-alkyl, amino-$C_{1-7}$-alkoxy-$C_{1-7}$-alkoxy-$C_{1-7}$-alkyl, halogen-$C_{1-7}$-alkyl and $C_{3-7}$-cycloalkyl-$C_{1-7}$-alkyl;

$R^3$ is hydrogen;

$R^4$ is selected from the group consisting of
phenyl, said phenyl being unsubstituted or substituted by one or two groups selected from the group consisting of $C_{1-7}$-alkyl, halogen, halogen-$C_{1-7}$-alkyl, $C_{1-7}$-alkoxy, hydroxy-$C_{1-7}$-alkyl, amino-$C_{1-7}$-alkyl, amino-$C_{2-7}$-alkenyl, amino-$C_{2-7}$-alkinyl, amino-$C_{1-7}$-alkoxy, amino-$C_{1-7}$-alkoxy-$C_{1-7}$-alkoxy, amino-$C_{1-7}$-alkoxy-$C_{1-7}$-alkoxy-$C_{1-7}$-alkyl, $C_{1-7}$-alkylsulfonyl and heterocyclylcarbonyl, or
heteroaryl, said heteroaryl being a 5- or 6-membered aromatic ring containing one, two or three heteroatoms selected from N, O or S and being unsubstituted or substituted by one or two groups selected from the group consisting of $C_{1-7}$-alkyl, halogen, halogen-$C_{1-7}$-alkyl, $C_{1-7}$-alkoxy, hydroxy-$C_{1-7}$-alkyl, amino-$C_{1-7}$-alkyl, amino-$C_{2-7}$-alkenyl, amino-$C_{2-7}$-alkinyl, amino-$C_{1-7}$-alkoxy, amino-$C_{1-7}$-alkoxy-$C_{1-7}$-alkoxy, amino-$C_{1-7}$-alkoxy-$C_{1-7}$-alkoxy-C alkyl, $C_{1-7}$-alkylsulfonyl and heterocyclylcarbonyl, or pharmaceutically acceptable salts thereof.

Particular compounds of formula I according to the invention are the following:

2-amino-N4,N4-dipropyl-N8-(3-pyridyl)-3H-1-benzazepine-4,8-dicarboxamide,
2-amino-N4,N4-dipropyl-N8-pyrimidin-5-yl-3H-1-benzazepine-4,8-dicarboxamide,
2-amino-N4,N4-dipropyl-N8-(4-pyridyl)-3H-1-benzazepine-4,8-dicarboxamide,
2-amino-N4,N4-dipropyl-N8-phenyl-3H-1-benzazepine-4,8-dicarboxamide,
2-amino-N8-[6-(aminomethyl)-3-pyridyl]-N4,N4-dipropyl-3H-1-benzazepine-4,8-dicarboxamide,
2-amino-N8-[5-(hydroxymethyl)-3-pyridyl]-N4,N4-dipropyl-3H-1-benzazepine-4,8-dicarboxamide,
2-amino-N8-[6-(hydroxymethyl)-3-pyridyl]-N4,N4-dipropyl-3H-1-benzazepine-4,8-dicarboxamide,
2-amino-N8-(3-methylsulfonylphenyl)-N4,N4-dipropyl-3H-1-benzazepine-4,8-dicarboxamide,
2-amino-N4,N4-dipropyl-N8-thiazol-5-yl-3H-1-benzazepine-4,8-dicarboxamide,
2-amino-N8-(4-chlorophenyl)-N4,N4-dipropyl-3H-1-benzazepine-4,8-dicarboxamide,
2-amino-N4,N4-dipropyl-N8-thiazol-2-yl-3H-1-benzazepine-4,8-dicarboxamide,
2-amino-N8-(3-methylimidazol-4-yl)-N4,N4-dipropyl-3H-1-benzazepine-4,8-dicarboxamide,
2-amino-N8-(4-fluorophenyl)-N4,N4-dipropyl-3H-1-benzazepine-4,8-dicarboxamide,
2-amino-N8-(m-tolyl)-N4,N4-dipropyl-3H-1-benzazepine-4,8-dicarboxamide,
2-amino-N4,N4-dipropyl-N8-[3-(pyrrolidine-1-carbonyl)phenyl]-3H-1-benzazepine-4,8-dicarboxamide,
2-amino-N4,N4-dipropyl-N8-[5-(pyrrolidine-1-carbonyl)-3-pyridyl]-3H-1-benzazepine-4,8-dicarboxamide,
2-amino-N8-[3-(2-aminoethyl)phenyl]-N4,N4-dipropyl-3H-1-benzazepine-4,8-dicarboxamide,
2-amino-N8-(5-methyl-3-pyridyl)-N4,N4-dipropyl-3H-1-benzazepine-4,8-dicarboxamide,
2-amino-N8-(3-fluorophenyl)-N4,N4-dipropyl-3H-1-benzazepine-4,8-dicarboxamide,
2-amino-N8-(5-fluoro-3-pyridyl)-N4,N4-dipropyl-3H-1-benzazepine-4,8-dicarboxamide,
2-amino-N8-(2-methyl-3-pyridyl)-N4,N4-dipropyl-3H-1-benzazepine-4,8-dicarboxamide,
2-amino-N8-(6-methyl-3-pyridyl)-N4,N4-dipropyl-3H-1-benzazepine-4,8-dicarboxamide,
2-amino-N8-(3,5-dimethylphenyl)-N4,N4-dipropyl-3H-1-benzazepine-4,8-dicarboxamide,
2-amino-N8-[4-(aminomethyl)phenyl]-N4,N4-dipropyl-3H-1-benzazepine-4,8-dicarboxamide,
2-amino-N8-[4-(2-aminoethyl)phenyl]-N4,N4-dipropyl-3H-1-benzazepine-4,8-dicarboxamide,
2-amino-N4-(3-hydroxypropyl)-N8-(m-tolyl)-N4-propyl-3H-1-benzazepine-4,8-dicarboxamide,
2-amino-N8-(o-tolyl)-N4,N4-dipropyl-3H-1-benzazepine-4,8-dicarboxamide,
2-amino-N4,N4-dipropyl-N8-(p-tolyl)-3H-1-benzazepine-4,8-dicarboxamide,
2-amino-N8-(3-ethylphenyl)-N4,N4-dipropyl-3H-1-benzazepine-4,8-dicarboxamide,
2-amino-N8-(3-methoxyphenyl)-N4,N4-dipropyl-3H-1-benzazepine-4,8-dicarboxamide,
2-amino-N4,N4-dipropyl-N8-[3-(trifluoromethyl)phenyl]-3H-1-benzazepine-4,8-dicarboxamide,
2-amino-N8-(3-chlorophenyl)-N4,N4-dipropyl-3H-1-benzazepine-4,8-dicarboxamide,
2-amino-N8-[5-(aminomethyl)-3-pyridyl]-N4,N4-dipropyl-3H-1-benzazepine-4,8-dicarboxamide,
2-amino-N4,N4-dipropyl-N8-pyridazin-4-yl-3H-1-benzazepine-4,8-dicarboxamide,
2-amino-N8-(6-ethoxy-3-pyridyl)-N4,N4-dipropyl-3H-1-benzazepine-4,8-dicarboxamide,
2-amino-N8-[3-(aminomethyl)phenyl]-N4,N4-dipropyl-3H-1-benzazepine-4,8-dicarboxamide,
2-amino-N8-(1-methylpyrazol-3-yl)-N4,N4-dipropyl-3H-1-benzazepine-4,8-dicarboxamide,
2-amino-N8-oxazol-2-yl-N4,N4-dipropyl-3H-1-benzazepine-4,8-dicarboxamide,
2-amino-N4-(3-hydroxypropyl)-N4-propyl-N8-(3-pyridyl)-3H-1-benzazepine-4,8-dicarboxamide,
2-amino-N8-(5-methoxy-3-pyridyl)-N4,N4-dipropyl-3H-1-benzazepine-4,8-dicarboxamide,
2-amino-N8-(m-tolyl)-N4-propyl-N4-prop-2-ynyl-3H-1-benzazepine-4,8-dicarboxamide,
2-amino-N4,N4-dibutyl-N8-(m-tolyl)-3H-1-benzazepine-4,8-dicarboxamide,
2-amino-N8-[3-(aminomethyl)-5-methyl-phenyl]-N4,N4-dipropyl-3H-1-benzazepine-4,8-dicarboxamide,
2-amino-N8-(5-ethoxy-3-pyridyl)-N4,N4-dipropyl-3H-1-benzazepine-4,8-dicarboxamide,
2-amino-N8-[3-[2-(2-aminoethoxy)ethoxy]phenyl]-N4,N4-dipropyl-3H-1-benzazepine-4,8-dicarboxamide,
2-amino-N8-[5-(5-aminopentoxy)-3-pyridyl]-N4,N4-dipropyl-3H-1-benzazepine-4,8-dicarboxamide,
2-amino-N8-[3-[2-(2-aminoethoxy)ethoxymethyl]phenyl]-N4,N4-dipropyl-3H-1-benzazepine-4,8-dicarboxamide, 2-amino-N8-[5-(3-aminoprop-1-ynyl)-3-pyridyl]-N4,N4-dipropyl-3H-1-benzazepine-4,8-dicarboxamide,
2-amino-N4-[3-[2-(2-aminoethoxy)ethoxy]propyl]-N8-(m-tolyl)-N4-propyl-3H-1-benzazepine-4,8-dicarboxamide,
2-amino-N8-[5-(3-aminopropyl)-3-pyridyl]-N4,N4-dipropyl-3H-1-benzazepine-4,8-dicarboxamide,
2-amino-N8-(m-tolyl)-N4-propyl-N4-(3,3,3-trifluoropropyl)-3H-1-benzazepine-4,8-dicarboxamide,
2-amino-N8-[5-[(E)-3-aminoprop-1-enyl]-3-pyridyl]-N4,N4-dipropyl-3H-1-benzazepine-4,8-dicarboxamide,
2-amino-N4-(cyclopropylmethyl)-N8-(m-tolyl)-N4-propyl-3H-1-benzazepine-4,8-dicarboxamide,
and pharmaceutically acceptable salts thereof.

Further particular compounds of formula I according to the invention are the following:
2-amino-N8-[3-(2-aminoethyl)phenyl]-N4,N4-dipropyl-3H-1-benzazepine-4,8-dicarboxamide,
2-amino-N4-isobutyl-N8-(m-tolyl)-N4-propyl-3H-1-benzazepine-4,8-dicarboxamide,
2-amino-N4-[3-(3-aminopropoxy)propyl]-N8-(m-tolyl)-N4-propyl-3H-1-benzazepine-4,8-dicarboxamide,
2-amino-N8-[3-(5-aminopentyl)phenyl]-N4,N4-dipropyl-3H-1-benzazepine-4,8-dicarboxamide,
2-amino-N8-[4-(5-aminopentyl)phenyl]-N4,N4-dipropyl-3H-1-benzazepine-4,8-dicarboxamide,
2-amino-N8-[3-(3-aminopropyl)phenyl]-N4,N4-dipropyl-3H-1-benzazepine-4,8-dicarboxamide,
2-amino-N4-[[4-(aminomethyl)phenyl]methyl]-N8-(m-tolyl)-N4-propyl-3H-1-benzazepine-4,8-dicarboxamide,
2-amino-N8-[4-(3-aminopropyl)phenyl]-N4,N4-dipropyl-3H-1-benzazepine-4,8-dicarboxamide,
2-amino-N8-[4-(3-aminopropyl)phenyl]-N4,N4-dipropyl-3H-1-benzazepine-4,8-dicarboxamide,
2-amino-N8-[3-(2-aminoethyl)-4-fluoro-phenyl]-N4,N4-dipropyl-3H-1-benzazepine-4,8-dicarboxamide,
2-amino-N8-[3-(2-aminoethyl)-5-chloro-phenyl]-N4,N4-dipropyl-3H-1-benzazepine-4,8-dicarboxamide,
2-amino-N4-butyl-N4-(2-hydroxyethyl)-N8-(m-tolyl)-3H-1-benzazepine-4,8-dicarboxamide,
2-amino-N8-[5-(2-aminoethoxy)-3-pyridyl]-N4,N4-dipropyl-3H-1-benzazepine-4,8-dicarboxamide,
benzyl-N-[[5-[[2-amino-4-(dipropylcarbamoyl)-3H-1-benzazepine-8-carbonyl]amino]-3-pyridyl]methyl]carbamate,
2-amino-N8-[5-[(E)-3-aminoprop-1-enyl]-3-pyridyl]-N4,N4-dipropyl-3H-1-benzazepine-4,8-dicarboxamide,
2-amino-N8-[5-(2-phenylethyl)-3-pyridyl]-N4,N4-dipropyl-3H-1-benzazepine-4,8-dicarboxamide,
2-amino-N8-[5-[2-(4-methoxyphenyl)ethyl]-3-pyridyl]-N4,N4-dipropyl-3H-1-benzazepine-4,8-dicarboxamide,
2-amino-N8-[5-[2-[4-(aminomethyl)phenyl]ethyl]-3-pyridyl]-N4,N4-dipropyl-3H-1-benzazepine-4,8-dicarboxamide,
2-amino-N8-[5-(5-aminopentyl)-3-pyridyl]-N4,N4-dipropyl-3H-1-benzazepine-4,8-dicarboxamide,
2-amino-N8-[5-[2-(3-methoxyphenyl)ethyl]-3-pyridyl]-N4,N4-dipropyl-3H-1-benzazepine-4,8-dicarboxamide,
2-amino-N8-[5-(6-aminohexyl)-3-pyridyl]-N4,N4-dipropyl-3H-1-benzazepine-4,8-dicarboxamide,
2-amino-N8-[6-(3-aminopropyl)-3-pyridyl]-N4,N4-dipropyl-3H-1-benzazepine-4,8-dicarboxamide,
2-amino-N8-[5-(4-aminobutyl)-3-pyridyl]-N4,N4-dipropyl-3H-1-benzazepine-4,8-dicarboxamide,
2-amino-N8-[6-(4-aminobutyl)-3-pyridyl]-N4,N4-dipropyl-3H-1-benzazepine-4,8-dicarboxamide,
2-amino-N8-[5-[(dimethylamino)methyl]-3-pyridyl]-N4,N4-dipropyl-3H-1-benzazepine-4,8-dicarboxamide,
2-amino-N4-(cyclopropylmethyl)-N8-(5-ethoxy-3-pyridyl)-N4-propyl-3H-1-benzazepine-4,8-dicarboxamide,
2-amino-N8-[5-(2-aminoethyl)-3-pyridyl]-N4,N4-dipropyl-3H-1-benzazepine-4,8-dicarboxamide,
and pharmaceutically acceptable salts thereof.

More particularly, the invention relates to compounds of formula I that are the following:
2-amino-N4,N4-dipropyl-N8-(3-pyridyl)-3H-1-benzazepine-4,8-dicarboxamide,
2-amino-N4,N4-dipropyl-N8-pyrimidin-5-yl-3H-1-benzazepine-4,8-dicarboxamide,
2-amino-N8-(4-chlorophenyl)-N4,N4-dipropyl-3H-1-benzazepine-4,8-dicarboxamide,
2-amino-N8-(m-tolyl)-N4,N4-dipropyl-3H-1-benzazepine-4,8-dicarboxamide,
2-amino-N4,N4-dipropyl-N8-[3-(pyrrolidine-1-carbonyl)phenyl]-3H-1-benzazepine-4,8-dicarboxamide,
2-amino-N8-(6-methyl-3-pyridyl)-N4,N4-dipropyl-3H-1-benzazepine-4,8-dicarboxamide,
2-amino-N8-(3,5-dimethylphenyl)-N4,N4-dipropyl-3H-1-benzazepine-4,8-dicarboxamide,
2-amino-N4-(3-hydroxypropyl)-N8-(m-tolyl)-N4-propyl-3H-1-benzazepine-4,8-dicarboxamide,
2-amino-N4,N4-dipropyl-N8-(p-tolyl)-3H-1-benzazepine-4,8-dicarboxamide,
2-amino-N8-(3-ethylphenyl)-N4,N4-dipropyl-3H-1-benzazepine-4,8-dicarboxamide,
2-amino-N8-(3-methoxyphenyl)-N4,N4-dipropyl-3H-1-benzazepine-4,8-dicarboxamide,
2-amino-N8-(3-chlorophenyl)-N4,N4-dipropyl-3H-1-benzazepine-4,8-dicarboxamide,
2-amino-N8-[5-(aminomethyl)-3-pyridyl]-N4,N4-dipropyl-3H-1-benzazepine-4,8-dicarboxamide,
2-amino-N4,N4-dipropyl-N8-pyridazin-4-yl-3H-1-benzazepine-4,8-dicarboxamide,
2-amino-N8-(6-ethoxy-3-pyridyl)-N4,N4-dipropyl-3H-1-benzazepine-4,8-dicarboxamide,
2-amino-N8-(5-methoxy-3-pyridyl)-N4,N4-dipropyl-3H-1-benzazepine-4,8-dicarboxamide,
2-amino-N8-(5-ethoxy-3-pyridyl)-N4,N4-dipropyl-3H-1-benzazepine-4,8-dicarboxamide,
2-amino-N8-[3-[2-(2-aminoethoxy)ethoxymethyl]phenyl]-N4,N4-dipropyl-3H-1-benzazepine-4,8-dicarboxamide,
2-amino-N8-(m-tolyl)-N4-propyl-N4-(3,3,3-trifluoropropyl)-3H-1-benzazepine-4,8-dicarboxamide,
2-amino-N4-(cyclopropylmethyl)-N8-(m-tolyl)-N4-propyl-3H-1-benzazepine-4,8-dicarboxamide,
and pharmaceutically acceptable salts thereof.

In a further particular aspect, the compound of formula I according to the invention is selected from the group consisting of
2-amino-N8-[3-(2-aminoethyl)phenyl]-N4,N4-dipropyl-3H-1-benzazepine-4,8-dicarboxamide,
2-amino-N4-isobutyl-N8-(m-tolyl)-N4-propyl-3H-1-benzazepine-4,8-dicarboxamide,
2-amino-N8-[3-(3-aminopropyl)phenyl]-N4,N4-dipropyl-3H-1-benzazepine-4,8-dicarboxamide,
benzyl-N-[[5-[[2-amino-4-(dipropylcarbamoyl)-3H-1-benzazepine-8-carbonyl]amino]-3-pyridyl]methyl]carbamate,
2-amino-N8-[5-(2-phenylethyl)-3-pyridyl]-N4,N4-dipropyl-3H-1-benzazepine-4,8-dicarboxamide,
2-amino-N4-(cyclopropylmethyl)-N8-(5-ethoxy-3-pyridyl)-N4-propyl-3H-1-benzazepine-4,8-dicarboxamide,
and pharmaceutically acceptable salts thereof.

A further aspect of the present invention is the process for the manufacture of compounds of formula I as defined above, which process comprises
coupling a compound of the formula II

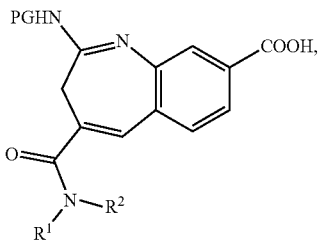

wherein $R^1$ and $R^2$ are as defined herein before and PG is a protecting group, with an amine of the formula III

wherein $R^3$ and $R^4$ are as defined herein before, under basic conditions in the presence of a coupling agent and removing the protecting group PG under acidic conditions to obtain a compound of the formula I

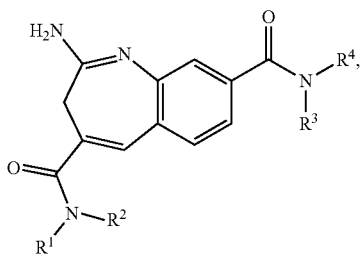

wherein $R^1$ to $R^4$ are as defined herein before, and, if desired, converting the compound obtained into a pharmaceutically acceptable salt.

It will be appreciated, that the compounds of general formula I in this invention may be derivatised at functional groups to provide derivatives which are capable of conversion back to the parent compound in vivo. Physiologically acceptable and metabolically labile derivatives, which are capable of producing the parent compounds of general formula I in vivo are also within the scope of this invention.

In particular, a suitable protecting group PG is an aminoprotecting group selected from Boc (tert-butoxycarbonyl), benzyl (Bz) and benzyloxycarbonyl (Cbz). In particular, the protecting group is Boc.

"Removing the protecting group PG under acidic conditions" means treating the protected compound with acids in a suitable solvent, for instance trifluoroacetic acid (TFA) in a solvent such as dichloromethane (DCM) can be employed.

A suitable "coupling agent" for the reaction of compounds of formula II with amines of formula III is selected from the group consisting of N,N'-carbonyldiimidazole (CDI), N,N'-dicyclohexylcarbodiimide (DCC), 1-(3-dimethylaminopropyl)-3-ethylcarbodiimide hydrochloride (EDCI), 1-[bis(dimethylamino)-methylene]-1H-1,2,3-triazolo[4,5-b]pyridinium-3-oxide hexafluorophosphate (HATU), 1-hydroxy-1,2,3-benzotriazole (HOBT), O-benzotriazole-N,N,N',N'-tetramethyl-uronium-hexafluoro-phosphate (HBTU) or O-benzotriazol-1-yl-N,N,N',N'-tetramethyluronium tetrafluoroborate (TBTU). In particular, the coupling agent is TBTU. Suitable bases include triethylamine, N-methylmorpholine and, particularly, diisopropylethylamine.

"Under basic conditions" means the presence of a base, in particular a base selected from the group consisting of triethylamine, N-methylmorpholine and, particularly, diisopropylethylamine. Typically, the reaction is carried out in inert solvents such as dimethylformamide or dichloromethane at room temperature.

The invention further relates to compounds of formula I as defined above obtainable according to a process as defined above.

The compounds of the present invention can be prepared by any conventional means. Suitable processes for synthesizing these compounds as well as their starting materials are provided in the schemes below and in the examples. All substituents, in particular, $R^1$ to $R^4$ are as defined above unless otherwise indicated. Furthermore, and unless explicitly otherwise stated, all reactions, reaction conditions, abbreviations and symbols have the meanings well known to a person of ordinary skill in organic chemistry.

A general synthetic route for preparing the compounds of formula I is shown in Scheme 1 below.

Compounds of formula I can be prepared according to Scheme 1. A coupling reaction between carboxylic acid A and a selected amine IV gives the amide of formula V, which is then protected with an amino protecting group such as Boc to obtain a compound of formula VI. Hydrolysis of the compound of formula VI leads to a carboxylic acid of formula II. The carboxylic acid of formula II is then coupled with a selected amine III to obtain an amide of formula VII. Finally, the compound of formula I is obtained by deprotection of the amino protecting group (e.g. Boc). In some cases, the compound of formula VII may contain an additional acid labile protection group originated from amine IV or amine III, like Boc or TBS, which will be removed also in the final deprotection step.

A coupling reagent, like HBTU, is used to couple the carboxylic acid of formula A and a selected amine IV in the presence of a base, like DIPEA, in a solvent like DCM at ambient or elevated temperature to give a compound of formula V.

Then, the compound of formula V is protected with an amino protecting group, in particular with Boc, to provide a compound of formula VI.

The compound of formula VI is hydrolyzed by a base, in particular LiOH, in a suitable solvent, for example a mixed solvent like THF/MeOH/$H_2O$, at ambient or elevated temperature to obtain a carboxylic acid of formula II.

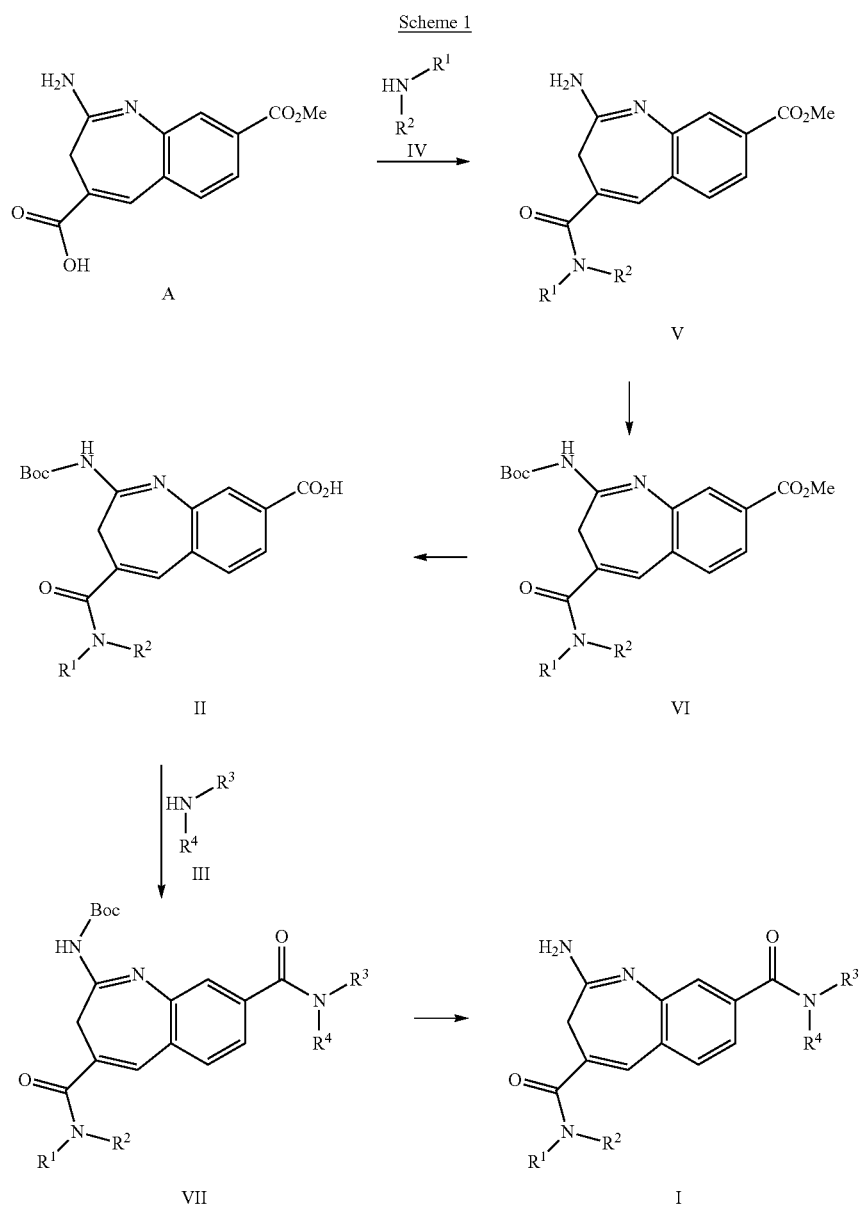

Scheme 1

The carboxylic acid of formula II is then reacted with a selected amine III under the assistance of a suitable coupling reagent, in particular HBTU, in a solvent like DCM and in the presence of a base, in particular DIPEA, at ambient or elevated temperature to result in a compound of formula VII.

Finally, a compound of formula I is obtained by deprotecting the compound of formula VII with TFA in dichloromethane and subsequent purification by prep-HPLC. In some cases, besides the Boc protection group at amidine, a compound of formula VII may also contain an additional acid labile protection group, like Boc or TBS originated from amine IV or III, which will be also removed in this step.

If one of the starting materials contains one or more functional groups which are not stable or are reactive under the reaction conditions of one or more reaction steps, appropriate protecting groups (PG) (as described e.g. in T. W. Greene et al., Protective Groups in Organic Chemistry, John Wiley and Sons Inc. New York 1999, 3rd edition) can be introduced before the critical step applying methods well known in the art. Such protecting groups can be removed at a later stage of the synthesis using standard methods known in the art. In some cases, besides the Boc protection group at amidine, a compound of formula VII may also contain an additional acid labile protection group, like Boc or TBS originated from amine II or VI, which will be also removed in this step.

If one or more compounds of the formula contain chiral centers, compounds of formula I can be obtained as mixtures of diastereomers or enantiomers, which can be separated by methods well known in the art, e.g. (chiral) HPLC or crystallization. Racemic compounds can e.g. be separated into their antipodes via diastereomeric salts by crystallization or by separation of the antipodes by specific chromatographic methods using either a chiral adsorbent or a chiral eluent.

As described herein before, the compounds of formula I of the present invention can be used as medicaments for the treatment of diseases which are mediated by TLR agonists, in particular for the treatment of diseases which are mediated by TLR8 agonists.

The compounds defined in the present invention are agonists of TLR8 receptors in cellular assays in vitro. Accordingly, the compounds of the present invention are expected to be potentially useful agents in the treatment of diseases or medical conditions that may benefit from the activation of the immune system via TLR8 agonists. They are useful in the treatment or prevention of diseases such as cancer, autoimmune diseases, inflammation, sepsis, allergy, asthma, graft rejection, graft-versus-host disease, immunodeficiencies, and infectious diseases.

In more detail, the compounds of formula I of the present invention are useful in oncology, i.e. they may be used in the treatment of common cancers including bladder cancer, head and neck cancer, prostate cancer, colorectal cancer, kidney cancer, breast cancer, lung cancer, ovarian cancer, cervical cancer, liver cancer, pancreatic cancer, bowel and colon cancer, stomach cancer, thyroid cancer, melanoma, skin and brain tumors and malignancies affecting the bone marrow such as leukemias and lymphoproliferative systems, such as Hodgkin's and non-Hodgkin's lymphoma; including the prevention (e.g. vaccination) and treatment of metastatic cancer and tumor recurrences, and paraneoplastic syndromes.

The compounds of formula I of the present invention are also useful in the treatment of autoimmune diseases. An "autoimmune disease" is a disease or disorder arising from and directed against an individual's own tissues or organs or a co-segregate or manifestation thereof or resulting condition therefrom. "Autoimmune disease" can be an organ-specific disease (i.e., the immune response is specifically directed against an organ system such as the endocrine system, the hematopoietic system, the skin, the cardiopulmonary system, the gastrointestinal and liver systems, the renal system, the thyroid, the ears, the neuromuscular system, the central nervous system, etc.) or a systemic disease which can affect multiple organ systems (for example, systemic lupus erythematosus (SLE), rheumatoid arthritis, polymyositis, etc.). In a particular aspect, the autoimmune disease is associated with the skin, muscle tissue, and/or connective tissue.

Particular autoimmune diseases include autoimmune rheumatologic disorders (such as, for example, rheumatoid arthritis, Sjogren's syndrome, scleroderma, lupus such as SLE and lupus nephritis, polymyositis/dermatomyositis, cryoglobulinemia, anti-phospholipid antibody syndrome, and psoriatic arthritis), autoimmune gastrointestinal and liver disorders (such as, for example, inflammatory bowel diseases, ulcerative colitis and Crohn's disease), autoimmune gastritis and pernicious anemia, autoimmune hepatitis, primary biliary cirrhosis, primary sclerosing cholangitis, and celiac disease), vasculitis (such as, for example, ANCA-negative vasculitis and ANCA-associated vasculitis, including Churg-Strauss vasculitis, Wegener's granulomatosis, and microscopic polyangiitis), autoimmune neurological disorders (such as, for example, multiple sclerosis, opsoclonus myoclonus syndrome, myasthenia gravis, neuromyelitis optica, Parkinson's disease, Alzheimer's disease, and autoimmune polyneuropathies), renal disorders (such as, for example, glomerulonephritis, Goodpasture's syndrome, and Berger's disease), autoimmune dermatologic disorders (such as, for example, psoriasis, urticaria, hives, pemphigus vulgaris, bullous pemphigoid, and cutaneous lupus erythematosus), hematologic disorders (such as, for example, thrombocytopenic purpura, thrombotic thrombocytopenic purpura, post-transfusion purpura, and autoimmune hemolytic anemia), atherosclerosis, uveitis, autoimmune hearing diseases (such as, for example, inner ear disease and hearing loss), Behcet's disease, Raynaud's syndrome, organ transplant, and autoimmune endocrine disorders (such as, for example, diabetic-related autoimmune diseases such as insulin-dependent diabetes mellitus (IDDM), Addison's disease, and autoimmune thyroid disease (e.g., Graves' disease and thyroiditis)), allergic conditions and responses, food allergies, drug allergies, insect allergies, rare allergic disorders such as mastocytosis, allergic reaction, eczema including allergic or atopic eczema, asthma such as bronchial asthma and auto-immune asthma, conditions involving infiltration of myeloid cells and T cells and chronic inflammatory responses:

The compounds of formula I of the present invention are also useful in the treatment of infectious diseases. Thus, they may be useful in the treatment of viral diseases, in particular for diseases caused by infection with viruses selected from the group consisting of papilloma viruses, such as human papilloma virus (HPV) and those that cause genital warts, common warts and plantar warts, herpes simplex virus (HSV), molluscum contagiosum, hepatitis B virus (HBV), hepatitis C virus (HCV), Dengue virus, variola virus, human immunodeficiency virus (HIV), cytomegalovirus (CMV), varicella zoster virus (VZV), rhinovirus, enterovirus, adenovirus, coronavirus (e.g. SARS), influenza, mumps and parainfluenza.

They may also be useful in the treatment of bacterial diseases, in particular for diseases caused by infection with bacteria selected from the group consisting of *mycobacterium* such as *mycobacterium tuberculosis, mycobacterium avium* and *mycobacterium leprae*. The compounds of formula I of the present invention may further be useful in the treatment of other infectious diseases, such as *chlamydia*, fungal diseases, in particular fungal diseases selected from the group consisting of candidiasis, aspergillosis and cryptococcal meningitis, and parasitic diseases such as *Pneumocystis carnii*, pneumonia, cryptosporidiosis, histoplasmosis, toxoplasmosis, trypanosome infection and leishmaniasis.

Thus, the expression "diseases which are mediated by TLR agonists" means diseases which may be treated by activation of the immune system with TLR8 agonists such as cancer, autoimmune diseases, inflammation, sepsis, allergy, asthma, graft rejection, graft-versus-host disease, immunodeficiencies, and infectious diseases. In particular, the expression "diseases which are mediated by TLR agonists" means cancer, autoimmune diseases, inflammation, sepsis, allergy, asthma, graft rejection, graft-versus-host disease, immunodeficiencies, and infectious diseases.

In a particular aspect, the expression "which are mediated by TLR agonists" relates to cancer selected from the group consisting of bladder cancer, head and neck cancer, liver cancer, prostate cancer, colorectal cancer, kidney cancer, breast cancer, lung cancer, ovarian cancer, cervical cancer, pancreatic cancer, bowel and colon cancer, stomach cancer, thyroid cancer, melanoma, skin and brain tumors and malignancies affecting the bone marrow such as leukemias and lymphoproliferative systems, such as Hodgkin's and non-Hodgkin's lymphoma; including the prevention (e.g. vaccination) and treatment of metastatic cancer and tumor recurrences, and paraneoplastic syndromes.

The invention also relates to pharmaceutical compositions comprising a compound of formula I as defined above and a pharmaceutically acceptable carrier and/or adjuvant. More specifically, the invention relates to pharmaceutical compositions useful for the treatment of diseases which are which are mediated by TLR agonists.

Further, the invention relates to compounds of formula I as defined above for use as therapeutically active substances, particularly as therapeutically active substances for the treatment of diseases which are which are mediated by TLR agonists. In particular, the invention relates to compounds of formula I for use in the treatment of cancers or autoimmune diseases or infectious diseases selected from the group consisting of viral diseases, bacterial diseases, fungal diseases and parasitic diseases.

In another aspect, the invention relates to a method for the treatment a of diseases which are mediated by TLR agonists, which method comprises administering a therapeutically active amount of a compound of formula I to a human being or animal. In particular, the invention relates to a method for the treatment of cancers and infectious diseases selected from the group consisting of viral diseases, bacterial diseases, fungal diseases and parasitic diseases.

The invention further relates to the use of compounds of formula I as defined above for the treatment of diseases which are mediated by TLR agonists.

In addition, the invention relates to the use of compounds of formula I as defined above for the preparation of medicaments for the treatment of diseases which are mediated by TLR agonists. In particular, the invention relates to the use of compounds of formula I as defined above for the preparation of medicaments for the treatment of cancers or autoimmune diseases or infectious diseases selected from the group consisting of viral diseases, bacterial diseases, fungal diseases and parasitic diseases.

In a further aspect, compounds of formula I can be in combination with one or more additional treatment modalities in a regimen for the treatment of cancer.

Combination therapy encompasses, in addition to the administration of a compound of the invention, the adjunctive use of one or more modalities that are effective in the treatment of cancer. Such modalities include, but are not limited to, chemotherapeutic agents, immunotherapeutics, anti-angiogenic agents, cytokines, hormones, antibodies, polynucleotides, radiation and photodynamic therapeutic agents. In a specific aspect, combination therapy can be used to prevent the recurrence of cancer, inhibit metastasis, or inhibit the growth and/or spread of cancer or metastasis. As used herein, "in combination with" means that the compound of formula I is administered as part of a treatment regimen that comprises one or more additional treatment modalities as mentioned above. The invention thus also relates to a method for the treatment of cancer, which method comprises administering a therapeutically active amount of a compound of formula I in combination with one or more other pharmaceutically active compounds to a human being or animal.

Compounds of formula I can be used alone or in combination with one or more additional treatment modalities in treating autoimmune diseases.

Combination therapy encompasses, in addition to the administration of a compound of the invention, the adjunctive use of one or more modalities that aid in the prevention or treatment of autoimmune diseases. Such modalities include, but are not limited to, chemotherapeutic agents, immunotherapeutics, anti-angiogenic agents, cytokines, hormones, antibodies, polynucleotides, radiation and photodynamic therapeutic agents. As used herein, "in combination with" means that the compound of formula I is administered as part of a treatment regimen that comprises one or more additional treatment modalities as mentioned above. The invention thus also relates to a method for the treatment of autoimmune diseases, which method comprises administering a therapeutically active amount of a compound of formula I in combination with one or more other pharmaceutically active compounds to a human being or animal.

In a further aspect, compounds of formula I can be used alone or in combination with one or more additional treatment modalities in treating infectious diseases.

Combination therapy encompasses, in addition to the administration of a compound of the invention, the adjunctive use of one or more modalities that aid in the prevention or treatment of infectious diseases. Such modalities include, but are not limited to, antiviral agents, antibiotics, and anti-fungal agents. As used herein, "in combination with" means that the compound of formula I is administered as part of a treatment regimen that comprises one or more additional treatment modalities as mentioned above. The invention thus also relates to a method for the treatment of infectious diseases, which method comprises administering a therapeutically active amount of a compound of formula I in combination with one or more other pharmaceutically active compounds to a human being or animal.

Pharmacological Test

The following tests were carried out in order to determine the activity of the compounds of formula I:

For TLR8 and TLR7 activity testing, HEK-Blue human TLR8 or TLR7 cells (Invivogen, San Diego, Calif., USA) are used, respectively. These cells are designed for studying the stimulation of human TLR8 or TLR7 by monitoring the activation of NF-κB. A SEAP (secreted embryonic alkaline phosphatase) reporter gene is placed under the control of the IFN-b minimal promoter fused to five NF-κB and AP-1-binding sites. Therefore the reporter expression is regulated by the NF-κB promoter upon stimulation of human TLR8 or TLR7 for 20 hours. The cell culture supernatant SEAP reporter activity was determined using Quanti Blue kit (Invivogen, San Diego, Ca, USA) at a wavelength of 640 nm, a detection medium that turns purple/blue in the presence of alkaline phosphatase. $EC_{50}$ values were determined using Activity Base analysis (ID Business Solution, Limited).

The compounds according to formula I have an activity ($EC_{50}$ value) in the above assay for human TLR8 in the range of 0.01 nM to 0.05 µM, more particularly of 0.001 nM to 0.03 µM, whereas the activity ($EC_{50}$ value) in the above assay for human TLR7 is greater than 10 µM, in the range of 12 µM to >100 µM, meaning the compounds show high selectivity towards human TLR8.

For example, the following compounds showed the following $EC_{50}$ values in the assay described above:

| Example | human TLR8 $EC_{50}$ [µM] | human TLR7 $EC_{50}$ [µM] |
|---|---|---|
| 1 | 0.001 | 80.8 |
| 2 | 0.001 | >100 |
| 3 | 0.013 | 70.1 |
| 4 | 0.007 | >100 |
| 5 | 0.003 | >100 |
| 6 | 0.008 | >100 |
| 7 | 0.015 | >100 |
| 8 | 0.01 | 44 |
| 9 | 0.003 | >100 |
| 10 | 0.002 | >100 |
| 11 | 0.029 | >100 |
| 12 | 0.004 | >100 |
| 13 | 0.007 | >100 |
| 14 | 0.001 | >100 |
| 15 | 0.002 | >100 |
| 16 | 0.014 | >100 |
| 17 | 0.006 | >100 |
| 18 | 0.002 | 34 |
| 19 | 0.005 | >100 |
| 20 | 0.003 | 46 |
| 21 | 0.021 | >100 |
| 22 | 0.003 | >100 |
| 23 | 0.001 | >100 |
| 24 | 0.009 | >100 |
| 25 | 0.018 | >100 |
| 26 | 0.002 | >100 |
| 27 | 0.005 | 28 |
| 28 | 0.001 | >100 |
| 29 | 0.001 | >100 |
| 30 | 0.002 | >100 |
| 31 | 0.005 | >100 |
| 32 | 0.002 | >100 |
| 33 | 0.002 | >100 |
| 34 | 0.002 | >100 |
| 35 | 0.001 | >100 |
| 36 | 0.031 | >100 |
| 37 | 0.023 | 38 |
| 38 | 0.029 | 45 |
| 39 | 0.029 | >100 |
| 40 | 0.001 | >100 |
| 41 | 0.006 | >100 |

-continued

| Example | human TLR8 EC$_{50}$ [µM] | human TLR7 EC$_{50}$ [µM] |
|---|---|---|
| 42 | 0.017 | >100 |
| 43 | 0.015 | 61 |
| 44 | 0.001 | 12 |
| 45 | 0.026 | >100 |
| 46 | 0.01 | >100 |
| 47 | 0.006 | >100 |
| 48 | 0.016 | >100 |
| 49 | 0.031 | >100 |
| 50 | 0.01 | >100 |
| 51 | 0.002 | 22 |
| 52 | 0.006 | >100 |
| 53 | 0.002 | 20 |
| 54 | 0.003 | >100 |
| 55 | 0.002 | >100 |
| 56 | 0.01 | >100 |
| 57 | 0.025 | >100 |
| 58 | 0.015 | >100 |
| 59 | 0.003 | >100 |
| 60 | 0.027 | >100 |
| 61 | 0.005 | >100 |
| 62 | 0.007 | >100 |
| 63 | 0.011 | >100 |
| 64 | 0.029 | >100 |
| 65 | 0.006 | >100 |
| 66 | 0.031 | >100 |
| 67 | 0.004 | >100 |
| 68 | 0.008 | >100 |
| 69 | 0.008 | >100 |
| 70 | 0.012 | >100 |
| 71 | 0.029 | >100 |
| 72 | 0.025 | >100 |
| 73 | 0.01 | >100 |
| 74 | 0.027 | >100 |
| 75 | 0.01 | >100 |
| 76 | 0.024 | >100 |
| 77 | 0.008 | >100 |
| 78 | 0.012 | >100 |
| 79 | 0.002 | 31 |
| 80 | 0.017 | >100 |

Pharmaceutical Compositions

The compounds of formula I and their pharmaceutically acceptable salts can be used as medicaments, e.g., in the form of pharmaceutical preparations for enteral, parenteral or topical administration. The compounds of formula I and their pharmaceutically acceptable salts may be administered by systemic (e.g., parenteral) or local (e.g., topical or intralesional injection) administration. In some instances, the pharmaceutical formulation is topically, parenterally, orally, vaginally, intrauterine, intranasal, or by inhalation administered. As described herein, certain tissues may be preferred targets for the TLR agonist. Thus, administration of the TLR agonist to lymph nodes, spleen, bone marrow, blood, as well as tissue exposed to virus, are preferred sites of administration.

In one aspect, the pharmaceutical formulation comprising the compounds of formula or its pharmaceutically acceptable salts is administered parenterally. Parenteral routes of administration include, but are not limited to, transdermal, transmucosal, nasopharyngeal, pulmonary and direct injection. Parenteral administration by injection may be by any parenteral injection route, including, but not limited to, intravenous (IV), including bolus and infusion (e.g., fast or slow), intraperitoneal (IP), intramuscular (IM), subcutaneous (SC) and intradermal (ID) routes. Transdermal and transmucosal administration may be accomplished by, for example, inclusion of a carrier (e.g., dimethylsulfoxide, DMSO), by application of electrical impulses iontophoresis) or a combination thereof. A variety of devices are available for transdermal administration which may be used. Formulations of the compounds of formula I suitable for parenteral administration are generally formulated in USP water or water for injection and may further comprise pH buffers, salts bulking agents, preservatives, and other pharmaceutically acceptable excipients.

Transdermal administration is accomplished by application of a cream, rinse, gel, etc. capable of allowing the TLR agonist to penetrate the skin and enter the blood stream. Compositions suitable for transdermal administration include, but are not limited to, pharmaceutically acceptable suspensions, oils, creams and ointments applied directly to the skin or incorporated into a protective carrier such as a transdermal device so-called "patch"). Examples of suitable creams, ointments etc. can be found, for instance, in the Physician's Desk Reference. Transdermal transmission may also be accomplished by iontophoresis, for example using commercially available patches which deliver their product continuously through unbroken skin for periods of several days or more. Use of this method allows for controlled transmission of pharmaceutical compositions in relatively great concentrations, permits infusion of combination drugs and allows for contemporaneous use of an absorption promoter, Administration via the transdermal and transmucosal routes may be continuous or pulsatile.

Pulmonary administration is accomplished by inhalation, and includes delivery routes such as intranasal, transbronchial and transalveolar routes. Formulations of compounds of formula I suitable for administration by inhalation including, but not limited to, liquid suspensions for forming aerosols as well as powder forms for dry powder inhalation delivery systems are provided. Devices suitable for administration by inhalation include, but are not limited to, atomizers, vaporizers, nebulizers, and dry powder inhalation delivery devices. Other methods of delivering to respiratory mucosa include delivery of liquid formulations, such as by nose drops. Administration by inhalation is preferably accomplished in discrete doses (e.g., via a metered dose inhaler), although delivery similar to an infusion may be accomplished through use of a nebulizer.

The compounds of formula I and pharmaceutically acceptable salts thereof may also be administered orally, e.g., in the form of tablets, coated tablets, dragées, hard and soft gelatine capsules.

The production of the pharmaceutical preparations can be effected in a manner which will be familiar to any person skilled in the art by bringing the described compounds of formula I and their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 to 1000 mg, especially about 1 to 300 mg, comes into consideration. Depending on severity of the disease and the precise pharmacokinetic profile the compound could be administered with one or several daily dosage units, e.g., in 1 to 3 dosage units.

The pharmaceutical preparations conveniently contain about 1-500 mg, preferably 1-100 mg, of a compound of formula I.

The following examples C1 to C3 illustrate typical compositions of the present invention, but serve merely as representative thereof.

Example C1

Film coated tablets containing the following ingredients can be manufactured in a conventional manner:

| Ingredients | Per tablet | |
| --- | --- | --- |
| Kernel: | | |
| Compound of formula I | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titanium dioxide | 0.8 mg | 1.6 mg |

The active ingredient is sieved and mixed with microcrystalline cellulose and the mixture is granulated with a solution of polyvinylpyrrolidone in water. The granulate is mixed with sodium starch glycolate and magnesium stearate and compressed to yield kernels of 120 or 350 mg respectively. The kernels are lacquered with an aqueous solution/suspension of the above mentioned film coat.

Example C2

Capsules containing the following ingredients can be manufactured in a conventional manner:

| Ingredients | Per capsule |
| --- | --- |
| Compound of formula I | 25.0 mg |
| Lactose | 150.0 mg |
| Maize starch | 20.0 mg |
| Talc | 5.0 mg |

The components are sieved and mixed and filled into capsules of size 2.

Example C3

Injection solutions can have the following composition:

| Ingredients | |
| --- | --- |
| Compound of formula I | 3.0 mg |
| Polyethylene glycol 400 | 150.0 mg |
| Acetic acid | q.s. ad pH 5.0 |
| Water for injection solutions | ad 1.0 ml |

The active ingredient is dissolved in a mixture of Polyethylene Glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

The following examples serve to illustrate the present invention in more detail. They are, however, not intended to limit its scope in any manner.

EXAMPLES

Abbreviations used therein:

$Boc_2O$=di-tert-butyl dicarbonate, Boc=t-butyl carbamate, calc'd=calculated, $CD_3OD$=deuterated methanol, d=day, DIPEA=N,N-diisopropylethylamine, DCM=dichloromethane, DMAP: 4-dimethylaminopyridine, DMF-DMA: N,N-dimethylformamide dimethyl acetal, EA=ethyl acetate or EtOAc, $EC_{50}$=half maximal effective concentration, EDCI=1-(3-dimethylaminopropyl)-3-ethyl-carbodiimide hydrochloride, h or hr=hour, HOBT=N-hydroxybenzotriazole, HBTU=O-(benzotriazol-1-yl)-N,N,N',N'-tetramethyluronium hexafluorophosphate, DMAP=4-dimethylaminopyridine, TBAI=N,N,N-tributyl-1-butanaminiuiodide, HPLC=high performance liquid chromatography, HPLC-UV=high performance liquid chromatography with ultraviolet detector, Hz=hertz, mg=milligram, MHz=megahertz, min=minute(s), mL=milliliter, mm=millimeter, mM=mmol/L, mmol=millimole, MS=mass spectrometry, MW=molecular weight, NMR=nuclear magnetic resonance, PE=petroleum ether, prep-HPLC=preparative high performance liquid chromatography, rt=room temperature, sat.=sat., TBS=tert-butyldimethylsilyl, sxt=sextet, TEA=triethylamine, TFA=trifluoroacetic acid, THF=tetrahydrofuran, µM=micromole/L, µm=micrometer, UV=ultraviolet detector, OD=optical density, $Pd(dppf)_2Cl_2$=[1,1'-Bis(diphenylphosphino)-ferrocene]dichloropalladium(II), TLR8=toll-like receptor 8, TLR7=toll-like receptor 7, NFκB=nuclear factor kappa-light-chain-enhancer of activated B cells, SEAP=secreted embryonic alkaline phosphatase, IFN-β=interferon-beta.

Example A

Preparation of Key Intermediate a

2-Amino-8-methoxycarbonyl-3H-1-benzazepine-4-carboxylic acid

A detailed synthetic route is provided in Scheme 2.

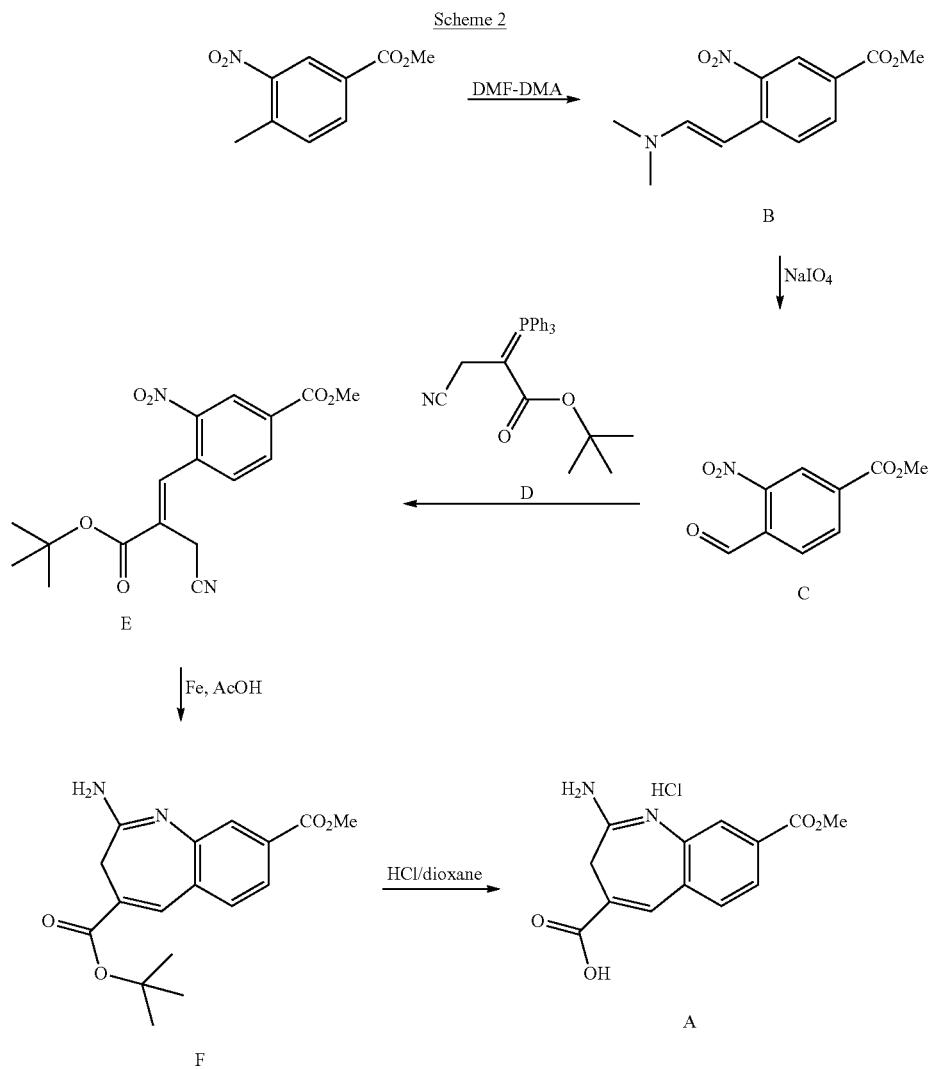

a) Preparation of Compound B

To a solution of methyl 4-methyl-3-nitrobenzoate (100 g, 0.51 mol) in DMF (1 L) was added DMF-DMA (73 g, 0.61 mol). The reaction mixture was heated to 105° C. for 18 hrs. Then the solvent was removed in vacuo to give methyl 4-(2-(dimethylamino)vinyl)-3-nitrobenzoate (compound B, 127 g, crude) which was used in the next step without purification. MS: calc'd 251 $(M+H)^+$. measured 251 $(M+H)^+$.

b) Preparation of Compound C

To a solution of $NaIO_4$ (327 g, 1.53 mol) in a mixed solvent of THF (1.3 L) and water (2.0 L) was added a THF (0.7 L) solution of methyl 4-(2-(dimethylamino)vinyl)-3-nitrobenzoate (compound A, 127 g, 0.51 mol) at 10° C. After the reaction mixture was stirred at 25° C. for 18 hrs, the mixture was filtered and then extracted with EA. The organic layer was washed with brine, dried over anhydrous $Na_2SO_4$, filtered and concentrated to give the crude product. The crude product was purified by silica gel column chromatography (PE:EA=20:1-10:1) to give methyl 4-formyl-3-nitrobenzoate (compound C, 84 g, 79%) as a yellow solid. MS: calc'd 210 $(M+H)^+$. measured 210 $(M+H)^+$.

c) Preparation of Compound D

To a solution of tert-butyl 2-(triphenylphosphoranylidene)acetate (300 g, 0.797 mol) in EA (2 L) was added 2-bromoacetonitrile (57 g, 0.479 mol) at 25° C. The reaction was heated to reflux for 18 hrs. After it was cooled to ambient temperature, the solid was filtered and the filtrate was concentrated. The residue was purified by triturating from EA and PE (200 mL, 2.5:1) to give the desired product tert-butyl 3-cyano-2-(triphenylphosphoranylidene)propanoate (compound D, 125 g, 63%) as a white solid. MS: calc'd 416 (M+H)⁺. measured 416 (M+H)⁺.

d) Preparation of Compound E

To a solution of 4-formyl-3-nitrobenzoate (compound C, 50 g, 0.24 mol) in toluene (600 mL) was added tert-butyl 3-cyano-2-(triphenylphosphoranylidene)propanoate (compound D, 109 g, 0.26 mol) at 25° C. After the reaction mixture was stirred at 25° C. for 18 hrs, it was cooled in ice-bath for 1 hr. The precipitate was collected and dried to give the desired product as a white solid. The filtrate was concentrated and treated with EtOH (120 mL). The undissolved material was filtered and the filtrate was concentrated to give an additional batch of the desired product. These two batches were combined to give methyl 4-(3-(tert-butoxy)-2-(cyanomethyl)-3-oxoprop-1-en-1-yl)-3-nitrobenzoate (compound E, 60 g, 72%). MS: calc'd 347 (M+H)⁺. measured 347 (M+H)⁺.

e) Preparation of Compound F

To a solution of methyl 4-(3-(tert-butoxy)-2-(cyanomethyl)-3-oxoprop-1-en-1-yl)-3-nitrobenzoate (compound E, 30 g, 87 mmol) in AcOH (450 mL) was added Fe powder (29.1 g, 520 mmol) at 60° C. After the reaction mixture was heated at 85° C. for 3 hrs, it was filtered through celite and the precipitate was washed with acetic acid. The filtrate was concentrated in vacuo and the residue was carefully basified with aqueous sat. NaHCO₃ solution (300 mL). Then EA (600 mL) was added. The mixture was filtered through celite and the precipitate was washed with EA (200 mL). The filtrate was then washed with water, dried over Na₂SO₄ and concentrated in vacuo to get 4-tert-butyl 8-methyl 2-amino-3H-benzo[b]azepine-4,8-dicarboxylate (compound F, 25 g, 93%) as a light yellow solid. MS: calc'd 317 (M+H)⁺. measured 317 (M+H)⁺.

f) Preparation of Compound A

To a solution of 4-tert-butyl 8-methyl 2-amino-3H-benzo[b]azepine-4,8-dicarboxylate (compound F, 25 g, 80 mmol) in dioxane (400 mL) was added a 1 M solution of HCl in dioxane (600 mL) at 0° C. After the reaction mixture was stirred at 25° C. for 18 hrs, it was concentrated in vacuo to give 2-amino-8-(methoxycarbonyl)-3H-benzo[b]azepine-4-carboxylic acid hydrochloride (compound A, 25 g, crude) which was used in the next step without any purification. MS: calc'd 261 (M+H)⁺. measured 261 (M+H)⁺.

Example B

Preparation of Key Intermediate J 2-(tert-butoxycarbonylamino)-4-(dipropylcarbamoyl)-3H-1-benzazepine-8-carboxylic acid A detailed synthetic route is provided in Scheme 3.

g) Preparation of Compound G

To a mixture of 2-amino-8-(methoxycarbonyl)-3H-benzo[b]azepine-4-carboxylic acid hydrochloride (compound A, 19 g, 64 mmol), HBTU (29 g, 77 mmol), DIPEA (33 g, 257 mmol) in DMF (400 mL) was added di-n-propylamine (13 g, 128 mmol) at 0° C. After the reaction mixture was stirred for 2 hrs at 20° C., it was quenched with sat. NH₄Cl (500 mL), diluted with H₂O (1 L), and extracted with EA (300 mL×3). The combined organic layers were washed with brine (300 mL×2), dried over Na₂SO₄ and concentrated to give the crude product. The crude product was purified by silica gel silica gel column chromatography (PE:EA=1:1) to give methyl 2-amino-4-(dipropylcarbamoyl)-3H-benzo[b]azepine-8-carboxylate (compound G, 18 g, 82%) as a yellow solid. MS: calc'd 344 (M+H)⁺. measured 344 (M+H)⁺.

Scheme 3

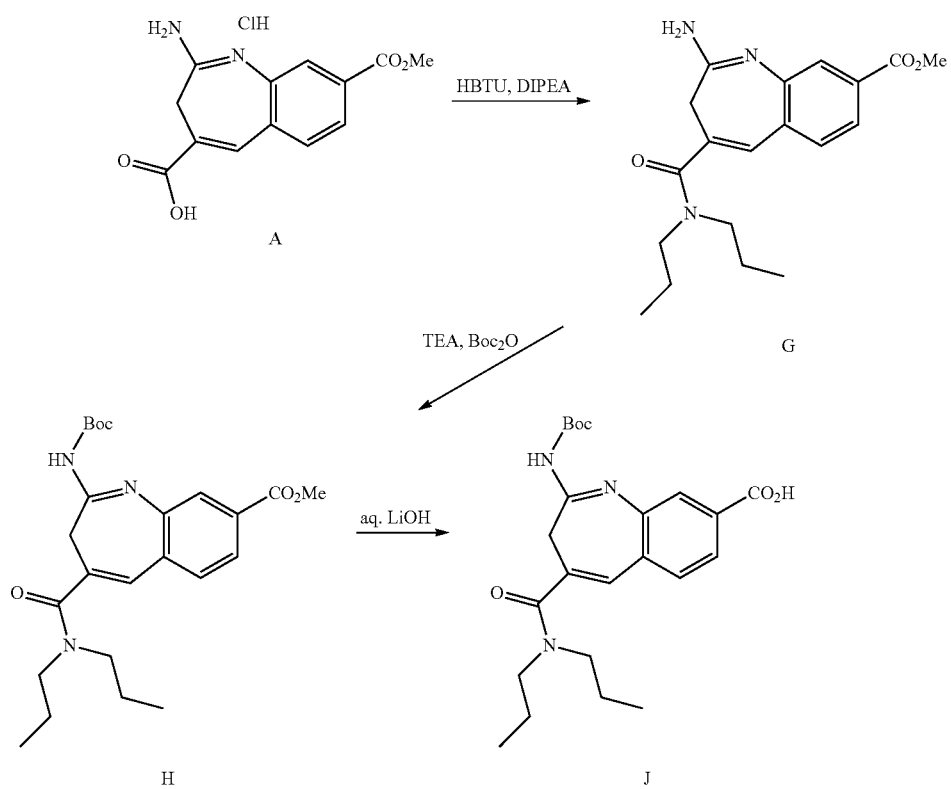

h) Preparation of Compound H

To a mixture of methyl 2-amino-4-(dipropylcarbamoyl)-3H-benzo[b]azepine-8-carboxylate (compound G, 18 g, 53 mmol) and TEA (16 g, 157 mmol) in DCM (300 mL) was added Boc$_2$O (17 g, 79 mmol) at 0° C. After the mixture was stirred for 16 hrs at 20° C., it was quenched with sat. NH$_4$Cl (300 mL), diluted with H$_2$O (500 mL), and extracted with DCM (100 mL×3). The combined organic layers were washed with brine (100 mL×2), dried over Na$_2$SO$_4$ and concentrated to give the crude product. The crude product was purified by silica gel column chromatography (PE:EA=3:1) to give methyl 2-((tert-butoxycarbonyl)amino)-4-(dipropylcarbamoyl)-3H-benzo[b]azepine-8-carboxylate (compound H, 21 g, yield: 91%) as a yellow solid. MS: calc'd 444 (M+H)$^+$. measured 444 (M+H)$^+$.

i) Preparation of Compound J

To a solution of methyl 2-((tert-butoxycarbonyl)amino)-4-(dipropylcarbamoyl)-3H-benzo[b]azepine-8-carboxylate (compound H, 5.0 g, 11.3 mmol) in THF/H$_2$O (1/1, 100 mL) was added aq. LiOH solution (1 M, 17 mL, 17 mmol) at 0° C. Then the mixture was warmed to 25° C. and stirred for 6 hrs. The mixture was poured into ice-water (150 mL), acidified with aq. citric acid (5%) to pH=5 and extracted with EtOAc (100 mL×3). The combined organic layers were washed with brine (100 mL×2), dried over Na$_2$SO$_4$ and concentrated in vacuo to give 2-(tert-butoxycarbonylamino)-4-(dipropylcarbamoyl)-3H-1-benzazepine-8-carboxylic acid (compound J, 4.0 g, 83.3%) as a yellow solid. $^1$H NMR (400 MHz, DMSO-d6) δ ppm=7.78-7.72 (m, 1H), 7.64 (dd, J=1.5, 8.0 Hz, 1H), 7.55 (d, J=8.3 Hz, 1H), 6.93-6.89 (m, 1H), 3.14 (s, 6H), 1.54 (br. s., 4H), 1.44 (s, 9H), 0.80 (br. s., 6H). MS: calc'd 430 (M+H)$^+$. measured 430 (M+H)$^+$.

Example 1

2-Amino-N4,N4-dipropyl-N8-(3-pyridyl)-3H-1-benzazepine-4,8-dicarboxamide

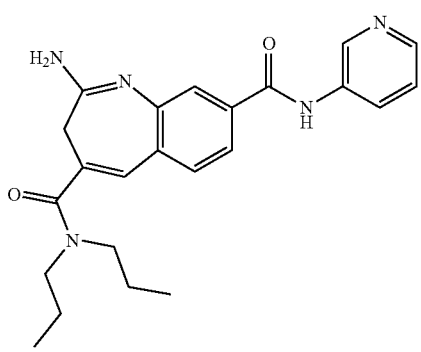 [SMILES: CCCN(CCC)C(=O)C1=Cc2ccc(C(=O)Nc3cccnc3)cc2N=C(N)C1]

Example 1 can be prepared according to general procedure in scheme 1. A detailed synthetic route is provided in Scheme 4.

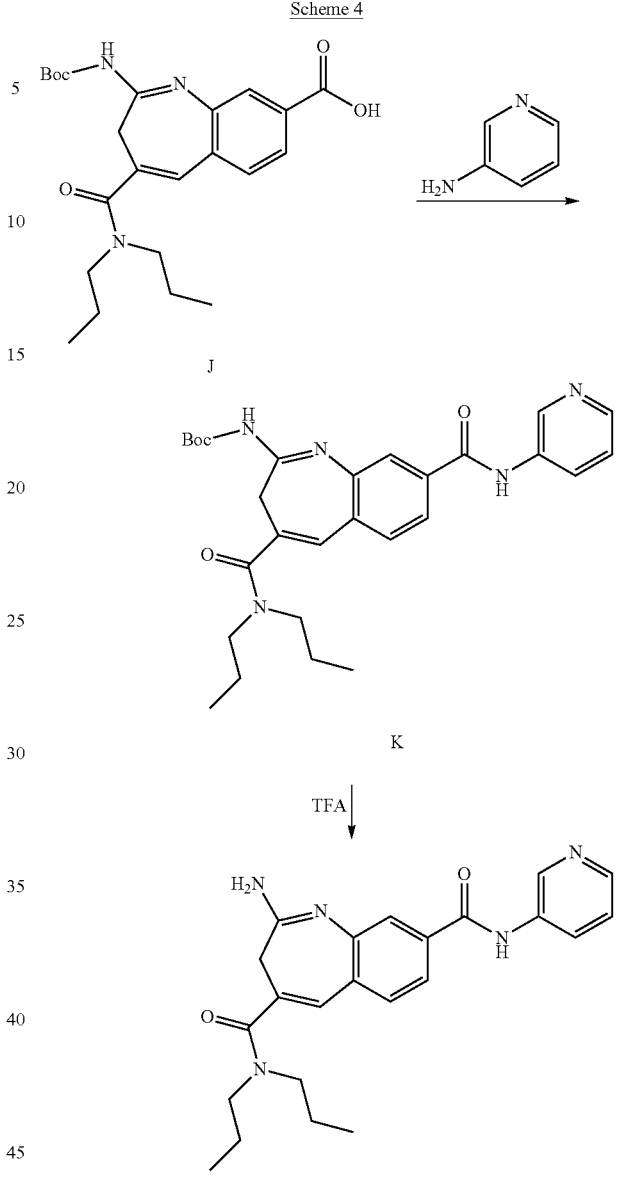

Scheme 4

Preparation of Example 1

To a solution of 2-(tert-butoxycarbonylamino)-4-(dipropylcarbamoyl)-3H-1-benzazepine-8-carboxylic acid (compound J, 80 mg, 0.186 mmol) in DCM (4 mL) was added EDCI (49 mg, 0.466 mmol), HOBT (19.6 mg, 0.220 mmol), DIPEA (96 mg, 0.744 mmol) and DMAP (6 mg, 0.046 mmol) at 10° C. After the reaction was stirred for 30 minutes at 25° C., pyridin-3-amine (27 mg, 0.280 mmol) was added and the reaction mixture was stirred overnight. Water (2 mL) was added and the mixture was extracted with DCM (10 mL). The organic layer was washed successively with 5% citric acid, sat NaHCO$_3$, and concentrated to give the crude product K (70 mg), which was dissolved in DCM (1.5 mL). To this DCM solution was added a solution of TFA (566 mg, 4.9 mmol) in DCM (0.5 mL) at 0° C. After the reaction mixture was stirred at 20° C. for 4 hrs, it was concentrated and the residue was basified to pH 8 with sat.NaHCO$_3$. The aqueous layer was extracted with DCM, dried over Na$_2$SO$_4$ and concentrated in vacuo to give the crude product that was purified by prep-HPLC to give 2-amino-N4,N4-dipropyl-N8-(3-pyridyl)-3H-1-benzazepine-4,8-dicarboxamide (Example 1, 6.7 mg) as a white solid. $^1$H NMR (300 MHz, CDCl$_3$) δ ppm=8.64 (d, J=2.3 Hz, 1H), 8.32 (d, J=3.8 Hz, 1H), 8.29-8.14 (m, 2H), 7.62 (s, 1H), 7.56 (d, J=7.9 Hz, 1H), 7.33 (d, J=8.3 Hz, 1H), 7.26 (dd, J=4.9, 8.3 Hz, 1H), 6.75 (s, 1H), 3.41 (d, J=9.8 Hz, 4H), 2.74 (s, 2H), 1.63-1.56 (m, 4H), 0.86 (t, J=7.2 Hz, 6H). MS: calc'd 406 (M+H)$^+$. measured 406 (M+H)$^+$.

Example 2

2-Amino-N4,N4-dipropyl-N8-pyrimidin-5-yl-3H-1-benzazepine-4,8-dicarboxamide

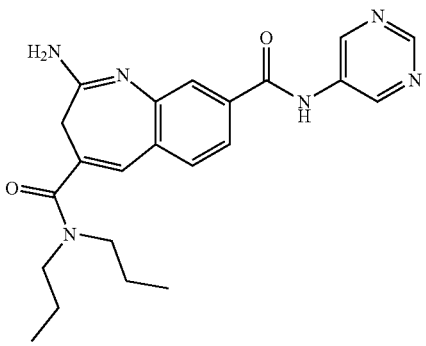 [SMILES: CCCN(CCC)C(=O)C1=Cc2ccc(C(=O)Nc3cncnc3)cc2N=C(N)C1]

The title compound was prepared in analogy to Example 1 by using pyrimidin-5-amine instead of pyridin-3-amine. Example 2 was obtained as a white solid (5.1 mg). $^1$H NMR (400 MHz, CDCl$_3$) δ ppm=9.18 (s, 2H), 9.03-8.95 (m, 1H), 8.71-8.54 (m, 1H), 7.80-7.62 (m, 2H), 7.45-7.37 (m, 1H), 6.85-6.76 (m, 1H), 3.58-3.37 (m, 4H), 2.94-2.82 (m, 2H), 2.02-1.86 (m, 4H), 0.95 (br. s., 6H). MS: calc'd 407 (M+H)$^+$. measured 407 (M+H)$^+$.

Example 3

2-Amino-N4,N4-dipropyl-N8-(4-pyridyl)-3H-1-benzazepine-4,8-dicarboxamide

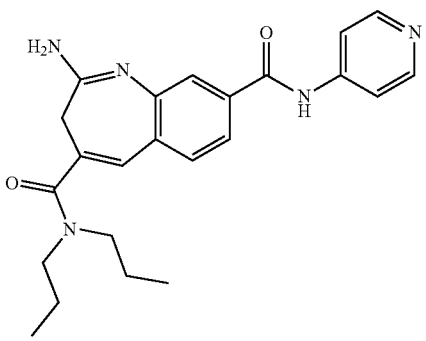 [SMILES: CCCN(CCC)C(=O)C1=Cc2ccc(C(=O)Nc3ccncc3)cc2N=C(N)C1]

The title compound was prepared in analogy to Example 1 by using pyridin-4-amine instead of pyridin-3-amine. Example 3 was obtained as a yellow solid (15 mg). $^1$H NMR (400 MHz, DMSO-d$_6$) δ ppm=12.02-11.94 (m, 1H), 10.09-10.00 (m, 1H), 9.24-9.16 (m, 1H), 8.85-8.75 (m, 2H), 8.48-8.40 (m, 2H), 8.17-8.10 (m, 1H), 8.08-8.03 (m, 1H), 7.82-7.73 (m, 1H), 7.09 (s, 1H), 3.38 (br. s., 6H), 1.59 (d, J=7.0 Hz, 4H), 1.03-0.67 (m, 6H). MS: calc'd 406 (M+H)$^+$. measured 406 (M+H)$^+$.

Example 4

2-Amino-N8-phenyl-N4,N4-dipropyl-3H-1-benzazepine-4,8-dicarboxamide

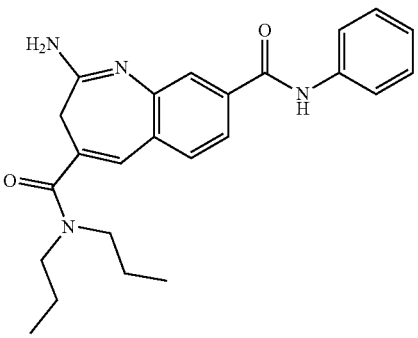 [SMILES: CCCN(CCC)C(=O)C1=Cc2ccc(C(=O)Nc3ccccc3)cc2N=C(N)C1]

The title compound was prepared in analogy to Example 1 by using aniline instead of pyridin-3-amine. Example 4 was obtained as a white solid (30 mg). $^1$H NMR (300 MHz, DMSO-d$_6$) δ ppm=10.49-10.40 (m, 1H), 9.96-9.87 (m, 1H), 9.09-8.97 (m, 1H), 8.03-7.91 (m, 2H), 7.82-7.67 (m, 3H), 7.43-7.32 (m, 2H), 7.20-7.09 (m, 1H), 7.09-7.02 (m, 1H), 3.31-3.14 (m, 6H), 1.69-1.45 (m, 4H), 1.04-0.69 (m, 6H). MS: calc'd 405 (M+H)$^+$. measured 405 (M+H)$^+$.

Example 5

2-Amino-N8-[6-(aminomethyl)-3-pyridyl]-N4,N4-dipropyl-3H-1-benzazepine-4,8-dicarboxamide

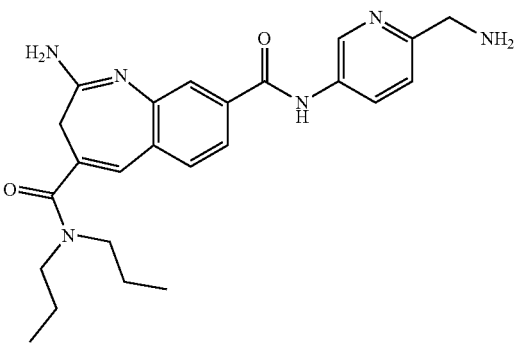 [SMILES: CCCN(CCC)C(=O)C1=Cc2ccc(C(=O)Nc3ccc(CN)nc3)cc2N=C(N)C1]

The title compound was prepared in analogy to Example 1 by using tert-butyl ((5-aminopyridin-2-yl)methyl)carbamate instead of pyridin-3-amine. Example 5 was obtained as a gray gum (17 mg). $^1$H NMR (400 MHz, DMSO-d$_6$) δ ppm=10.05 (br. s., 1H), 9.22 (s, 1H), 9.07 (d, J=2.01 Hz, 1H), 8.46 (br. s., 3H), 8.30 (dd, J=2.26, 8.53 Hz, 1H), 8.07 (d, J=8.16 Hz, 1H), 8.02 (s, 1H), 7.74 (d, J=8.28 Hz, 1H), 7.56 (d, J=8.66 Hz, 1H), 7.06 (s, 1H), 4.18 (d, J 5.65 Hz, 2H), 3.29-3.39 (m, 6H), 1.52-1.65 (m, 4H), 0.74-0.98 (m, 6H). MS: calc'd 435 (M+H)$^+$. measured 435 (M+H)$^+$.

Example 6

2-Amino-N8-[5-(hydroxymethyl)-3-pyridyl]-N4,N4-dipropyl-3H-1-benzazepine-4,8-dicarboxamide

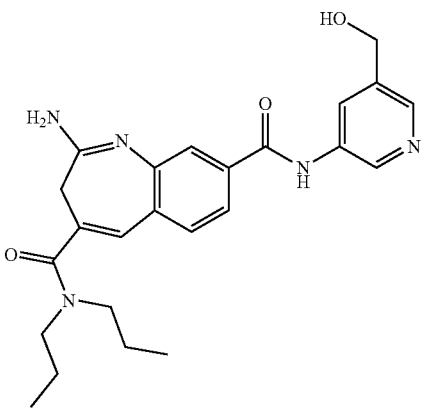 [SMILES: CCCN(CCC)C(=O)C1=Cc2ccc(C(=O)Nc3cncc(CO)c3)cc2N=C(N)C1]

The title compound was prepared in analogy to Example 1 by using 5-(((tert-butyldimethylsilyl)oxy)methyl)pyridin-3-amine (Compound 6A) instead of pyridin-3-amine. Example 6 was obtained as a yellow gum (9.6 mg). $^1$H NMR (400 MHz, CD$_3$OD) δ ppm=9.55-9.47 (m, 1H), 8.85-8.78 (m, 1H), 8.63-8.58 (m, 1H), 8.14-8.04 (m, 2H), 7.81-7.73 (m, 1H), 7.17-7.12 (m, 1H), 4.87-4.78 (m, 2H), 3.56-3.38 (m, 6H), 1.79-1.64 (m, 4H), 1.10-0.86 (m, 6H). MS: calc'd 436 (M+H)$^+$. measured 436 (M+H)$^+$.

Preparation of 5-(((tert-butyldimethylsilyl)oxy)methyl)pyridin-3-amine (Compound 6A)

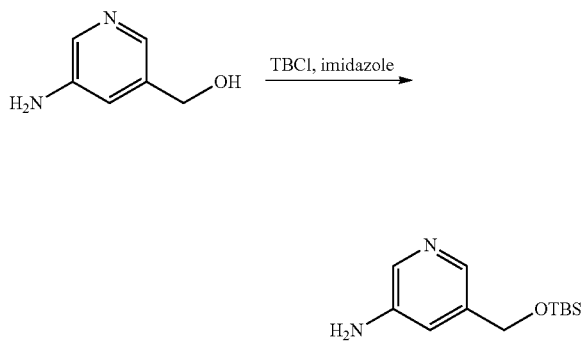

To a mixture of (5-aminopyridin-3-yl)methanol (100 mg, 0.8 mmol) and imidazole (160 mg, 2.4 mmol) in DMF (3 mL) was added TBSCl (145 mg, 1.0 mmol) at 0° C. After the reaction mixture was stirred at 20° C. for 16 hrs, water (10 mL) was added and the mixture was extracted with EA (3 mL×3). The combined organic layers were washed with sat. NH$_4$Cl, brine, dried over Na$_2$SO$_4$ and concentrated to give 5-(((tert-butyldimethylsilyl)oxy)methyl)pyridin-3-amine (compound 6A) (110 mg) which was used in the next step without any purification. MS: calc'd 239 (M+H)$^+$. measured 239 (M+H)$^+$.

Example 7

2-Amino-N8-[6-(hydroxymethyl)-3-pyridyl]-N4,N4-dipropyl-3H-1-benzazepine-4,8-dicarboxamide

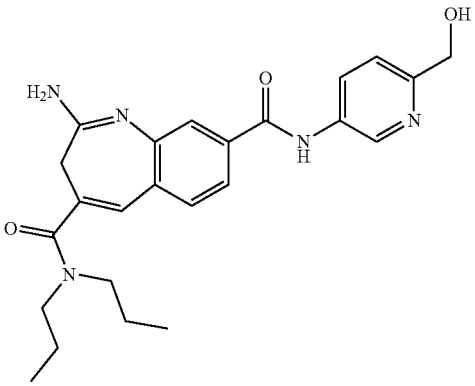 [SMILES: CCCN(CCC)C(=O)C1=Cc2ccc(C(=O)Nc3ccc(CO)nc3)cc2N=C(N)C1]

The title compound was prepared in analogy to Example 6 by using (5-aminopyridin-2-yl)methanol instead of (5-aminopyridin-3-yl)methanol. Example 7 was obtained as a yellow gum (17 mg). $^1$H NMR (400 MHz, CD$_3$OD) δ ppm=9.53 (s, 1H), 8.82 (d, J=8.78 Hz, 1H), 8.13 (s, 1H), 8.09 (d, J=8.16 Hz, 1H), 8.02 (d, J=8.78 Hz, 1H), 7.76 (d, J=8.16 Hz, 1H), 7.14 (s, 1H), 5.01 (s, 2H), 3.49 (br. s., 4H), 3.42 (s, 2H), 1.72 (sxt, J=7.38 Hz, 4H), 0.97 (dd, J=7.34, 14.87 Hz, 6H). MS: calc'd 436 (M+H)$^+$. measured 436 (M+H)$^+$.

Example 8

2-Amino-N8-(3-methylsulfonylphenyl)-N4,N4-dipropyl-3H-1-benzazepine-4,8-dicarboxamide

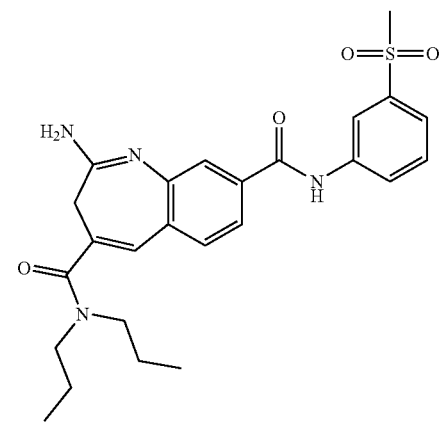 [SMILES: CCCN(CCC)C(=O)C1=Cc2ccc(C(=O)Nc3cccc(S(C)(=O)=O)c3)cc2N=C(N)C1]

The title compound was prepared in analogy to Example 1 by using 3-(methylsulfonyl)-aniline instead of pyridin-3-amine. Example 8 was obtained as a yellow solid (12.1 mg). $^1$H NMR (400 MHz, CD$_3$OD) δ ppm=8.52-8.44 (m, 1H), 8.10-8.04 (m, 1H), 8.04-7.98 (m, 2H), 7.81-7.63 (m, 3H), 7.14 (s, 1H), 3.49 (br. s., 4H), 3.42-3.37 (m, 2H), 3.18 (s, 3H), 1.72 (m, 4H), 0.99 (br. s., 6H). MS: calc'd 483 (M+H)$^+$. measured 483 (M+H)$^+$.

Example 9

2-Amino-N4,N4-dipropyl-N8-thiazol-5-yl-3H-1-benzazepine-4,8-dicarboxamide

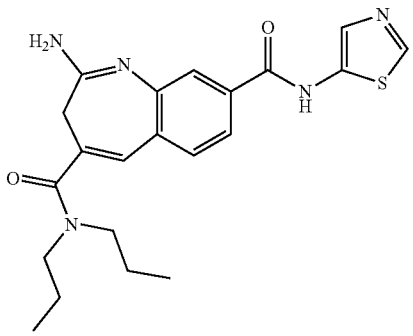 [SMILES: CCCN(CCC)C(=O)C1=Cc2ccc(C(=O)Nc3cncs3)cc2N=C(N)C1]

The title compound was prepared in analogy to Example 1 by using thiazol-5-amine instead of pyridin-3-amine. Example 9 was obtained as a yellow solid (17.4 mg). $^1$H NMR (300 MHz, DMSO-d$_6$) δ ppm=12.16-12.07 (m, 1H), 10.02-9.92 (m, 1H), 9.16-9.05 (m, 1H), 8.73-8.67 (m, 1H), 8.09-7.97 (m, 2H), 7.94-7.87 (m, 1H), 7.79-7.70 (m, 1H), 7.10-7.00 (m, 1H), 3.42-3.25 (m, 6H), 1.67-1.48 (m, 4H), 1.00-0.70 (m, 6H). MS: calc'd 412 (M+H)$^+$. measured 412 (M+H)$^+$.

Example 10

2-Amino-N8-(4-chlorophenyl)-N4,N4-dipropyl-3H-1-benzazepine-4,8-dicarboxamide

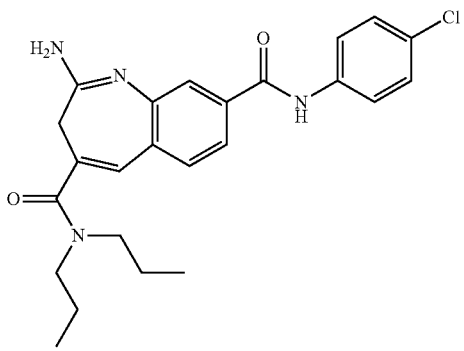 [SMILES: CCCN(CCC)C(=O)C1=Cc2ccc(C(=O)Nc3ccc(Cl)cc3)cc2N=C(N)C1]

The title compound was prepared in analogy to Example 1 by using 4-chloroaniline instead of pyridin-3-amine. Example 10 was obtained as a yellow solid (14.8 mg). $^1$H NMR (400 MHz, CD$_3$OD) δ ppm=7.94-8.00 (m, 2H), 7.69-7.78 (m, 3H), 7.37-7.43 (m, 2H), 7.13 (s, 1H), 3.50 (br. s., 4H), 3.34 (s, 2H), 1.72 (sxt, J=7.50 Hz, 4H), 0.98 (br. s., 6H). MS: calc'd 439 (M+H)$^+$. measured 439 (M+H)$^+$

Example 11

2-Amino-N4,N4-dipropyl-N8-thiazol-2-yl-3H-1-benzazepine-4,8-dicarboxamide

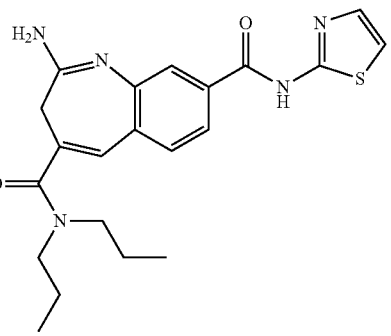

The title compound was prepared in analogy to Example 1 by using thiazol-2-amine instead of pyridin-3-amine. Example 11 was obtained as a white solid (44 mg). $^1$H NMR (400 MHz, METHANOL-d$_4$) δ ppm=7.91 (s, 1H), 7.87 (d, J=8 Hz, 1H), 7.60 (d, J=8 Hz, 1H), 7.50 (d, J=4 Hz, 1H), 7.18 (d, J=4 Hz, 1H), 7.01 (s, 1H), 4.94 (m, 2H), 3.44 (m, 4H), 1.71-1.65 (m, 4H), 0.96-0.89 (m, 6H). MS: calc'd 412 (M+H)$^+$. measured 412 (M+H)$^+$.

Example 12

2-Amino-N8-(3-methylimidazol-4-yl)-N4,N4-dipropyl-3H-1-benzazepine-4,8-dicarboxamide

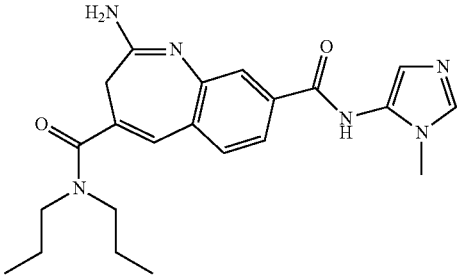 [SMILES: CCCN(CCC)C(=O)C1=Cc2ccc(C(=O)Nc3cncn3C)cc2N=C(N)C1]

The title compound was prepared in analogy to Example 1 by using 1-methyl-1H-imidazol-5-amine instead of pyridin-3-amine. Example 12 was obtained as a yellow solid (12 mg). $^1$H NMR (300 MHz, CD$_3$OD) δ ppm=8.99-8.92 (m, 1H), 8.12-8.00 (m, 2H), 7.79-7.72 (m, 1H), 7.71-7.65 (m, 1H), 7.17-7.09 (m, 1H), 3.96-3.84 (m, 3H), 3.58-3.37 (m, 6H), 1.83-1.62 (m, 4H), 1.09-0.86 (m, 6H). MS: calc'd 409 (M+H)$^+$. measured 409 (M+H)$^+$.

Example 13

2-Amino-N8-(4-fluorophenyl)-N4,N4-dipropyl-3H-1-benzazepine-4,8-dicarboxamide

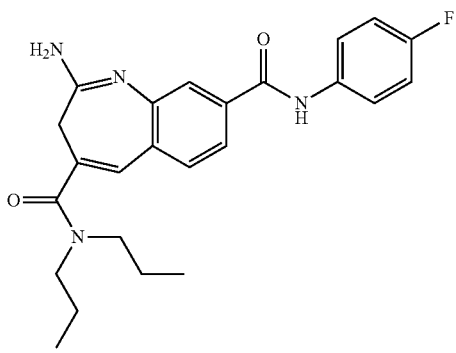 [SMILES: CCCN(CCC)C(=O)C1=Cc2ccc(C(=O)Nc3ccc(F)cc3)cc2N=C(N)C1]

The title compound was prepared in analogy to Example 1 by using 4-fluoroaniline instead of pyridin-3-amine. Example 13 was obtained as a yellow solid (22 mg). $^1$H NMR (400 MHz, CD$_3$OD) δ ppm=7.94-8.01 (m, 2H), 7.67-7.79 (m, 3H), 7.09-7.21 (m, 3H), 3.49 (br. s., 4H), 3.33-3.35 (m, 2H), 1.72 (sxt, J=7.48 Hz, 4H), 0.97 (br. s., 6H). MS: calc'd 423 (M+H)$^+$. measured 423 (M+H)$^+$.

Example 14

2-Amino-N8-(m-tolyl)-N4,N4-dipropyl-3H-1-benzazepine-4,8-dicarboxamide

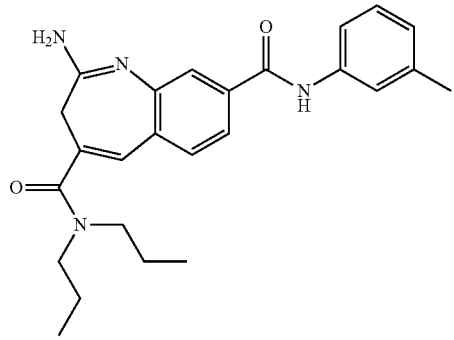 [SMILES: CCCN(CCC)C(=O)C1=Cc2ccc(C(=O)Nc3cccc(C)c3)cc2N=C(N)C1]

The title compound was prepared in analogy to Example 1 by using m-toluidine instead of pyridin-3-amine. Example 14 was obtained as a white solid (38 mg). $^1$H NMR (400 MHz, CD$_3$OD) δ ppm=7.93-8.01 (m, 2H), 7.67-7.74 (m, 1H), 7.49-7.59 (m, 2H), 7.28 (t J=7.84 Hz, 1H), 7.12 (s, 1H), 7.03 (d, J=7.65 Hz, 1H), 3.49 (br. s., 4H), 3.39 (s, 2H), 2.39 (s, 3H), 1.72 (sxt, J=7.45 Hz, 4H), 0.98 (br. s., 6H). MS: calc'd 419 (M+H)$^+$. measured 419 (M+H)$^+$.

Example 15

2-Amino-N4,N4-dipropyl-N8-[3-(pyrrolidine-1-carbonyl)phenyl]-3H-1-benzazepine-4,8-dicarboxamide

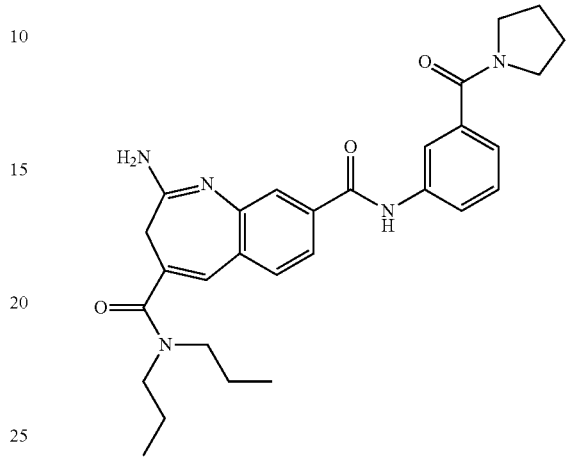

The title compound was prepared in analogy to Example 1 by using (3-aminophenyl)-(pyrrolidin-1-yl)methanone (compound 15A) instead of pyridin-3-amine. Example 15 was obtained as a yellow gum (15 mg). $^1$H NMR (400 MHz, CD$_3$OD) δ ppm=7.94-8.04 (m, 3H), 7.84 (d, J=8.03 Hz, 1H), 7.72 (d, J=8.28 Hz, 1H), 7.49 (t, J=7.84 Hz, 1H), 7.35 (d, J=7.53 Hz, 1H), 7.13 (s, 1H), 3.64 (t J=6.90 Hz, 2H), 3.43-3.58 (m, 6H), 3.40 (s, 2H), 1.91-2.08 (m, 4H), 1.66-1.78 (m, 4H), 0.87-1.07 (m, 6H). MS: calc'd 502 (M+H)$^+$. measured 502 (M+H)$^+$.

Preparation of (3-aminophenyl)(pyrrolidin-1-yl)methanone (Compound 15A)

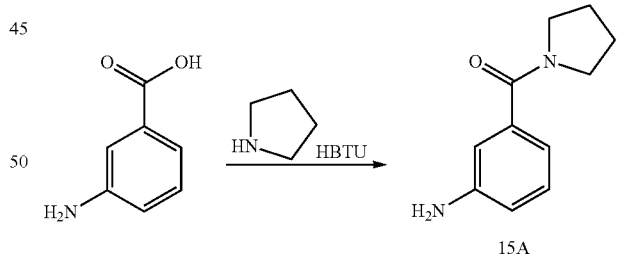

To a mixture of 3-aminobenzoic acid (500 mg, 3.6 mmol), HBTU (1.6 g, 4.3 mmol), DIPEA (930 mg, 7.2 mmol) in DMF (50 mL) was added pyrrolidine (380 mg, 5.4 mmol) at 0° C. After the reaction mixture was stirred for 16 hrs at 20° C., it was quenched with sat. NH$_4$Cl (50 mL), diluted with H$_2$O (200 mL), and extracted with EA (100 mL×2). The combined organic layers were washed with brine (100 mL×2), dried over Na$_2$SO$_4$ and concentrated to give the crude product that was purified by silica gel column chromatography (PE: EA=1:1) to give (3-aminophenyl)(pyrrolidin-1-yl)methanone (compound 15A, 400 mg, 60%) as yellow solid. MS: calc'd 191 (M+H)$^+$. measured 191 (M+H)$^+$.

Example 16

2-Amino-N4,N4-dipropyl-N8-[5-(pyrrolidine-1-carbonyl)-3-pyridyl]-3H-1-benzazepine-4,8-dicarboxamide

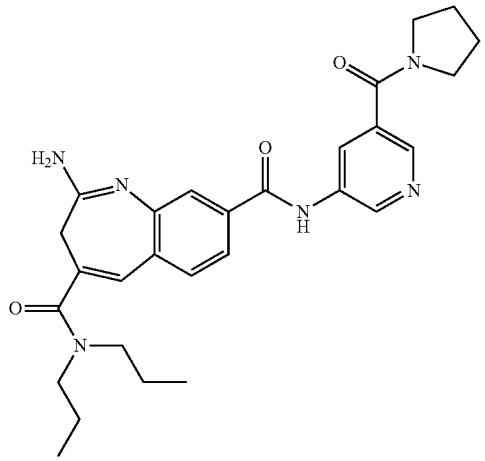 [SMILES: CCCN(CCC)C(=O)C1=Cc2ccc(C(=O)Nc3cncc(C(=O)N4CCCC4)c3)cc2N=C(N)C1]

The title compound was prepared in analogy to Example 1 by using (5-aminopyridin-3-yl)(pyrrolidin-1-yl)methanone (Compound 16A) instead of pyridin-3-amine. Example 16 was obtained as a yellow gum (3.1 mg). $^1$H NMR (300 MHz, CD$_3$OD) δ ppm=9.39-9.32 (m, 1H), 8.83-8.66 (m, 2H), 8.13-8.02 (m, 2H), 7.80-7.72 (m, 1H), 7.18-7.11 (m, 1H), 3.72-3.56 (m, 4H), 3.55-3.43 (m, 4H), 3.42-3.38 (m, 2H), 2.14-1.93 (m, 4H), 1.81-1.63 (m, 4H), 1.08-0.81 (m, 6H). MS: calc'd 503 (M+H)$^+$. measured 503 (M+H)$^+$.

Preparation of (5-aminopyridin-3-yl)(pyrrolidin-1-yl)methanone (Compound 16A)

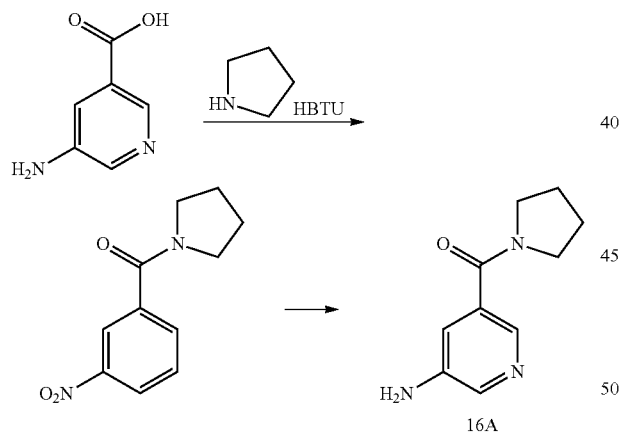

A solution of 5-nitronicotinic acid (200 mg, 1.19 mmol) in DCM (4 mL) was added HBTU (544 mg, 1.43 mmol), DIPEA (307 mg, 2.38 mmol) and pyrrolidine (101 mg, 1.43 mmol) at 0° C. The reaction mixture was stirred at 25° C. for 18 hrs. Water (10 mL) was added, and the mixture was extracted with EA (10 mL). The organic layer was washed with brine, dried over anhydrous Na$_2$SO$_4$ and concentrated to give the crude product. The crude product was purified by silica gel column chromatography (PE:EA=1:1) to give the desired product (5-nitropyridin-3-yl)(pyrrolidin-1-yl)methanone (240 mg, 92%) as a yellow solid. MS: calc'd 222 (M+H)$^+$. measured 222 (M+H)$^+$.

To a solution of (5-nitropyridin-3-yl)(pyrrolidin-1-yl)methanone (240 mg, 1.13 mmol) in MeOH (5 mL) was added Pd/C (30 mg) at 25° C. The reaction mixture was stirred at 25° C. under 1 atmosphere pressure of H$_2$ for 18 hrs. The mixture was filtered and concentrated to give the desired product (5-aminopyridin-3-yl)(pyrrolidin-1-yl)methanone (compound 16A, 180 mg, 87%) as a yellow solid. MS: calc'd 192 (M+H)$^+$. measured 192 (M+H)$^+$.

Example 17

2-Amino-N8-[3-(2-aminoethyl)phenyl]-N4,N4-dipropyl-3H-1-benzazepine-4,8-dicarboxamide

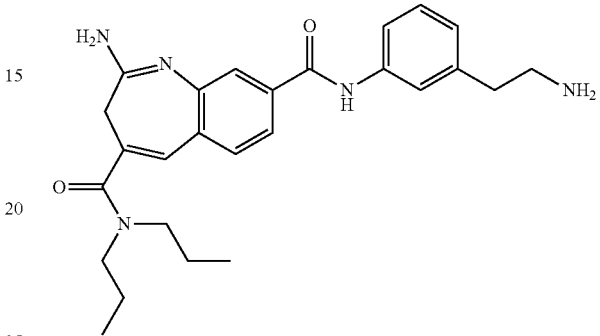

The title compound was prepared in analogy to Example 1 by using tert-butyl N-[2-(3-aminophenyl)ethyl]carbamate instead of pyridin-3-amine. Example 17 was obtained as a white solid (20 mg). $^1$H NMR (400 MHz, CD$_3$OD) δ ppm=7.70-7.99 (m, 3H), 7.50-7.68 (m, 2H), 7.39 (t, J=7.9 Hz, 1H), 7.13 (d, J=7.5 Hz, 1H), 6.90-7.07 (m, 1H), 3.47 (br. s., 4H), 3.33 (dt, J=3.1, 1.6 Hz, 2H), 3.14-3.27 (m, 2H), 3.01 (t, J=7.2 Hz, 2H), 1.54-1.81 (m, 4H), 0.70-1.14 (m, 6H). MS: calc'd 448 (M+H)$^+$. measured 448 (M+H)$^+$.

Example 18

2-Amino-N8-(5-methyl-3-pyridyl)-N4,N4-dipropyl-3H-1-benzazepine-4,8-dicarboxamide

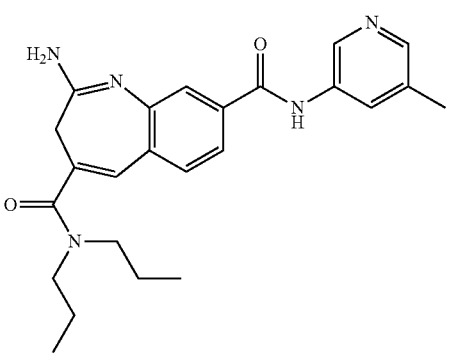 [SMILES: CCCN(CCC)C(=O)C1=Cc2ccc(C(=O)Nc3cncc(C)c3)cc2N=C(N)C1]

The title compound was prepared in analogy to Example 1 by using 5-methylpyridin-3-amine instead of pyridin-3-amine. Example 18 was obtained (12.5 mg) as a yellow solid. $^1$H NMR (300 MHz, DMSO-d$_6$) δ ppm=10.39-10.32 (m, 1H), 8.79-8.72 (m, 1H), 8.18-8.05 (m, 2H), 7.70-7.63 (m, 1H), 7.52-7.37 (m, 2H), 6.98-6.85 (m, 2H), 6.81-6.75 (m, 1H), 3.31-3.28 (m, 4H), 2.77-2.70 (m, 2H), 2.36-2.29 (m, 3H), 1.66-1.47 (m, 4H), 0.97-0.66 (m, 6H). MS: calc'd 420 (M+H)$^+$. measured 420 (M+H)$^+$.

Example 19

2-Amino-N8-(3-fluorophenyl)-N4,N4-dipropyl-3H-1-benzazepine-4,8-dicarboxamide

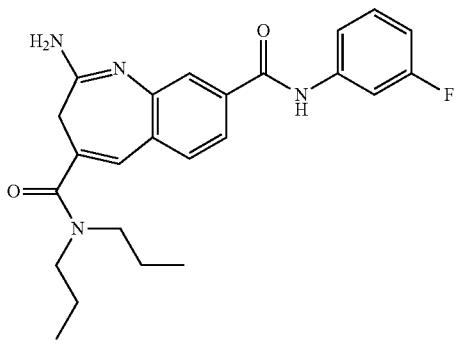 [SMILES: CCCN(CCC)C(=O)C1=Cc2ccc(C(=O)Nc3cccc(F)c3)cc2N=C(N)C1]

The title compound was prepared in analogy to Example 1 by using 3-fluoroaniline instead of pyridin-3-amine. Example 19 was obtained as a yellow solid (50 mg). $^1$H NMR (400 MHz, DMSO-d$_6$) δ ppm=10.6 (brs, 1H), 9.89 (brs, 1H), 8.98 (brs, 1H), 8.00-7.92 (m, 2H), 7.80-7.69 (m, 2H), 7.61-7.55 (m, 1H), 7.47-7.30 (m, 1H), 7.08-7.05 (m, 1H), 7.02-6.95 (m, 1H), 3.30-3.28 (m, 6H), 1.61-1.58 (m, 4H), 0.92-0.83 (m, 6H). MS: calc'd 423 (M+H)$^+$. measured 423 (M+H)$^+$.

Example 20

2-Amino-N8-(5-fluoro-3-pyridyl)-N4,N4-dipropyl-3H-1-benzazepine-4,8-dicarboxamide

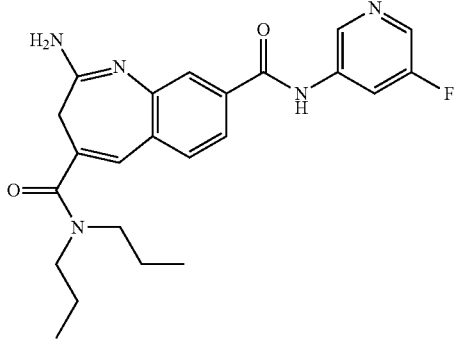 [SMILES: CCCN(CCC)C(=O)C1=Cc2ccc(C(=O)Nc3cncc(F)c3)cc2N=C(N)C1]

The title compound was prepared in analogy to Example 1 by using 5-fluoropyridin-3-amine instead of pyridin-3-amine. Example 20 was obtained as a yellow solid (8 mg). $^1$H NMR (400 MHz, CD$_3$OD) δ ppm=9.32 (br. s., 1H), 8.55-8.83 (m, 2H), 8.03-8.16 (m, 2H), 7.76 (d, J=8.03 Hz, 1H), 7.10-7.18 (m, 1H), 3.49 (br. s., 4H), 3.42 (br. s., 2H), 1.72 (sxt, J=7.28 Hz, 4H), 0.97 (d, J=10.67 Hz, 6H). MS: calc'd 424 (M+H)$^+$. measured 424 (M+H)$^+$.

Example 21

2-Amino-N8-(2-methyl-3-pyridyl)-N4,N4-dipropyl-3H-1-benzazepine-4,8-dicarboxamide

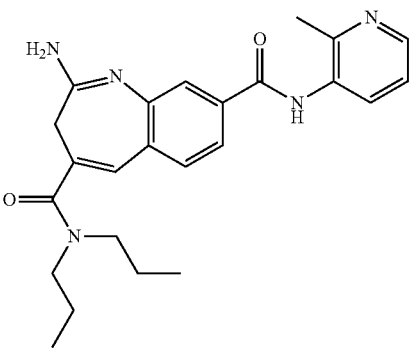 [SMILES: CCCN(CCC)C(=O)C1=Cc2ccc(C(=O)Nc3cccnc3C)cc2N=C(N)C1]

The title compound was prepared in analogy to Example 1 by using 2-methylpyridin-3-amine instead of pyridin-3-amine. Example 21 was obtained as a yellow gum (60 mg). $^1$H NMR (400 MHz, DMSO-d$_6$) δ ppm=11.01 (br. s., 1H), 10.04 (br. s., 1H), 9.22 (br. s., 1H), 8.64-8.71 (m, 1H), 8.55 (br. s., 1H), 8.01-8.13 (m, 2H), 7.90 (br. s., 1H), 7.76 (d, J=8.16 Hz, 1H), 7.08 (s, 1H), 3.37 (br. s., 6H), 2.66-2.75 (m, 3H), 1.53-1.65 (m, 4H), 0.75-0.98 (m, 6H). MS: calc'd 420 (M+H)$^+$. measured 420 (M+H)$^+$.

Example 22

2-Amino-N8-(6-methyl-3-pyridyl)-N4,N4-dipropyl-3H-1-benzazepine-4,8-dicarboxamide

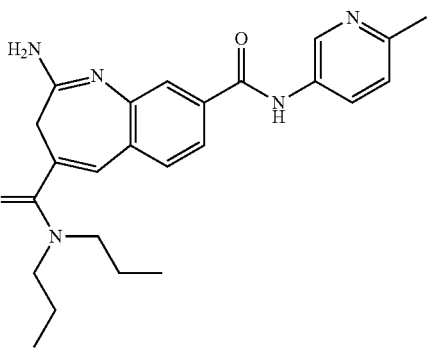

The title compound was prepared in analogy to Example 1 by using 6-methylpyridin-3-amine instead of pyridin-3-amine. Example 22 was obtained as a yellow solid (34.3 mg). $^1$H NMR (400 MHz, DMSO-d$_6$) δ ppm=11.33-11.23 (m, 1H), 10.02-9.94 (m, 1H), 9.22-9.08 (m, 2H), 8.64-8.55 (m, 1H), 8.12-8.01 (m, 2H), 7.84-7.73 (m, 2H), 7.10-7.05 (m, 1H), 3.36-3.24 (m, 6H), 2.71-2.64 (m, 3H), 1.67-1.52 (m, 4H), 1.00-0.72 (m, 6H). MS: calc'd 420 (M+H)$^+$. measured 420 (M+H)$^+$.

Example 23

2-Amino-N8-(3,5-dimethylphenyl)-N4,N4-dipropyl-3H-1-benzazepine-4,8-dicarboxamide

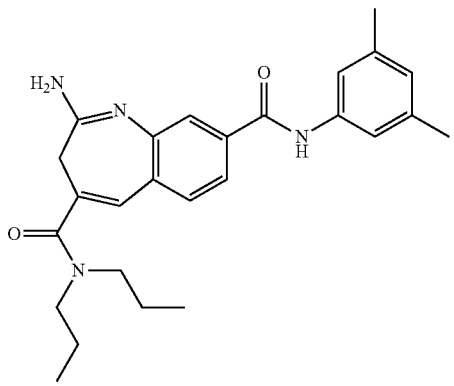 [SMILES: CCCN(CCC)C(=O)C1=Cc2ccc(C(=O)Nc3cc(C)cc(C)c3)cc2N=C(N)C1]

The title compound was prepared in analogy to Example 1 by using 3,5-dimethylaniline instead of pyridin-3-amine. Example 23 was obtained as a yellow solid (16 mg). $^1$H NMR (400 MHz, DMSO-d$_6$) ppm=7.77 (d, J=1.5 Hz, 1H), 7.70 (dd, J=8.2, 1.6 Hz, 1H), 7.54 (d, J=8.3 Hz, 1H), 7.34 (s, 2H), 6.99 (s, 1H), 6.85 (s, 1H), 3.35-3.61 (m, 4H), 3.21-3.23 (m, 2H), 2.35 (m, 6H), 1.49-1.86 (m, 4H), 0.59-1.20 ppm (m, 6H). MS: calc'd 433 (M+H)$^+$. measured 433 (M+H)$^+$.

Example 24

2-Amino-N8-[4-(aminomethyl)phenyl]-N4,N4-dipropyl-3H-1-benzazepine-4,8-dicarboxamide

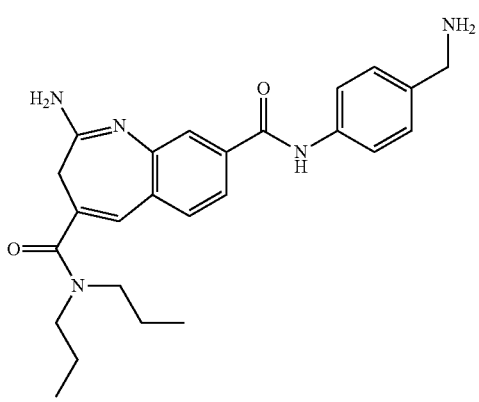 [SMILES: CCCN(CCC)C(=O)C1=Cc2ccc(C(=O)Nc3ccc(CN)cc3)cc2N=C(N)C1]

The title compound was prepared in analogy to Example 1 by using tert-butyl N-[(4-aminophenyl)methyl]carbamate instead of pyridin-3-amine. Example 24 was obtained as a yellow solid (4 mg). $^1$H NMR (400 MHz, DMSO-d$_6$) δ ppm=7.84 (d, J=8.5 Hz, 2H), 7.76 (d, J=1.5 Hz, 1H), 7.67 (dd, J=8.0, 1.8 Hz, 1H), 7.38-7.57 (m, 3H), 6.88-7.03 (m, 1H), 4.04-4.21 (m, 2H), 3.37-3.54 (m, 4H), 3.31 (m, 2H), 1.54-1.80 (m, 4H), 0.65-1.11 ppm (m, 6H). MS: calc'd 434 (M+H)$^+$. measured 434 (M+H)$^+$.

Example 25

2-Amino-N8-[4-(2-aminoethyl)phenyl]-N4,N4-dipropyl-3H-1-benzazepine-4,8-dicarboxamide

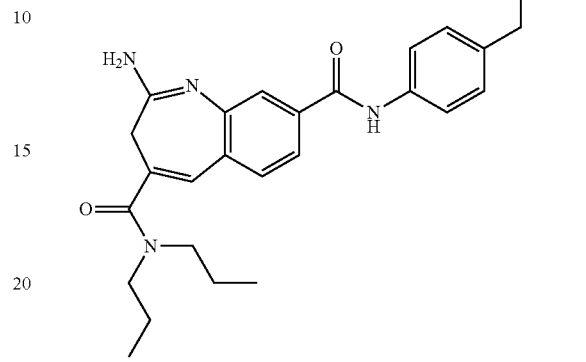

The title compound was prepared in analogy to Example 1 by using tert-butyl N-[2-(4-aminophenyl)ethyl]carbamate instead of pyridin-3-amine. Example 25 was obtained as a yellow solid (4 mg). $^1$H NMR (400 MHz, DMSO-d$_6$) δ ppm=7.86-8.00 (m, 2H), 7.57-7.80 (m, 3H), 7.34 (d, J=8.5 Hz, 2H), 7.11 (s, 1H), 3.49 (m, 4H), 3.12-3.27 (m, 2H), 2.90-3.07 (m, 2H), 2.84 (m, 4H), 1.72 (m, 2H), 0.96 ppm (m, 6H). MS: calc'd 448 (M+H)$^+$. measured 448 (M+H)$^+$.

Example 26

2-Amino-N4-(3-hydroxypropyl)-N8-(m-tolyl)-N4-propyl-3H-1-benzazepine-4,8-dicarboxamide

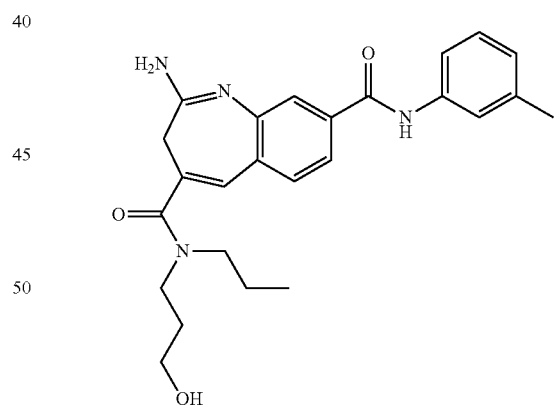

A detailed synthetic route is provided in Scheme 5.

Preparation of Compound P

To a solution of 2-amino-8-(methoxycarbonyl)-3H-benzo[b]azepine-4-carboxylic acid hydrochloride (compound A, 2.0 g, 6.7 mmol) in DMF (50 mL) was added HBTU (3.1 g, 8.1 mmol), DIPEA (3.4 g, 26.8 mmol) and 3-(propylamino)propan-1-ol (870 mg, 7.4 mmol) at 0° C. After the reaction mixture was stirred at 25° C. for 18 hrs, water (100 mL) was added and the mixture was extracted with EA (50 mL). The organic layer was washed with brine, dried over anhydrous Na$_2$SO$_4$ and concentrated to give the crude product. The crude product was purified by silica gel column chromatography (PE:EA=1:1-0:1) to give the desired product methyl 2-amino-4-((3-hydroxypropyl)(propyl)carbamoyl)-3H-benzo[b]azepine-8-carboxylate (compound P, 2 g) as a yellow oil. MS: calc'd 360 (M+H)$^+$. measured 360 (M+H)$^+$.

Preparation of Compound Q

To a solution of methyl 2-amino-4-((3-hydroxypropyl)(propyl)carbamoyl)-3H-benzo[b]azepine-8-carboxylate (compound P, 2.0 g, 5.56 mmol) in DCM (50 mL) was added TEA (1.1 g, 11.12 mmol) and Boc$_2$O (218 mg, 8.34 mmol) at 0° C. After the reaction mixture was stirred at 25° C. for 24 hrs, water (10 mL) was added and the mixture was extracted with DCM (50 mL). The organic layer was washed with brine, dried over Na$_2$SO$_4$ and concentrated in vacuo. The residue was purified by silica gel column chromatography (PE:EA=1:1) to give the desired product methyl 2-((tert-butoxycarbonyl)amino)-4-((3-hydroxypropyl)-(propyl)carbamoyl)-3H-benzo[b]azepine-8-carboxylate (compound Q, 1.3 g) as a yellow solid. MS: calc'd 460 (M+H)$^+$. measured 460 (M+H)$^+$.

Scheme 5

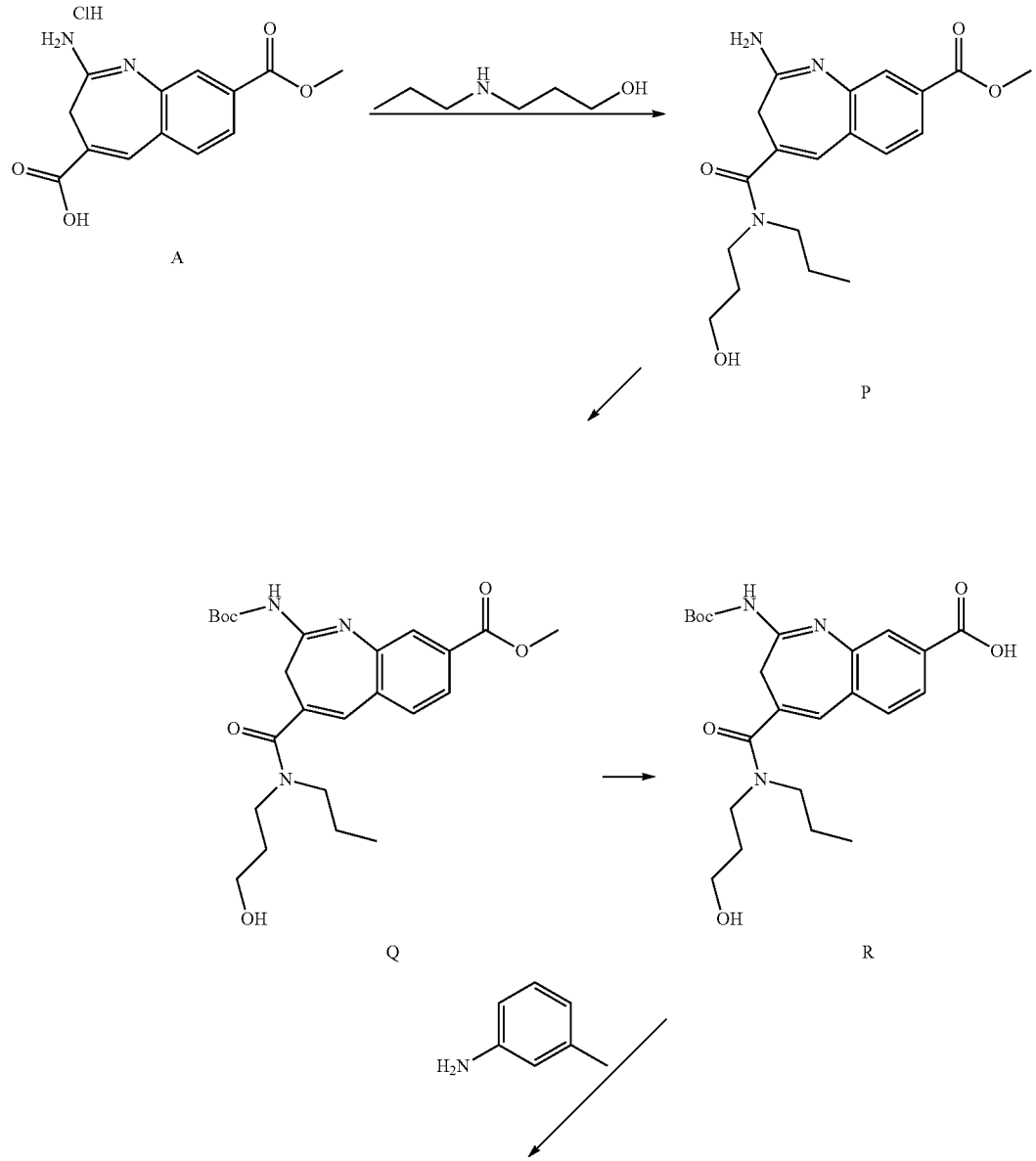

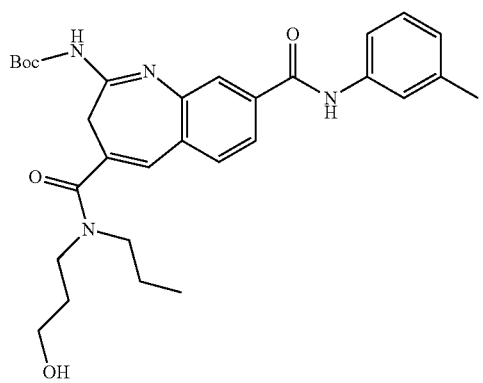

T

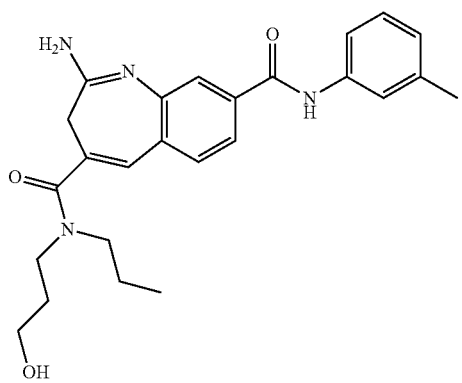

26

Preparation of Compound R

To a solution of methyl 2-((tert-butoxycarbonyl)amino)-4-((3-hydroxypropyl)-(propyl)carbamoyl)-3H-benzo[b]azepine-8-carboxylate (compound Q, 100 mg, 0.22 mmol) in THF/H$_2$O (1/1, 2 mL) was added aq. LiOH (1 M, 0.3 mL, 0.30 mmol) at 0° C. Then the mixture was warmed to 25° C. and stirred for 5 hrs. The mixture was poured into ice-water (10 mL) and acidified with aq. citric acid (5%) to pH 5. The mixture was extracted with EtOAc (30 mL×3) and the combined organic layers were washed with brine (20 mL×2), dried over Na$_2$SO$_4$ and concentrated in vacuo to give crude 2-((tert-butoxycarbonyl)amino)-4-((3-hydroxypropyl)-(propyl)carbamoyl)-3H-benzo[b]azepine-8-carboxylic acid (compound R, 70 mg) as a yellow solid. MS: calc'd 450 (M+H)$^+$. measured 450 (M+H)$^+$.

Preparation of Compound T

To a solution of 2-((tert-butoxycarbonyl)amino)-4-((3-hydroxypropyl)(propyl)carbamoyl)-3H-benzo[b]azepine-8-carboxylic acid (compound R, 30 mg, 0.067 mmol) in DMF (1 mL) was added successively EDCI (32 mg, 0.167 mmol), HOBT (11 mg, 0.084 mmol), DIEA (35 mg, 0.268 mmol), DMAP (2 mg, 0.017 mmol) and m-toluidine (11 mg, 0.101 mmol). After the reaction was stirred at 25° C. for 18 hrs, it was poured into ice-water (10 mL) and extracted with EtOAc (20 mL×2). The combined organic layers were washed with aq. citric acid (5%) and aq. Na$_2$CO$_3$, dried over Na$_2$SO$_4$. After filtration, the filtrate was concentrated in vacuo to give tert-butyl (4-((3-hydroxypropyl)(propyl)carbamoyl)-8-(m-tolylcarbamoyl)-3H-benzo[b]azepin-2-yl)carbamate (compound T, 30 mg, crude) as a yellow solid. MS: calc'd 535 (M+H)$^+$. measured 535 (M+H)$^+$.

Preparation of Example 26

To a solution of tert-butyl (4-((3-hydroxypropyl)(propyl)carbamoyl)-8-(m-tolyl-carbamoyl)-3H-benzo[b]azepin-2-yl)carbamate (compound T, 30 mg, 0.058 mmol) in DCM (0.8 mL) was added a solution of TFA (128 mg, 0.123 mmol) in DCM (0.2 mL) at 0° C. After the reaction was stirred at 25° C. for 4-5 hrs, the solvent was removed in vacuo and the residue was basified to pH 8 with sat. NaHCO$_3$. The mixture was extracted with DCM and dried over Na$_2$SO$_4$. Removal of solvent in vacuo gave the crude product which was purified by prep-HPLC to give 2-amino-N8-(5-methyl-3-pyridyl)-N4,N4-dipropyl-3H-1-benzazepine-4,8-dicarboxamide (Example 26, 1.6 mg) as a yellow solid. $^1$H NMR (300 MHz, CD$_3$OD) δ ppm=8.03-7.87 (m, 2H), 7.77-7.67 (m, 1H), 7.58-7.44 (m, 2H), 7.33-7.22 (m, 1H), 7.17-7.11 (m, 1H), 7.07-6.99 (m, 1H), 3.80-3.43 (m, 6H), 3.42-3.36 (m, 2H), 2.49-2.28 (m, 3H), 1.97-1.84 (m, 2H), 1.80-1.64 (m, 2H), 1.09-0.86 (m, 3H). MS: calc'd 435 (M+H)$^+$. measured 435 (M+H)$^+$.

Example 27

2-Amino-N8-(o-tolyl)-N4,N4-dipropyl-3H-1-benzazepine-4,8-dicarboxamide

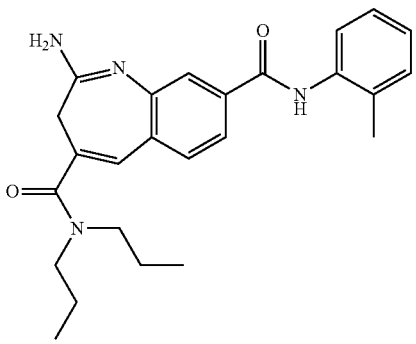 [SMILES: CCCN(CCC)C(=O)C1=Cc2ccc(C(=O)Nc3ccccc3C)cc2N=C(N)C1]

The title compound was prepared in analogy to Example 1 by using o-toluidine instead of pyridin-3-amine. Example 27 was obtained as a yellow gum (12 mg). $^1$H NMR (400 MHz, CDCl$_3$) δ ppm=7.99 (d, J=7.91 Hz, 1H), 7.79 (s, 1H), 7.68 (s, 1H), 7.64 (d, J=8.16 Hz, 1H), 7.42 (d, J=8.16 Hz, 1H), 7.22-7.32 (m, 1H), 7.11-7.17 (m, 1H), 6.85 (s, 1H), 3.48 (br. s., 4H), 2.81 (s, 2H), 2.37 (s, 3H), 1.63-1.74 (m, 4H), 0.89-1.03 (m, 6H). MS: calc'd 419 (M+H)$^+$. measured 419 (M+H)$^+$

Example 28

2-Amino-N4,N4-dipropyl-N8-(p-tolyl)-3H-1-benzazepine-4,8-dicarboxamide

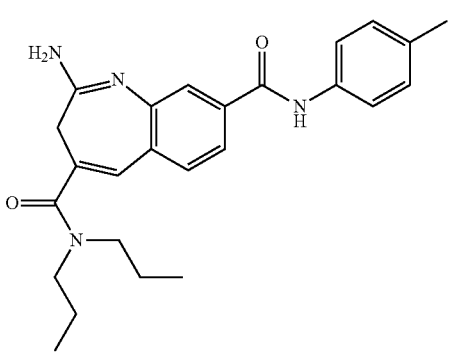 [SMILES: CCCN(CCC)C(=O)C1=Cc2ccc(C(=O)Nc3ccc(C)cc3)cc2N=C(N)C1]

The title compound was prepared in analogy to Example 1 by using p-toluidine instead of pyridin-3-amine. Example 28 was obtained as a yellow solid (43.7 mg). $^1$H NMR (400 MHz, DMSO-$d_6$): δ ppm=10.42 (br, 1H), 10.01 (br, 1H), 9.21 (br, 1H), 7.92-8.01 (m, 2H), 7.62-7.74 (m, 3H), 7.11-7.23 (d, 2H), 7.04 (s, 1H), 3.25-3.37 (m, 6H), 2.28 (s, 3H), 1.48-1.66 (m, 4H), 0.66-1.06 (d, 6H). MS: calc'd 419 (M+H)$^+$. measured 419 (M+H)$^+$

Example 29

2-Amino-N8-(3-ethylphenyl)-N4,N4-dipropyl-3H-1-benzazepine-4,8-dicarboxamide

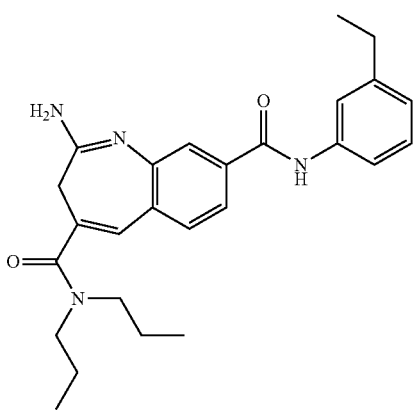 [SMILES: CCCN(CCC)C(=O)C1=Cc2ccc(C(=O)Nc3cccc(CC)c3)cc2N=C(N)C1]

The title compound was prepared in analogy to Example 1 by using 3-ethylaniline instead of pyridin-3-amine. Example 29 was obtained as a white solid (35 mg). $^1$H NMR (400 MHz, CDCl$_3$) δ ppm=7.96 (s, 1H), 7.67 (d, J=1.63 Hz, 1H), 7.63 (dd, J=1.88, 8.03 Hz, 1H), 7.56 (s, 1H), 7.47 (d, J=7.78 Hz, 1H), 7.41 (d, J=8.16 Hz, 1H), 7.29-7.33 (m, 1H), 7.02 (d, J=7.65 Hz, 1H), 6.85 (s, 1H), 3.48 (br. s., 4H), 2.81 (s, 2H), 2.69 (q, J=7.61 Hz, 2H), 1.69 (qd, J 7.47, 14.98 Hz, 4H), 1.28 (t J=7.59 Hz, 3H), 0.95 (t J=7.15 Hz, 6H). MS: calc'd 433 (M+H)$^+$. measured 433 (M+H)$^+$

Example 30

2-Amino-N8-(3-methoxyphenyl)-N4,N4-dipropyl-3H-1-benzazepine-4,8-dicarboxamide

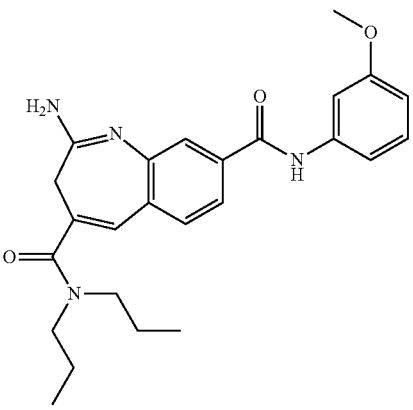 [SMILES: CCCN(CCC)C(=O)C1=Cc2ccc(C(=O)Nc3cccc(OC)c3)cc2N=C(N)C1]

The title compound was prepared in analogy to Example 1 by using 3-methoxyaniline instead of pyridin-3-amine. Example 30 was obtained as a yellow solid (30.9 mg). $^1$H NMR (400 MHz, DMSO-$d_6$) δ ppm=10.47 (br, 1H), 10.02 (br, 1H), 9.2 (br, 1H), 7.93-8.02 (m, 2H), 7.67-7.74 (d, 1H), 7.46-7.52 (t, 1H), 7.36-7.44 (m, 1H), 7.23-7.31 (t, 1H), 7.04 (s, 1H), 6.67-6.75 (dd, 1H), 3.76 (s, 3H), 3.35 (m., 6H), 1.49-1.65 (m, 4H), 0.70-0.98 (d, 6H). MS: calc'd 435 (M+H)$^+$. measured 435 (M+H)$^+$

Example 31

2-Amino-N4,N4-dipropyl-N8-[3-(trifluoromethyl)phenyl]-3H-1-benzazepine-4,8-dicarboxamide

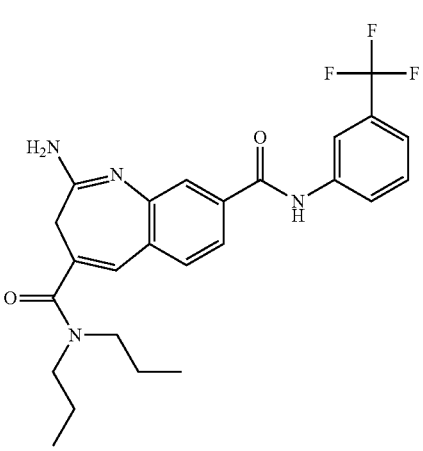 [SMILES: CCCN(CCC)C(=O)C1=Cc2ccc(C(=O)Nc3cccc(C(F)(F)F)c3)cc2N=C(N)C1]

The title compound was prepared in analogy to Example 1 by using 3-(trifluoromethyl)-aniline instead of pyridin-3-amine. Example 31 was obtained as a yellow gum (12 mg). $^1$H NMR (400 MHz, CDCl$_3$) δ ppm=8.20 (s, 1H), 8.03 (s, 1H), 7.86 (d, J=8.16 Hz, 1H), 7.68 (d, J=1.76 Hz, 1H), 7.62 (dd, J=1.88, 8.16 Hz, 1H), 7.48-7.54 (m, 1H), 7.42 (d, J=8.16 Hz, 2H), 6.84 (s, 1H), 3.36-3.57 (m, 4H), 2.81 (s, 2H), 1.69 (qd, J=7.47, 14.98 Hz, 4H), 0.95 (t, J=7.22 Hz, 6H). MS: calc'd 473 (M+H)$^+$. measured 473 (M+H)$^+$

Example 32

2-Amino-N8-(3-chlorophenyl)-N4,N4-dipropyl-3H-1-benzazepine-4,8-dicarboxamide

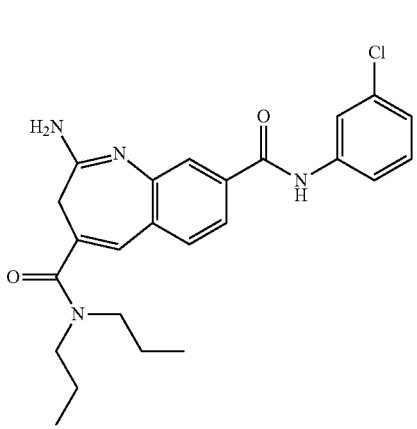 [SMILES: CCCN(CCC)C(=O)C1=Cc2ccc(C(=O)Nc3cccc(Cl)c3)cc2N=C(N)C1]

The title compound was prepared in analogy to Example 1 by using 3-chloroaniline instead of pyridin-3-amine. Example 32 was obtained as a yellow solid (21.8 mg). $^1$H NMR (400 MHz, CDCl$_3$) δ ppm=8.05 (s, 1H), 7.85 (t, J=2.01 Hz, 1H), 7.66 (d, J=1.88 Hz, 1H), 7.61 (dd, J=1.94, 8.09 Hz, 1H), 7.47-7.52 (m, 1H), 7.41 (d, J=8.16 Hz, 1H), 7.29-7.34 (m, 1H), 7.14 (ddd, J=0.94, 1.98, 8.00 Hz, 1H), 6.83 (s, 1H), 3.49 (d, J=13.93 Hz, 4H), 2.80 (s, 2H), 1.69 (qd, J=7.35, 14.98 Hz, 4H), 0.95 (t, J=7.15 Hz, 6H). MS: calc'd 439 (M+H)$^+$. measured 439 (M+H)$^+$

Example 33

2-Amino-N8-[5-(aminomethyl)-3-pyridyl]-N4,N4-dipropyl-3H-1-benzazepine-4,8-dicarboxamide

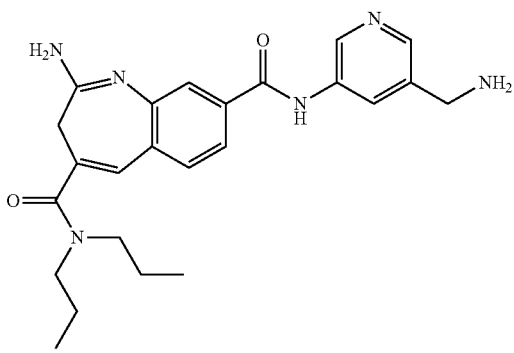 [SMILES: CCCN(CCC)C(=O)C1=Cc2ccc(C(=O)Nc3cncc(CN)c3)cc2N=C(N)C1]

The title compound was prepared in analogy to Example 1 by using tert-butyl N-[(5-amino-3-pyridyl)methyl]carbamate (compound 33A) instead of pyridin-3-amine. Example 33 was obtained as a white solid (56.5 mg). $^1$H NMR (400 MHz, METHANOL-d$_4$) δ ppm=8.85 (s, 1H), 8.56 (s, 1H), 8.43 (s, 1H), 7.88 (s, 1H), 7.82 (d, J=8 Hz, 1H), 7.62 (d, J=8 Hz, 1H), 7.03 (s, 1H), 4.89 (m, 2H), 4.23 (s, 2H), 3.45 (m, 4H), 1.72-1.67 (m, 4H), 0.98-0.90 (m, 6H). MS: calc'd 435 (M+H)$^+$. measured 435 (M+H)$^+$.

Preparation of tert-butyl N-[(5-amino-3-pyridyl)methyl]carbamate (Compound 33A)

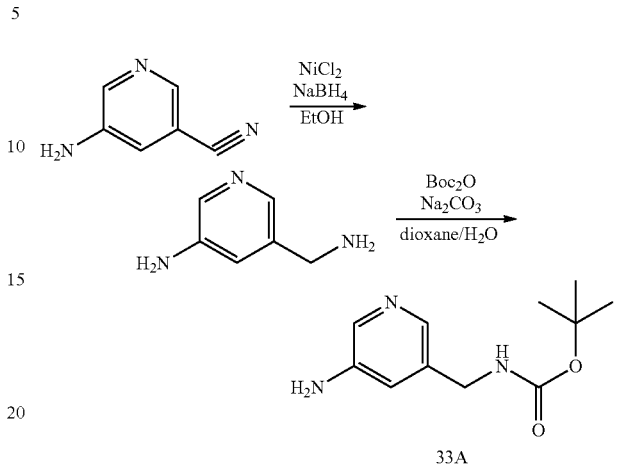

To a stirred solution of 5-aminopyridine-3-carbonitrile (238 mg, 2.0 mmol), anhydrous NiCl$_2$ (259 mg, 2.0 mmol) in ethanol (8 mL) was added NaBH$_4$ (303 mg, 8.0 mmol) portion-wise at 25° C. After 8 hrs, the mixture was filtered through celite and the filtrate was concentrated to give the crude product, which was used directly in the following step. 5-(aminomethyl)pyridin-3-amine (dark brown oil, 277 mg). MS: calc'd 124 (M+H)$^+$. measured 124 (M+H)$^+$.

To a solution of crude 5-(aminomethyl)pyridin-3-amine (277 mg) in dioxane (8 mL) and H$_2$O (8 mL) was added Na$_2$CO$_3$ (954 mg, 9.0 mmol). After the mixture was stirred at 25° C. for a while, Boc$_2$O (1.47 g, 6.7 mmol) was added. After 3.5 hrs, the mixture was diluted with water and extracted with EA (25 mL×3) and DCM (25 mL×3). The combined organic layers were dried over Na$_2$SO$_4$ and concentrated in vacuo to give an orange oil. The oil was purified by silica gel column chromatography (PE:EA=1:0 to 1:1) to give the desired product tert-butyl N-[(5-amino-3-pyridyl)methyl]carbamate (compound 33A, 92 mg, 21% yield over two steps) as an orange sticky solid. MS: calc'd 224 (M+H)$^+$. measured 224 (M+H)$^+$.

Example 34

2-Amino-N4,N4-dipropyl-N8-pyridazin-4-yl-3H-1-benzazepine-4,8-dicarboxamide

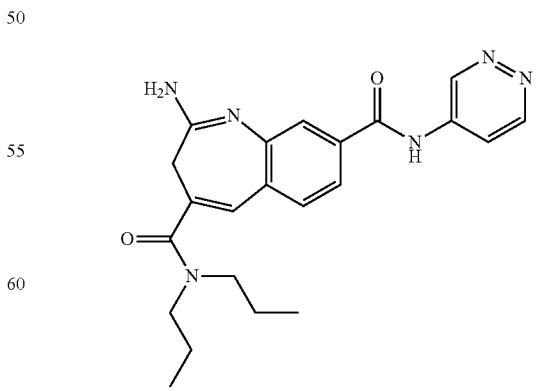

The title compound was prepared in analogy to Example 1 by using pyridazin-4-amine instead of pyridin-3-amine.

Example 34 was obtained as a white solid (30.5 mg). ¹H NMR (400 MHz, CD₃OD) δ ppm=9.50 (s, 1H), 9.05 (d, J=8 Hz, 1H), 8.29-8.27 (m, 1H), 7.80 (s, 1H), 7.72-7.69 (m, 1H), 7.54 (d, J=8 Hz, 1H), 6.69 (s, 1H), 4.87 (m, 2H), 3.44 (t J=8 Hz, 4H), 1.71-1.66 (m, 4H), 0.96-0.90 (m, 6H). MS: calc'd 407 (M+H)⁺. measured 407 (M+H)⁺.

Example 35

2-Amino-N8-(6-ethoxy-3-pyridyl)-N4,N4-dipropyl-3H-1-benzazepine-4,8-dicarboxamide

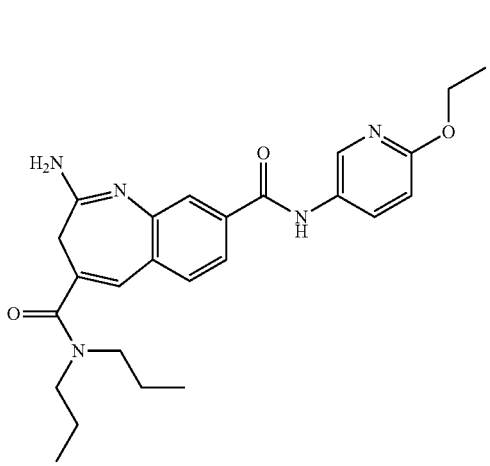 [SMILES: CCCN(CCC)C(=O)C1=Cc2ccc(C(=O)Nc3ccc(OCC)nc3)cc2N=C(N)C1]

The title compound was prepared in analogy to Example 1 by using 6-ethoxypyridin-3-amine instead of pyridin-3-amine. Example 35 was obtained as a yellow solid (6 mg). ¹H NMR (400 MHz, CD₃OD) δ ppm=8.76 (brs, 1H), 8.35 (d, J=7.8 Hz, 1H), 8.05-7.99 (m, 2H), 7.74 (d, J=8.3 Hz, 1H), 7.25 (d, J=9.0 Hz, 1H), 7.14 (s, 1H), 4.46 (q, J=6.9 Hz, 2H), 3.50 (brs, 4H), 3.40 (s, 2H), 1.80-1.65 (m, 4H), 1.49 (t, J=7.0 Hz, 3H), 0.97 (brs, 6H). MS:calc'd 450 (M+H)⁺. measured 450 (M+H)⁺.

Example 36

2-Amino-N8-[3-(aminomethyl)phenyl]-N4,N4-dipropyl-3H-1-benzazepine-4,8-dicarboxamide

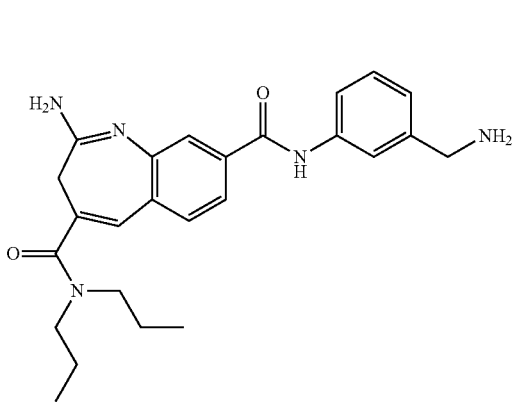 [SMILES: CCCN(CCC)C(=O)C1=Cc2ccc(C(=O)Nc3cccc(CN)c3)cc2N=C(N)C1]

The title compound was prepared in analogy to Example 1 by using tert-butyl N-[(3-aminophenyl)methyl]carbamate instead of pyridin-3-amine. Example 36 was obtained as a yellow solid (6 mg). ¹H NMR (400 MHz, CDCl₃) δ ppm=7.86-8.05 (m, 3H), 7.61-7.75 (m, 2H), 7.50 (t, J=7.9 Hz, 1H), 7.30 (d, J=7.5 Hz, 1H), 7.12 (s, 1H), 4.17 (s, 2H), 3.49 (br. s., 4H), 2.83 (s, 2H), 1.51-1.76 (m, 4H), 0.96 ppm (br. s., 6H). MS: calc'd 434 (M+H)⁺. measured 434 (M+H)⁺

Example 37

2-Amino-N8-(1-methylpyrazol-3-yl)-N4,N4-dipropyl-3H-1-benzazepine-4,8-dicarboxamide

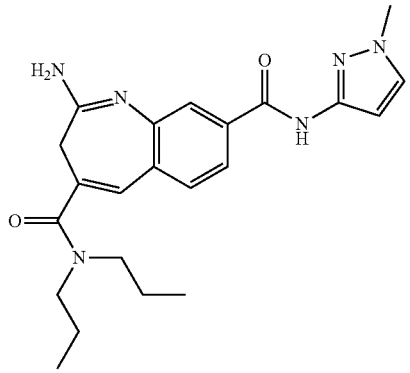 [SMILES: CCCN(CCC)C(=O)C1=Cc2ccc(C(=O)Nc3ccn(C)n3)cc2N=C(N)C1]

The title compound was prepared in analogy to Example 1 by using 1-methylpyrazol-3-amine instead of pyridin-3-amine. Example 37 was obtained as a white solid (38.6 mg). ¹H NMR (400 MHz, CD₃OD) δ ppm=7.90-7.88 (m, 2H), 7.67-7.64 (m, 1H), 7.53 (s, 1H), 7.08 (s, 1H), 6.63 (s, 1H), 4.87 (m, 2H), 3.85 (s, 3H), 3.46 (br.s., 4H), 1.75-1.65 (m, 4H), 0.96-0.93 (m, 6H). MS: calc'd 409 (M+H)⁺. measured 409 (M+H)⁺.

Example 38

2-Amino-N8-oxazol-2-yl-N4,N4-dipropyl-3H-1-benzazepine-4,8-dicarboxamide

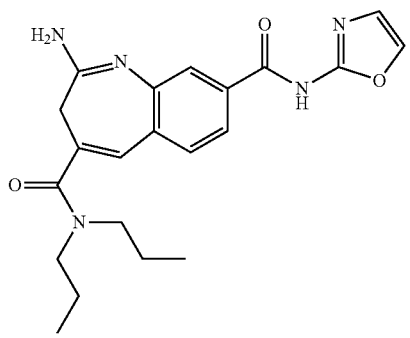 [SMILES: CCCN(CCC)C(=O)C1=Cc2ccc(C(=O)Nc3ncco3)cc2N=C(N)C1]

The title compound was prepared in analogy to Example 1 by using oxazol-2-amine instead of pyridin-3-amine. Example 38 was obtained as a white solid (15.3 mg). ¹H NMR (400 MHz, CD₃OD) δ ppm=7.95 (s, 1H), 7.91 (d, J=8 Hz, 1H), 7.71 (s, 1H), 7.63 (d, J=8 Hz, 1H), 7.17 (s, 1H), 7.06 (s, 1H), 4.87 (m, 2H), 3.46 (br.s., 4H), 1.72-1.67 (m, 4H), 0.96-0.92 (m, 6H). MS: calc'd 396 (M+H)⁺. measured 396 (M+H)⁺.

Example 39

2-Amino-N4-(3-hydroxypropyl)-N4-propyl-N8-(3-pyridyl)-3H-1-benzazepine-4,8-dicarboxamide

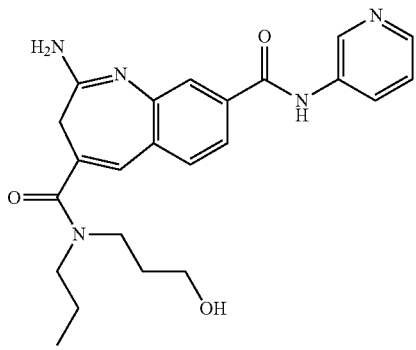 [SMILES: CCCN(CCCO)C(=O)C1=Cc2ccc(C(=O)Nc3cccnc3)cc2N=C(N)C1]

The title compound was prepared in analogy to Example 26 by using pyridin-3-amine instead of m-toluidine. Example 39 was obtained as a yellow solid (4.3 mg). $^1$H NMR (300 MHz, CD$_3$OD) δ ppm=9.63 (brs, 1H), 8.87 (d, J=8.7 Hz, 1H), 8.66 (d, J=5.5 Hz, 1H), 8.18-7.99 (m, 3H), 7.78 (d, J=7.7 Hz, 1H), 7.17 (s, 1H), 3.62 (d, J=7.0 Hz, 4H), 3.49-3.33 (m, 4H), 1.91 (br s., 2H), 1.73 (d, J=7.3 Hz, 2H), 0.97 (br s, 3H). MS: calc'd 422 (M+H)$^+$. measured 422 (M+H)$^+$.

Example 40

2-Amino-N8-(5-methoxy-3-pyridyl)-N4,N4-dipropyl-3H-1-benzazepine-4,8-dicarboxamide

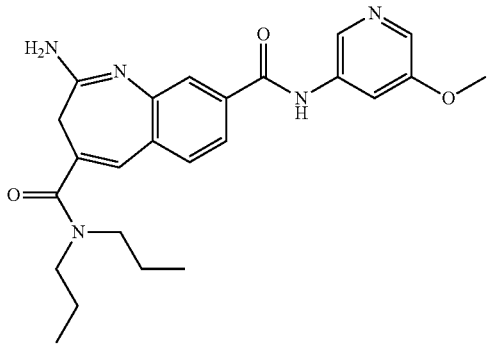 [SMILES: CCCN(CCC)C(=O)C1=Cc2ccc(C(=O)Nc3cncc(OC)c3)cc2N=C(N)C1]

The title compound was prepared in analogy to Example 1 by using 5-methoxypyridin-3-amine instead of pyridin-3-amine. Example 40 was obtained as a white solid (33.6 mg). $^1$H NMR (400 MHz, CD$_3$OD) δ ppm=8.49 (s, 1H), 8.04 (s, 1H), 7.98 (s, 1H), 7.80 (s, 1H), 7.73 (d, J=8 Hz, 1H), 7.55 (d, J=8 Hz, 1H), 6.98 (s, 1H), 4.87 (m, 2H), 3.92 (s, 3H), 3.44 (t, J=8 Hz, 4H), 1.72-1.66 (m, 4H), 0.96-0.90 (m, 6H). MS: calc'd 436 (M+H)$^+$. measured 436 (M+H)$^+$.

Example 41

2-Amino-N8-(m-tolyl)-N4-propyl-N4-prop-2-ynyl-3H-1-benzazepine-4,8-dicarboxamide

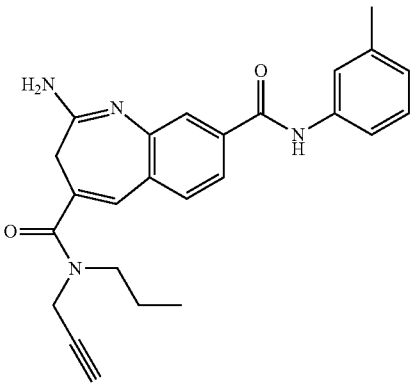 [SMILES: C#CCN(CCC)C(=O)C1=Cc2ccc(C(=O)Nc3cccc(C)c3)cc2N=C(N)C1]

The title compound was prepared in analogy to Example 26 by using N-propylprop-2-yn-1-amine (compound 41A) instead of 3-(propylamino)propan-1-ol. Example 41 was obtained as a white solid (63 mg). $^1$H NMR (400 MHz, CD$_3$OD) δppm=7.99-7.90 (m, 2H), 7.73-7.65 (m, 1H), 7.57-7.45 (m, 2H), 7.26 (t J=7.8 Hz, 2H), 7.05-6.97 (m, 1H), 4.35 (brs, 2H), 3.58 (brs, 2H), 3.39 (s, 2H), 2.90 (brs, 1H), 2.37 (s, 3H), 1.76 (qd, J=7.4, 14.9 Hz, 2H), 0.97 (t J=7.1 Hz, 3H). MS: calc'd 415 (M+H)$^+$. measured 415 (M+H)$^+$.

Preparation of Compound 41A

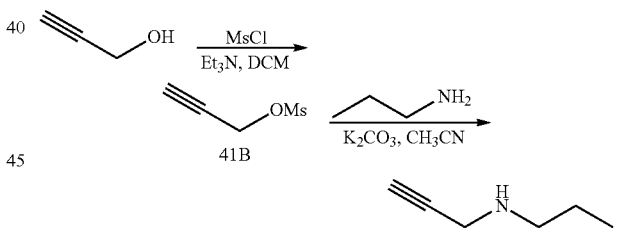

To the solution of prop-2-yn-1-ol (1.0 g, 20.0 mmol) in DCM (30 mL) was added Et$_3$N (3.02 g, 29.9 mmol). Then MsCl (2.3 g, 19.97 mmol) was added dropwise at 0° C. After the reaction mixture was stirred for 1 hr at 0° C., it was poured into water (50 mL). The mixture was extracted with DCM (100 mL). The organic layer was washed with brine (100 mL), dried over Na$_2$SO$_4$, and concentrated in vacuo to give prop-2-yn-1-yl methanesulfonate (compound 41B, 2.2 g, 82%) as a yellow oil, which was dissolved in CH$_3$CN (2 mL) and treated dropwise with a solution of propylamine (1.94 g, 32.8 mmol) in CH$_3$CN (30 mL) at 0° C. After the mixture was stirred at 25° C. for 12 hrs, it was poured into water (50 mL) and extracted with DCM (100 mL×2). The organic layers were washed with brine (100 mL), dried over Na$_2$SO$_4$, and concentrated in vacuo to give N-propylprop-2-yn-1-amine (compound 41A, 0.5 g, 31.4%) as a yellow oil.

Example 42

2-Amino-N4,N4-dibutyl-N8-(m-tolyl)-3H-1-benzazepine-4,8-dicarboxamide

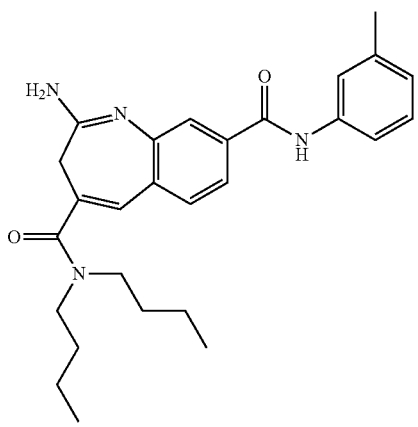 [SMILES: CCCCN(CCCC)C(=O)C1=Cc2ccc(C(=O)Nc3cccc(C)c3)cc2N=C(N)C1]

The title compound was prepared in analogy to Example 26 by using N-butylbutan-1-amine instead of 3-(propylamino)propan-1-ol. Example 42 was obtained as a white solid (33.6 mg). $^1$H NMR (400 MHz, CD$_3$OD) δ ppm=7.96-7.94 (m, 2H), 7.73-7.65 (m, 1H), 7.57-7.46 (m, 2H), 7.30-7.22 (m, 1H), 7.12 (s, 1H), 7.02 (d, J=7.4 Hz, 1H), 3.50 (br s, 4H), 3.37 (s, 2H), 2.37 (s, 3H), 1.66 (q, J=7.6 Hz, 4H), 1.49-1.25 (m, 4H), 0.97 (br s, 6H). MS: calc'd 447 (M+H)$^+$. measured 447 (M+H)$^+$.

Example 43

2-Amino-N8-[3-(aminomethyl)-5-methyl-phenyl]-N4,N4-dipropyl-3H-1-benzazepine-4,8-dicarboxamide

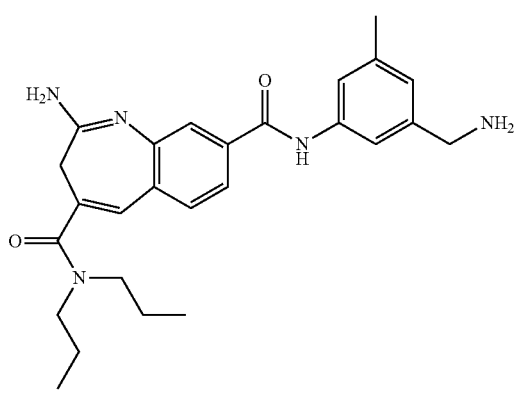 [SMILES: CCCN(CCC)C(=O)C1=Cc2ccc(C(=O)Nc3cc(C)cc(CN)c3)cc2N=C(N)C1]

The title compound was prepared in analogy to Example 1 by using tert-butyl 3-amino-5-methylbenzylcarbamate (compound 43A) instead of pyridin-3-amine. Example 43 was obtained as a white solid (45 mg). $^1$H NMR (400 MHz, CD$_3$OD) δ ppm=8.03 (s, 1H), 8.00 (dd, J=1.63, 8.16 Hz, 1H), 7.77 (s, 1H), 7.73 (d, J=8.28 Hz, 1H), 7.57 (br. s., 1H), 7.14 (d, J=3.89 Hz, 2H), 4.13 (s, 2H), 3.49 (br. s., 4H), 3.41 (s, 2H), 2.43 (s, 3H), 1.72 (sxt, J=7.43 Hz, 4H), 0.87-1.08 (m, 6H). MS: calc'd 448 (M+H)$^+$. measured 448 (M+H)$^+$.

Preparation of tert-butyl 3-amino-5-methylbenzylcarbamate (Compound 43A)

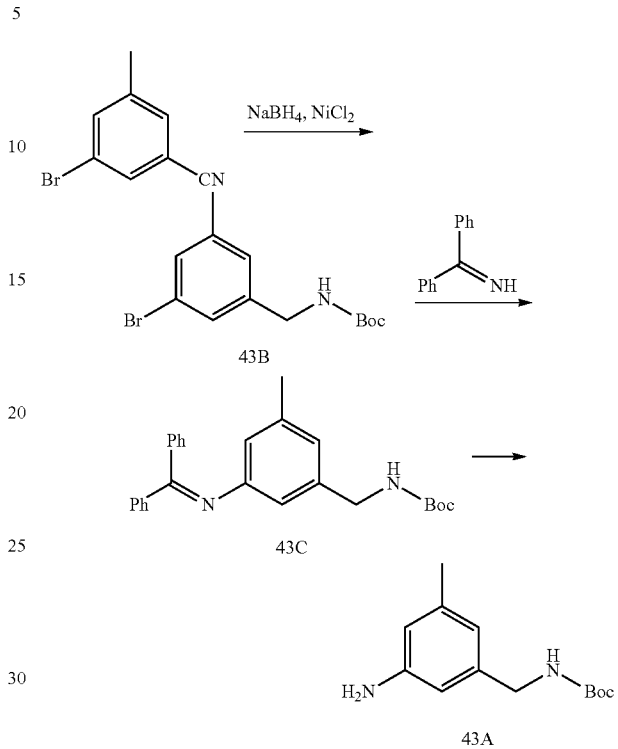

a) Preparation of Compound 43B

To a solution of 3-bromo-5-methylbenzonitrile (1.0 g, 5.12 mmol) in MeOH (40 mL) was added NiCl$_2$.6H$_2$O (121 mg, 0.51 mmol), Boc$_2$O (1.35 g, 6.20 mmol) and NaBH$_4$ (780 mg, 20.5 mmol) at −20° C. Then the mixture was stirred for 2 hrs at 0-10° C. The reaction solution was quenched with sat. NH$_4$Cl (120 mL), diluted with H$_2$O (200 mL) and extracted with EA (100 mL×3). The combined organic layers were washed by brine (50 mL×2), dried over Na$_2$SO$_4$ and concentrated to give tert-butyl 3-bromo-5-methylbenzylcarbamate (compound 43B, 1.3 g, 86.7%) as a white solid. MS: calc'd 300 (M+H)$^+$. measured 300 (M+H)$^+$.

b) Preparation of compound 43C

To a solution of tert-butyl 3-bromo-5-methylbenzylcarbamate (compound 43B, 2.0 g, 6.7 mmol) and diphenylmethanimine (compound 43C, 1.44 g, 8.0 mmol) in toluene (50 mL) was added Cs$_2$CO$_3$ (4.3 g, 13.4 mmol), BINAP (833 mg, 1.34 mmol) and Pd(OAc)$_2$ (150 mg, 0.67 mol) at 20° C. After the reaction mixture was stirred at 90° C. for 16 hrs, it was quenched with sat. NH$_4$Cl (50 mL), diluted with H$_2$O (100 mL) and extracted with EA (50 mL×3). The combined organic layers were washed with brine (30 mL×2), dried over Na$_2$SO$_4$ and concentrated to give the crude product. The crude product was purified by silica gel column chromatography (PE:EA=10:1) to give tert-butyl 3-((diphenylmethylene)amino)-5-methylbenzylcarbamate (compound 43C, 1.2 g, 46.1%) as yellow oil. MS: calc'd 401 (M+H)$^+$. measured 401 (M+H)$^+$.

c) Preparation of Compound 43A

To a solution of tert-butyl 3-((diphenylmethylene)amino)-5-methylbenzylcarbamate (compound 43C, 1.2 g, 3.0 mmol)

in MeOH (50 mL) was added NH$_2$OH HCl (639 mg, 9.0 mmol), NaOAc (1.2 g, 15.0 mmol) at 0° C. Then the mixture was stirred at 15° C. for 16 hrs. The reaction solution was quenched with sat. NH$_4$Cl (80 mL), diluted with H$_2$O (100 mL), and extracted with EA (50 mL×3). The combined organic layers were washed with brine (30 mL×2), dried over Na$_2$SO$_4$ and concentrated to give the crude product. The crude product was purified by silica gel column chromatography (PE:EA=5:1) to give tert-butyl 3-amino-5-methylbenzylcarbamate (compound 43A, 500 mg, 70%) as yellow oil. MS: calc'd 237 (M+H)$^+$. measured 237 (M+H)$^+$.

Example 44

2-Amino-N8-(5-ethoxy-3-pyridyl)-N4,N4-dipropyl-3H-1-benzazepine-4,8-dicarboxamide

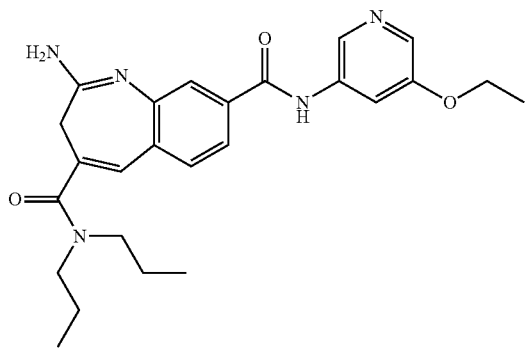 [SMILES: CCCN(CCC)C(=O)C1=Cc2ccc(C(=O)Nc3cncc(OCC)c3)cc2N=C(N)C1]

The title compound was prepared in analogy to Example 1 by using 5-ethoxypyridin-3-amine instead of pyridin-3-amine. Example 44 was obtained as a white solid (44.5 mg). $^1$H NMR (400 MHz, CD$_3$OD) δ ppm=8.48 (s, 1H), 8.02 (s, 1H), 7.95 (s, 1H), 7.80-7.79 (m, 1H), 7.73-7.70 (m, 1H), 7.56-7.53 (s, 1H), 6.98-6.97 (m, 1H), 4.85 (m, 2H), 4.16 (q, J=8 Hz, 2H), 3.44 (t, J=8 Hz, 4H), 1.72-1.66 (m, 4H), 1.45 (t, J=8 Hz, 3H), 0.96-0.91 (m, 6H). MS: calc'd 450 (M+H)$^+$. measured 450 (M+H)$^+$.

Example 45

2-Amino-N8-[3-[2-(2-aminoethoxy)ethoxy]phenyl]-N4,N4-dipropyl-3H-1-benzazepine-4,8-dicarboxamide

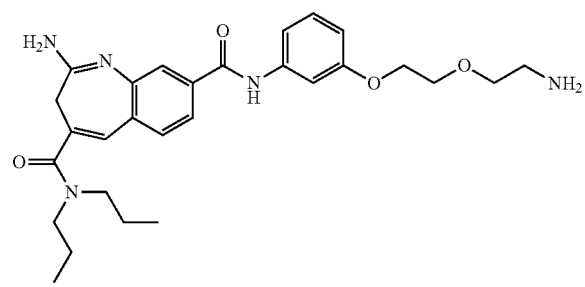 [SMILES: CCCN(CCC)C(=O)C1=Cc2ccc(C(=O)Nc3cccc(OCCOCCN)c3)cc2N=C(N)C1]

The title compound was prepared in analogy to Example 1 by using tert-butyl N4-[2-[2-(3-aminophenoxy)ethoxy]ethyl]carbamate (compound 45C) instead of pyridin-3-amine. Example 45 was obtained as a white solid (52 mg). $^1$H NMR (400 MHz, CD$_3$OD) δ ppm=7.80 (s, 1H), 7.74 (d, J=8 Hz, 1H), 7.58 (t, J=4 Hz, 1H), 7.55 (s, 1H), 7.28 (t, J=8 Hz, 1H), 7.18 (d, J=8 Hz, 1H), 6.99 (s, 1H), 6.77 (d, J=8 Hz, 1H), 4.84 (m, 2H), 4.23-4.21 (m, 2H), 3.92-3.90 (m, 2H), 3.81-3.78 (m, 2H), 3.45 (t, J=8 Hz, 4H), 3.18-3.15 (m, 2H), 1.74-1.65 (m, 4H), 0.93 (br, 6H). MS: calc'd 508 (M+H)$^+$. measured 508 (M+H)$^+$.

Preparation of tert-butyl N-[2-[2-(3-aminophenoxy)ethoxy]ethyl]carbamate (compound 45C)

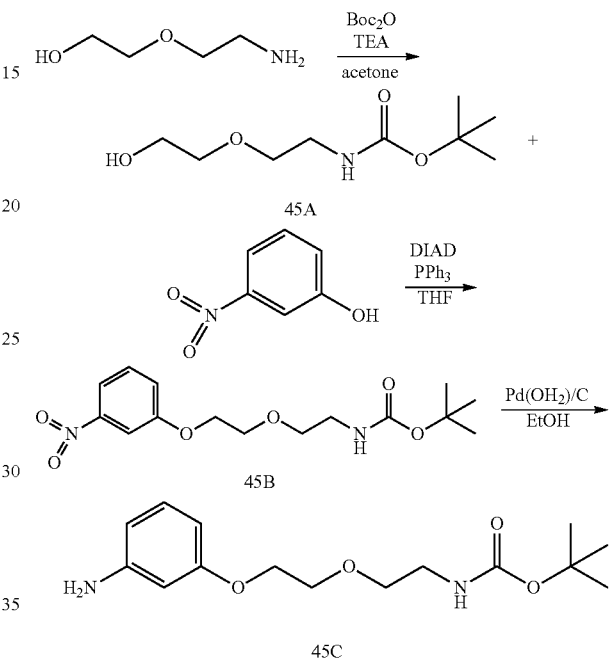

a) Preparation of Compound 45A

To a stirred solution of 2-(2-aminoethoxy)ethanol (1 g, 943 μL, 9.5 mmol), TEA (1.44 g, 1.99 mL, 14.3 mmol) in acetone (10 mL) was added (Boc)$_2$O (3.11 g, 3.31 mL, 14.3 mmol) at ambient temperature. After the mixture was stirred for 14 hrs, it was concentrated to give a pale yellow oil, which was purified by silica gel column to give 1.6 g tert-butyl N4-[2-(2-hydroxyethoxy)ethyl]carbamate (compound 45A) as pale yellow oil. MS: calc'd 206 (M+H)$^+$. measured 206 (M+H)$^+$.

b) Preparation of Compound 45B

To a stirred solution of 3-nitrophenol (450 mg, 3.23 mmol), tert-butyl N4-[2-(2-hydroxyethoxy)ethyl]carbamate (797 mg, 3.88 mmol) in THF (12 mL) was added triphenylphosphine (1.27 g, 4.85 mmol) and (E)-diisopropyl diazene-1,2-dicarboxylate (981 mg, 955 μL, 4.85 mmol) at r.t. After the reaction mixture was stirred at r.t. for 3 hrs, the solvent was removed in vacuo to give a yellow oil, which was purified by silica gel column to give tert-butyl N-[2-[2-(3-nitrophenoxy)ethoxylethyl]carbamate (compound 45B, 2 g) as pale yellow oil. MS: calc'd 327 (M+H)$^+$. measured 327 (M+H)$^+$.

c) Preparation of Compound 45C

To a stirred solution of tert-butyl N-[2-[2-(3-nitrophenoxy)ethoxylethyl]carbamate (2 g, 6.13 mmol) in EtOH (15 mL) was added 20% Pd(OH)₂ on carbon (0.5 g). After the reaction system was vacuumed and backfilled with hydrogen 3 times, the reaction mixture was stirred at room temperature with a hydrogen balloon for 6 hrs. The mixture was filtered through celite and the filtrate was concentrated to give N-[2-[2-(3-aminophenoxy)ethoxyethyl]carbamate (compound 45C, 1.88 g) as a purple oil. MS: calc'd 297 (M+H)⁺. measured 297 (M+H)⁺.

Example 46

2-Amino-N8-[5-(5-aminopentoxy)-3-pyridyl]-N4,N4-dipropyl-3H-1-benzazepine-4,8-dicarboxamide

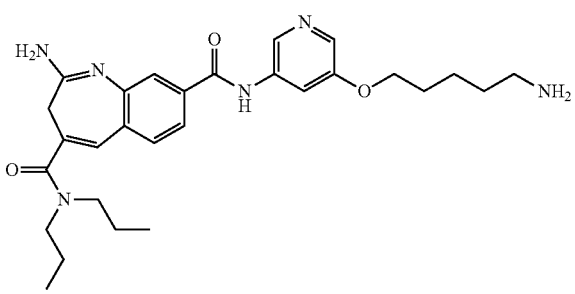 [SMILES: CCCN(CCC)C(=O)C1=Cc2ccc(C(=O)Nc3cncc(OCCCCCN)c3)cc2N=C(N)C1]

The title compound was prepared in analogy to Example 1 by using tert-butyl N-[5-[(5-amino-3-pyridyl)oxy]pentyl]carbamate (compound 46C) instead of pyridin-3-amine. Example 46 was obtained as a white solid (22 mg). ¹H NMR (400 MHz, CD₃OD) δ ppm=8.43 (s, 1H), 8.06 (s, 1H), 8.02 (s, 1H), 7.80 (s, 1H), 7.72 (s, 1H), 7.57-7.55 (m, 1H), 6.98 (s, 1H), 4.88 (m, 2H), 4.16-4.13 (m, 2H), 3.46-3.42 (m, 4H), 2.99-2.96 (m, 2H), 1.80-1.59 (m, 10H), 0.97-0.93 (br, 6H). MS: calc'd 507 (M+H)⁺. measured 507 (M+H)⁺.

Preparation of tert-butyl N-[5-[(5-amino-3-pyridyl)oxy]pentyl]carbamate (compound 46C)

The title compound was prepared in analogy to compound 45C by using 5-aminopentan-1-ol instead of 2-(2-aminoethoxy)ethanol and 5-nitropyridin-3-ol instead of 3-nitrophenol.

Example 47

2-Amino-N8-[3-[2-(2-aminoethoxy)ethoxymethyl]phenyl]-N4,N4-dipropyl-3H-1-benzazepine-4,8-dicarboxamide

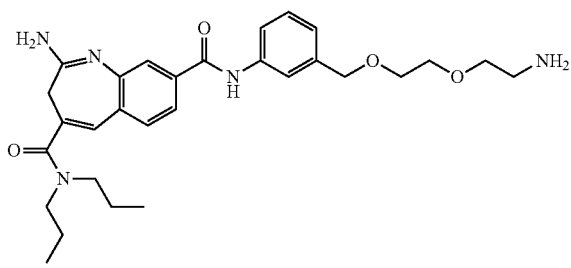 [SMILES: CCCN(CCC)C(=O)C1=Cc2ccc(C(=O)Nc3cccc(COCCOCCN)c3)cc2N=C(N)C1]

The title compound was prepared in analogy to Example 1 by using tert-butyl (2-(2-((3-aminobenzyl)oxy)ethoxy) ethyl)carbamate (compound 47A) instead of pyridin-3-amine. Example 47 was obtained as a white solid (78 mg). ¹H NMR (400 MHz, CD₃OD) δ ppm=7.97-7.85 (m, 2H), 7.81 (s, 1H), 7.66-7.58 (m, 1H), 7.57-7.48 (m, 1H), 7.35-7.25 (m, 1H), 7.14-7.06 (m, 1H), 7.03 (s, 1H), 4.53 (s, 2H), 3.71-3.59 (m, 6H), 3.38 (br. s., 4H), 3.23 (td, J=1.6, 3.3 Hz, 2H), 3.07 (t, J=4.8 Hz, 2H), 1.62 (sxt, J=7.4 Hz, 4H), 0.86 (br. s., 6H). MS: calc'd 522 (M+H)⁺. measured 522 (M+H)⁺.

Preparation of tert-butyl (2-(2-((3-aminobenzyl)oxy)ethoxy)ethyl)carbamate (compound 47A)

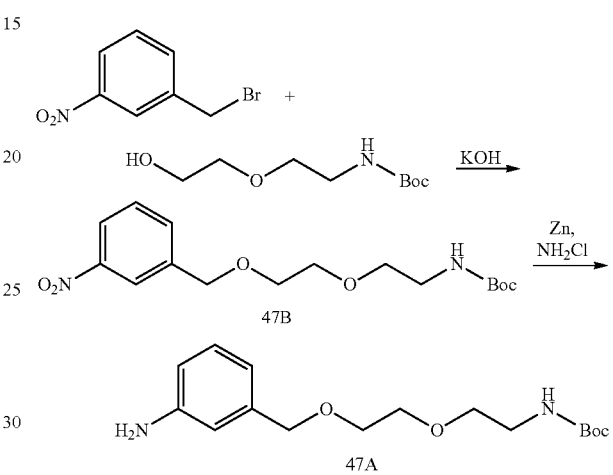

a) Preparation of Compound 47B

To the solution of 1-(bromomethyl)-3-nitrobenzene (1.0 g, 4.63 mmol) and tert-butyl (2-(2-hydroxyethoxy)ethyl)carbamate (0.95 g, 4.63 mmol) in DMF (40 mL) was added KOH (518 mg, 9.25 mmol). After the solution was stirred at 50° C. for 15 hrs, it was poured into water (100 mL) and extracted with EtOAc (50 mL×3). The combined organic layers were washed with brine (50 mL×3), dried over Na₂SO₄ and concentrated in vacuo. The residue was purified through silica gel column chromatography (DCM/MeOH=200/1~80/1) to give tert-butyl (2-(2-((3-nitrobenzyl)oxy)ethoxy)ethyl)carbamate (compound 47B, 400 mg, 25%) as a yellow oil. MS: calc'd 341 (M+H)⁺. measured 341 (M+H)⁺.

b) Preparation of Compound 47A

To the solution of tert-butyl(2-(2-((3-nitrobenzyl)oxy)ethoxy)ethyl)carbamate (compound 47B, 0.4 g, 1.2 mmol) in EtOH/H₂O (25/2.5 mL) were added NH₄Cl (377 mg, 7.1 mmol) and Zn powder (1.91 g, 29.4 mmol). After the solution was stirred at 80° C. for 3 hrs, it was filtered and the filtrate was concentrated in vacuo. The residue was dissolved in DCM (100 mL), washed with brine (50 mL×2), dried over Na₂SO₄ and concentrated in vacuo to give tert-butyl (2-(2-((3-aminobenzyl)oxy)ethoxy)ethyl)carbamate (compound 47A, 365 mg, 100%) as a yellow oil, which was used directly for the next step. MS: calc'd 311 (M+H)⁺. measured 311 (M+H)⁺.

Example 48

2-Amino-N8-[5-(3-aminoprop-1-ynyl)-3-pyridyl]-N4,N4-dipropyl-3H-1-benzazepine-4,8-dicarboxamide

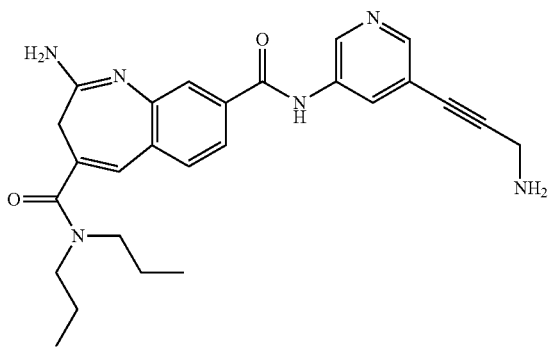 [SMILES: CCCN(CCC)C(=O)C1=Cc2ccc(C(=O)Nc3cncc(C#CCN)c3)cc2N=C(N)C1]

The title compound was prepared in analogy to Example 1 by using tert-butyl N-[3-(5-amino-3-pyridyl)prop-2-ynyl]carbamate (compound 48A) instead of pyridin-3-amine. Example 48 was obtained as a white solid (0.3 mg). $^1$H NMR (400 MHz, CD$_3$OD) δ ppm=8.82 (s, 1H), 8.49 (s, 1H), 8.40 (s, 1H), 7.76 (s, 1H), 7.66 (d, J=8 Hz, 1H), 7.52 (d, J=8 Hz, 1H), 6.94 (s, 1H), 4.87 (m, 2H), 4.00 (s, 2H), 3.49-3.42 (m, 4H), 1.70-1.66 (m, 4H), 0.96-0.88 (m, 6H). MS: calc'd 459 (M+H)$^+$. measured 459 (M+H)$^+$.

Preparation of tert-butyl N-[3-(5-amino-3-pyridyl)prop-2-ynyl]carbamate (compound 48A)

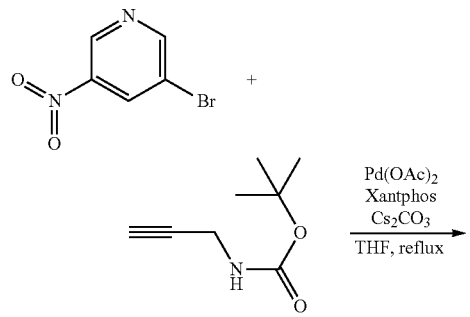

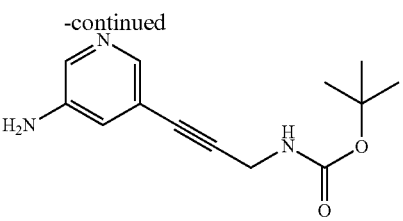

48A a) Preparation of Compound 48B

To a solution of 3-bromo-5-nitropyridine (1 g, 4.93 mmol) in THF (30 mL) was added successively tert-butyl prop-2-yn-1-ylcarbamate (1.15 g, 7.39 mmol), Pd(OAc)$_2$ (55 mg, 246 μmol), 4,5-bis(diphenylphosphino)-9,9-dimethylxanthene (285 mg, 493 μmol), and Cs$_2$CO$_3$ (4.82 g, 14.80 mmol). After the mixture was degassed and recharged with argon for five times, it was heated to reflux for 4.5 hrs. The reaction mixture was filtered through celite and the filtrate was concentrated to give a dark oil, which was purified by silica gel chromatography (eluting with EA/PE=0-20%~30%) to give a brown oil. The oil was triturated with PE to give tert-butyl N-[3-(5-nitro-3-pyridyl)prop-2-ynyl]carbamate (compound 48B, 1 g) as brown solid. MS: calc'd 278 (M+H)$^+$. measured 278 (M+H)$^+$.

b) Preparation of Compound 48A

To a solution of tert-butyl (3-(5-nitropyridin-3-yl)prop-2-yn-1-yl)carbamate (400 mg, 1.44 mmol) in THF (5 mL) and EtOH (0.5 mL) was added stannous chloride (1.3 g, 329 μL, 6.86 mmol) at room temperature. After the reaction mixture was stirred at room tempearture for 6 hrs, it was treated with 20 mL of 25% aqueous KOH and 25 mL DCM. A precipitate was formed and then filtered. The filtrate was extracted with DCM (25 mL×2). The combined organic layers were washed with brine (20 mL×3), dried over Na$_2$SO$_4$ and concentrated to give a brown oil, which was purified by silica gel chromatography to give tert-butyl N-[3-(5-amino-3-pyridyl)prop-2-ynyl]carbamate (compound 48A, 28 mg) as a yellow oil. MS: calc'd 248 (M+H)$^+$. measured 248 (M+H)$^+$.

Example 49

2-Amino-N8-[5-(3-aminoprop-1-ynyl)-3-pyridyl]-N4,N4-dipropyl-3H-1-benzazepine-4,8-dicarboxamide

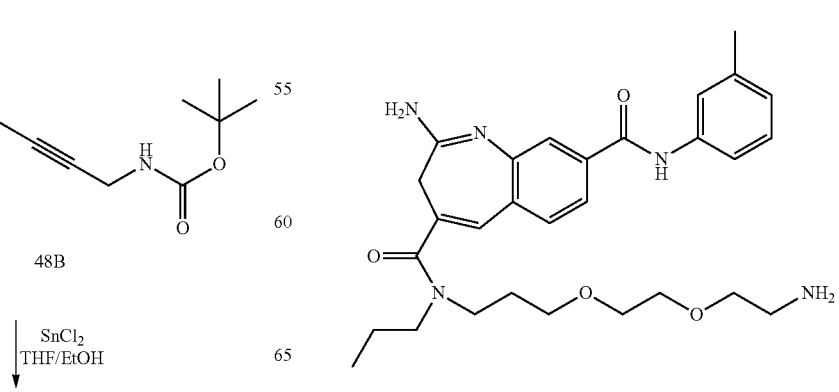

The title compound was prepared in analogy to Example 26 by using tert-butyl (2-(2-(3-(propylamino)propoxy)ethoxy)ethyl)carbamate (compound 49A) instead of 3-(propylamino)-propan-1-ol. Example 49 was obtained as a yellow solid. (74.5 mg). $^1$H NMR (400 MHz, CD$_3$OD) δ=8.02-7.94 (m, 2H), 7.77-7.69 (m, 1H), 7.60-7.49 (m, 2H), 7.28 (t, J=7.8 Hz, 1H), 7.16 (s, 1H), 7.03 (d, J=7.7 Hz, 1H), 3.81-3.45 (m, 12H), 3.41 (s, 2H), 3.23-2.98 (m, 2H), 2.39 (s, 3H), 2.04-1.93 (m, 2H), 1.73 (sxt, J=7.4 Hz, 2H), 0.96 (br. s., 3H). MS: calc'd 522 (M+H)$^+$. measured 522 (M+H)$^+$.

Preparation of tert-butyl (2-(2-(3-(propylamino)propoxy)ethoxy)ethyl)carbamate (Compound 49A)

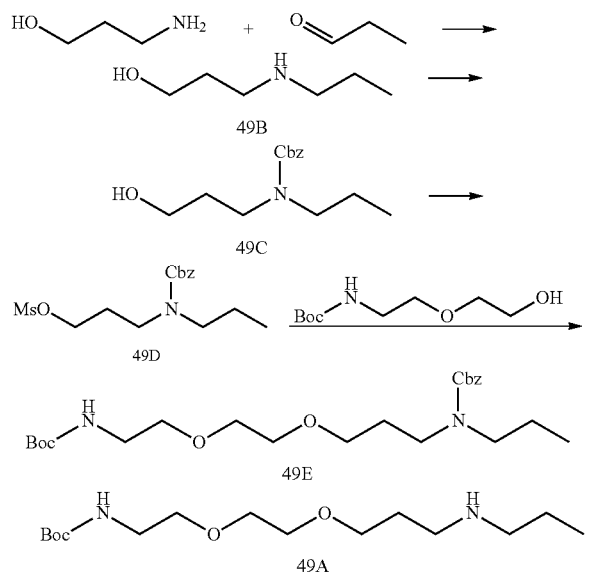

a) Preparation of Compound 49B

To the solution of 3-aminopropan-1-ol (1.0 g, 13.3 mmol) and propionaldehyde (0.77 g, 13.3 mmol) in MeOH (20 mL) was added MgSO$_4$ (6.4 g, 53.3 mmol). After the reaction mixture was stirred at 25° C. for 12 hrs, the undissolved material was filtered and the filtrate was treated with NaBH$_4$ (556 mg, 14.6 mmol) under ice-bath. Then the mixture was stirred at 25° C. for 1 h. The reaction solution was concentrated in vacuo and the residue was dissolved in DCM (100 mL) and stirred for 5 min. The undissolved material was filtered and the filtrate was concentrated in vacuo to give 3-(propylamino)propan-1-ol (compound 49B, 1.0 g, 64.1%) as a yellow oil, which was used for the next step directly.

b) Preparation of Compound 49C

To the solution of 3-(propylamino)propan-1-ol (compound 49B, 1.0 g, 8.53 mmol) in THF/H$_2$O (20/10 mL) was added NaHCO$_3$ (1.43 g, 17.06 mmol). Then Cbz-Cl (1.45 g, 8.53 mmol) was added dropwise under ice-bath. After the reaction mixture was stirred at 25° C. for 12 hrs, it was poured into water (50 mL) and extracted with EtOAc (50 mL×3). The combined organic layers were washed with brine (100 mL), dried over Na$_2$SO$_4$ and concentrated in vacuo. The residue was purified through silica gel column chromatography (PE/EtOAc=10/1~2/1) to give benzyl (3-hydroxypropyl)(propyl)carbamate (compound 49C, 0.7 g, 32.7%) as a colorless oil. MS: calc'd 252 (M+H)$^+$. measured 252 (M+H)$^+$.

c) Preparation of Compound 49D

To the solution of benzyl (3-hydroxypropyl)(propyl)carbamate (compound 49C, 0.7 g, 2.78 mmol) in DCM (20 mL) was added TEA (416 mg, 4.12 mmol). Then MsCl (319 mg, 2.78 mmol) was added under ice-bath. After the reaction mixture was stirred at 25° C. for 3 hrs, it was diluted with DCM (50 mL). The solution was washed with aq. NaHCO$_3$ (50 mL×3) and brine (100 mL). The organic layer was dried over Na$_2$SO$_4$ and concentrated in vacuo to give 3-(((benzyloxy)carbonyl)(propyl)amino)propyl methanesulfonate (compound 49D, 0.9 g, 98.3%) as a yellow oil, which was used for the next step directly.

d) Preparation of Compound 49E

To the solution of 3-(((benzyloxy)carbonyl)(propyl)amino)propyl methanesulfonate (compound 49D, 500 mg, 1.52 mmol) and tert-butyl (2-(2-hydroxyethoxy)ethyl)carbamate (311 mg, 1.52 mmol) in DCM (5 mL) was added TBAI (673 mg, 1.82 mmol). Then 30% of aq. NaOH (5 mL) was added. The mixture was stirred at 25° C. for 15 hrs. The reaction solution was then poured into 10% of citric acid (100 mL) and extracted with EtOAc (30 mL×2). The combined organic layers were washed with brine (100 mL), dried over Na$_2$SO$_4$, and concentrated in vacuo. The residue was purified through silica gel column chromatography (DCM/MeOH=200/1-80/1) to give benzyl (2,2-dimethyl-4-oxo-3,8,11-trioxa-5-azatetradecan-14-yl)(propyl)carbamate (compound 49E, 300 mg, 45%) as a yellow oil. MS: calc'd 439 (M+H)$^+$. measured 439 (M+H)$^+$ e) Preparation of Compound 49A To the solution of benzyl (2,2-dimethyl-4-oxo-3,8,11-trioxa-5-azatetradecan-14-yl)(propyl)carbamate (compound 49E, 300 mg, 0.73 mmol) in MeOH (20 mL) was added Pd/C (300 mg, 10%, wet). Then the mixture was stirred under 50 psi H$_2$ at 30° C. for 12 hrs. The reaction mixture was filtered and the filtrate was concentrated in vacuo to give tert-butyl (2-(2-(3-(propylamino)propoxy)ethoxy)ethyl)carbamate (compound 49A, 187 mg, 84%) as a yellow oil, which was used directly in the next step. MS: calc'd 305 (M+H)$^+$. measured 305 (M+H)$^+$ Example 50

2-Amino-N8-[5-(3-aminopropyl)-3-pyridyl]-N4,N4-dipropyl-3H-1-benzazepine-4,8-dicarboxamide

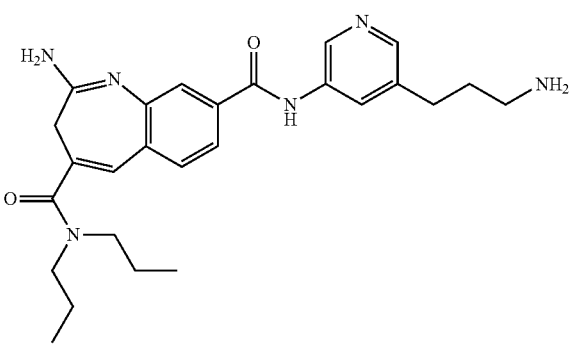 [SMILES: CCCN(CCC)C(=O)C1=Cc2ccc(C(=O)Nc3cncc(CCCN)c3)cc2N=C(N)C1]

The title compound was prepared in analogy to Example 1 by using tert-butyl N-[3-(5-amino-3-pyridyl)propyl]carbamate (compound 50A) instead of pyridin-3-amine. Example 50 was obtained as a white solid (30.4 mg). $^1$H NMR (400 MHz, CD$_3$OD) δ ppm=8.67 (s, 1H), 8.30 (s, 1H), 8.22 (s, 1H), 7.74 (s, 1H), 7.63 (d, J=8 Hz, 1H), 7.50 (d, J=8 Hz, 1H), 6.93 (s, 1H), 4.88 (m, 2H), 3.45-3.42 (m, 4H), 3.00 (t, J=8 Hz, 2H), 2.81 (t, J=8 Hz, 2H), 2.07-1.99 (m, 2H), 1.71-1.66 (m, 4H), 0.97-0.88 (m, 6H). MS: calc'd 463 (M+H)$^+$. measured 463 (M+H)$^+$.

Preparation of tert-butyl N-[3-(5-amino-3-pyridyl)propyl]carbamate (Compound 50A)

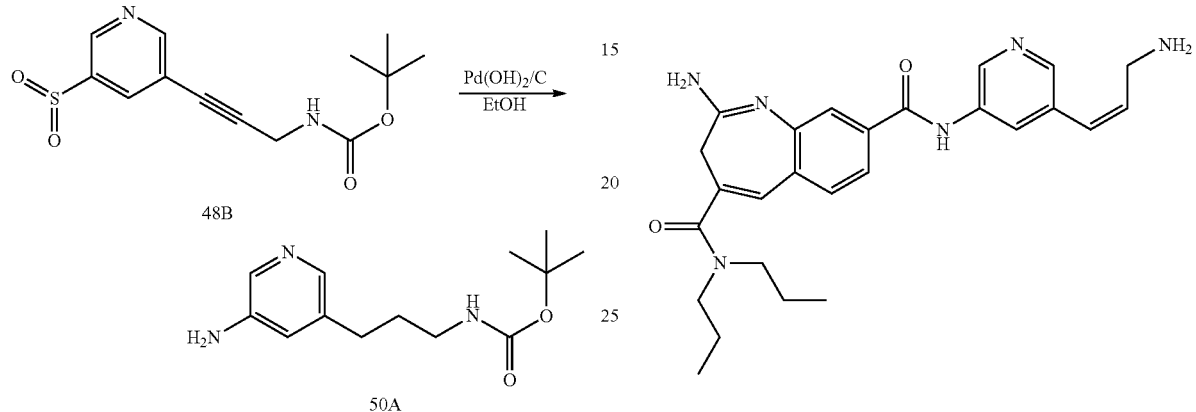

To a flask was added tert-butyl (3-(5-nitropyridin-3-yl) prop-2-yn-1-yl)carbamate (compound 48B) (100 mg, 0.361 mmol), ethanol (5 mL) and palladium hydroxide on carbon (15 mg, 0.107 mmol). After the mixture was degassed and recharged with hydrogen for five times, it was stirred at room temperature with a hydrogen balloon for 4 hrs. The reaction mixture was filtered through celite and the filtrate was concentrated to give crude tert-butyl N-[3-(5-amino-3-pyridyl)propyl]carbamate (compound 50A, 95 mg) as a brown sticky oil. MS: calc'd 252 (M+H)$^+$. measured 252 (M+H)$^+$.

Example 51

2-Amino-N8-(m-tolyl)-N4-propyl-N4-(3,3,3-trifluoropropyl)-3H-1-benzazepine-4,8-dicarboxamide

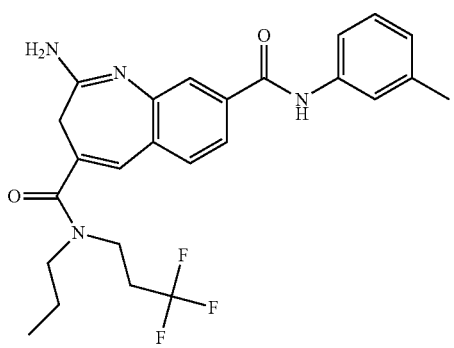 [SMILES: CCCN(CCC(F)(F)F)C(=O)C1=Cc2ccc(C(=O)Nc3cccc(C)c3)cc2N=C(N)C1]

The title compound was prepared in analogy to Example 26 by using 3,3,3-trifluoro-N-propyl-propan-1-amine instead of 3-(propylamino)propan-1-ol. Example 51 was obtained as a white solid (3 mg). $^1$H NMR (400 MHz, CD$_3$OD) δ ppm=7.85-7.82 (m, 2H), 7.61 (d, J=8 Hz, 1H), 7.53 (s, 1H), 7.49 (d, J=8 Hz, 1H), 7.26 (t, J=8 Hz, 1H), 7.08 (s, 1H), 7.01 (d, J=8 Hz, 1H), 4.87 (m, 2H), 3.75 (brs, 2H), 3.52-3.48 (m, 2H), 2.65-2.59 (m, 2H), 2.37 (s, 3H), 1.75-1.66 (m, 2H), 0.93 (brs, 3H), MS: calc'd 473 (M+H)$^+$. measured 473 (M+H)$^+$.

Example 52

2-Amino-N8-[5-[(Z)-3-aminoprop-1-enyl]-3-pyridyl]-N4,N4-dipropyl-3H-1-benzazepine-4,8-dicarboxamide The title compound was prepared in analogy to Example 1 by using tert-butyl N—[(Z)-3-(5-amino-3-pyridyl)allyl] carbamate (compound 52A) instead of pyridin-3-amine. Example 52 was obtained as a white solid (35 mg). $^1$H NMR (400 MHz, CD$_3$OD) δ ppm=8.75 (s, 1H), 8.35 (s, 1H), 8.27 (s, 1H), 7.80 (s, 1H), 7.70 (d, J=8 Hz, 1H), 7.54 (d, J=8 Hz, 1H), 6.97 (s, 1H), 6.88 (d, J=12 Hz, 1H), 5.98-5.92 (m, 1H), 4.87 (m, 2H), 3.93 (d, J=8 Hz, 2H), 3.46-3.42 (m, 4H), 1.72-1.66 (m, 4H), 0.97-0.90 (m, 6H). MS: calc'd 461 (M+H)$^+$. measured 461 (M+H)$^+$.

Preparation of tert-butyl N—[(Z)-3-(5-amino-3-pyridyl)allyl]carbamate (Compound 52A)

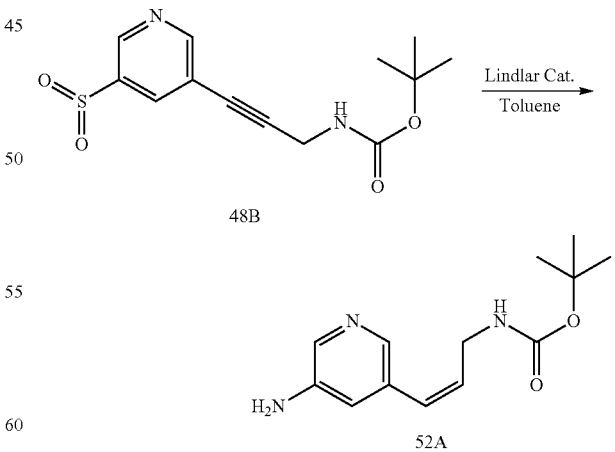

To a 25 mL flask was added tert-butyl (3-(5-nitropyridin-3-yl)prop-2-yn-1-yl)carbamate (compound 48B) (400 mg, 1.44 mmol), Lindlar catalyst (200 mg, 968 µmol) and toluene (10 mL). After the mixture was degassed and recharged with hydrogen for five times, it was stirred at r.t.

with a hydrogen balloon overnight. The mixture was filtered through celite and the filtrate was concentrated to give the crude tert-butyl N—[(Z)-3-(5-amino-3-pyridyl)allyl]carbamate (compound 52A) as sticky brown oil, which was used directly in the next step. MS: calc'd 250 (M+H)⁺. measured 250 (M+H)⁺.

Example 53

2-Amino-N4-(cyclopropylmethyl)-N8-(m-tolyl)-N4-propyl-3H-1-benzazepine-4,8-dicarboxamide

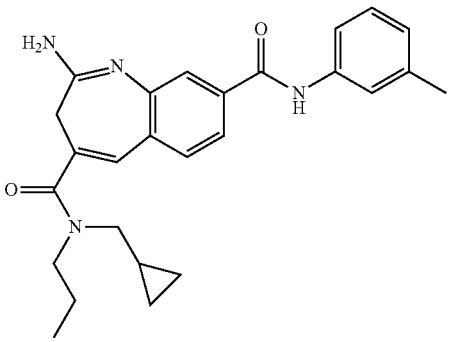 [SMILES: CCCN(CC1CC1)C(=O)C1=Cc2ccc(C(=O)Nc3cccc(C)c3)cc2N=C(N)C1]

The title compound was prepared in analogy to Example 26 by using N-(cyclopropylmethyl)propan-1-amine instead of 3-(propylamino)propan-1-ol. Example 53 was obtained as a white solid (18.3 mg). ¹H NMR (400 MHz, CD₃OD) δ ppm=7.77 (s, 1H), 7.71 (d, J=8 Hz, 1H), 7.55-7.53 (m, 2H), 7.49 (d, J=8 Hz, 1H), 7.25 (t, J=8 Hz, 1H), 7.00-7.69 (m, 2H), 4.87 (m, 2H), 3.55 (t, J=8 Hz, 2H), 3.39 (d, J=8 Hz, 2H), 2.37 (s, 3H), 1.75-1.70 (m, 2H), 1.09 (brs, 1H), 0.94 (br s, 3H), 0.62-0.57 (m, 2H), 0.28 (br s, 2H). MS: calc'd 431 (M+H)⁺. measured 431 (M+H)⁺.

Example 54

2-Amino-N8-[3-(2-aminoethyl)phenyl]-N4,N4-dipropyl-3H-1-benzazepine-4,8-dicarboxamide

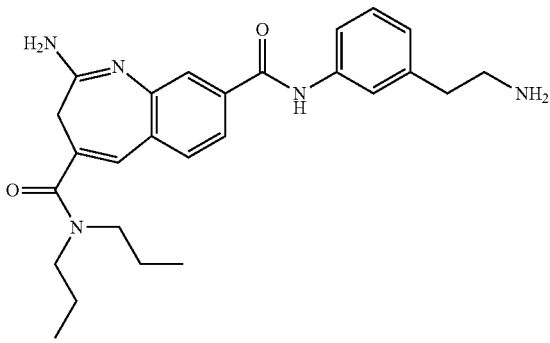 [SMILES: CCCN(CCC)C(=O)C1=Cc2ccc(C(=O)Nc3cccc(CCN)c3)cc2N=C(N)C1]

The title compound was prepared in analogy to Example 1 by using tert-butyl 3-aminophenethylcarbamate instead of pyridin-3-amine. Example 54 was obtained as a yellow solid (20 mg). 1H NMR (400 MHz, CD₃OD) δ ppm=7.69-7.95 (m, 3H), 7.50-7.67 (m, 2H), 7.39 (t, J=7.9 Hz, 1H), 7.13 (d, J=7.5 Hz, 1H), 6.94-7.07 (m, 1H), 3.47 (br. s., 4H), 3.10- 3.29 (m, 4H), 2.79-3.07 (m, 2H), 1.47-1.82 (m, 4H), 0.66-1.17 ppm (m, 6H). MS: calc'd 448 (M+H)⁺. measured 448 (M+H)⁺.

Example 55

2-Amino-N4-isobutyl-N8-(m-tolyl)-N4-propyl-3H-1-benzazepine-4,8-dicarboxamide

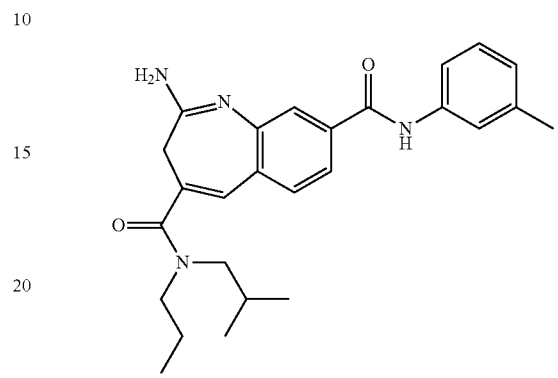

The title compound was prepared in analogy to Example 26 by using 2-methyl-N-propyl-propan-1-amine instead of 3-(propylamino)-propan-1-ol. Example 55 was obtained as a white solid (14.8 mg). 1H NMR (400 MHz, CD₃OD) δ ppm=7.86-7.83 (m, 2H), 7.63 (d, J=8 Hz, 1H), 7.53 (s, 1H), 7.50 (d, J=8 Hz, 1H), 7.26 (t, J=8 Hz, 1H), 7.06 (s, 1H), 7.01 (d, J=8 Hz, 1H), 3.48 (br, 4H), 3.31 (s, 2H), 2.37 (s, 3H), 1.69 (br, 3H), 0.99-0.91 (m, 9H). MS: calc'd 433 (M+H)⁺. measured 433 (M+H)⁺.

Example 56

2-Amino-N4-[3-(3-aminopropoxy)propyl]-N8-(m-tolyl)-N4-propyl-3H-1-benzazepine-4,8-dicarboxamide

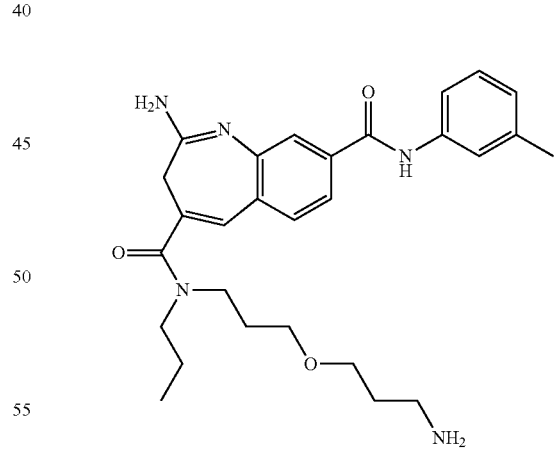

The title compound was prepared in analogy to Example 26 by using tert-butyl N-[3-[3-(propylamino)propoxy]propyl]carbamate (compound 56B) instead of 3-(propylamino)-propan-1-ol. Example 56 was obtained as a white solid (12.4 mg). 1H NMR (400 MHz, CD₃OD) δ ppm=7.80-7.75 (m, 2H), 7.58-7.56 (m, 1H), 7.53 (s, 1H), 7.50 (d, J=8 Hz, 1H), 7.25 (t, J=8 Hz, 1H), 7.03-6.99 (m, 2H), 3.60-3.56 (m, 4H), 3.48 (m, 4H), 3.31 (s, 2H), 3.30-3.08 (br, 2H), 2.37 (s, 3H), 1.95-1.92 (br, 3H), 1.73-1.67 (m, 3H), 0.97-0.90 (br, 3H). MS: calc'd 492 (M+H)⁺. measured 492 (M+H)⁺.

Preparation of Compound 56B

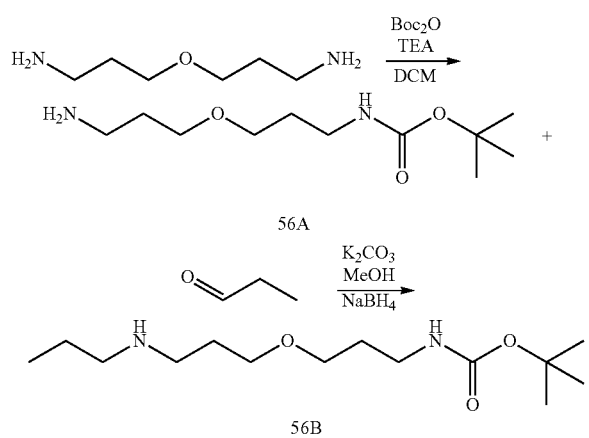

To a flask was added 3,3'-oxybis(propan-1-amine) (1 g, 7.56 mmol) and DCM (1 mL). A yellow solution was formed, then a solution of Boc-anhydride (825 mg, 878 μl, 3.78 mmol) in DCM (4 mL) was added drop-wise via a dropping funnel at r.t. over 50 mins. When it was completed, the mixture was stirred for 3 hours. The mixture was concentrated to give a yellow slurry, then it was re-dissolved in water (30 mL) and filtered through celite. The residue was washed with another 20 mL water. The filtrate was extracted with DCM (25 mL×6). The organic layer was washed with brine (30 mL×2), dried over Na$_2$SO$_4$ and concentrated to give about 550 mg tert-butyl (3-(3-aminopropoxy)propyl) carbamate (Compound 56A) as yellow oil. MS: calc'd 233 (M+H)$^+$. measured 233 (M+H)$^+$.

To a solution of tert-butyl (3-(3-aminopropoxy)propyl) carbamate (550 mg, 2.37 mmol) in methanol (9 mL) was added dropwisely propionaldehyde (137 mg, 172 μl, 2.37 mmol). A pale yellow solution was formed, then K$_2$CO$_3$ (327 mg, 2.37 mmol) was added. After the suspension was stirred overnight, the undissolved material was removed by filtration. The filtrate was cooled with ice bath, then NaBH$_4$ (134 mg, 3.55 mmol) was added portion-wise. After the mixture was warmed to r.t. and stirred for 3 hours, it was treated with 30 mL water. The mixture was extracted with DCM (25 mL×6). The organic layer was washed with brine (30 mL), dried over Na$_2$SO$_4$ and concentrated to give the crude product. Purification by combiflash (eluted with EA/PE=50%~100%) gave about 440 mg tert-butyl-N-[3-[3-(propylamino)propoxyl-propylicarbamate (Compound 56B) as yellow oil. MS: calc'd 275 (M+H)$^+$. measured 275 (M+H)$^+$.

Example 57

2-Amino-N8-[3-(5-aminopentyl)phenyl]-N4,N4-dipropyl-3H-1-benzazepine-4,8-dicarboxamide

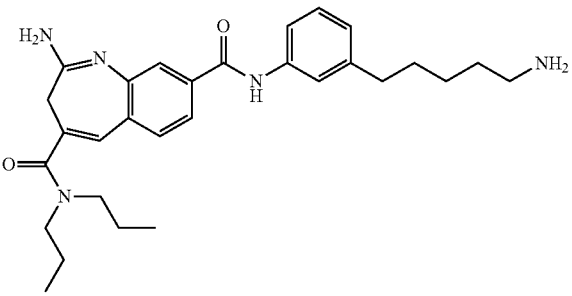 [SMILES: CCCN(CCC)C(=O)C1=Cc2ccc(C(=O)Nc3cccc(CCCCCN)c3)cc2N=C(N)C1]

A detailed synthetic route is provided in Scheme 6.

Scheme 6

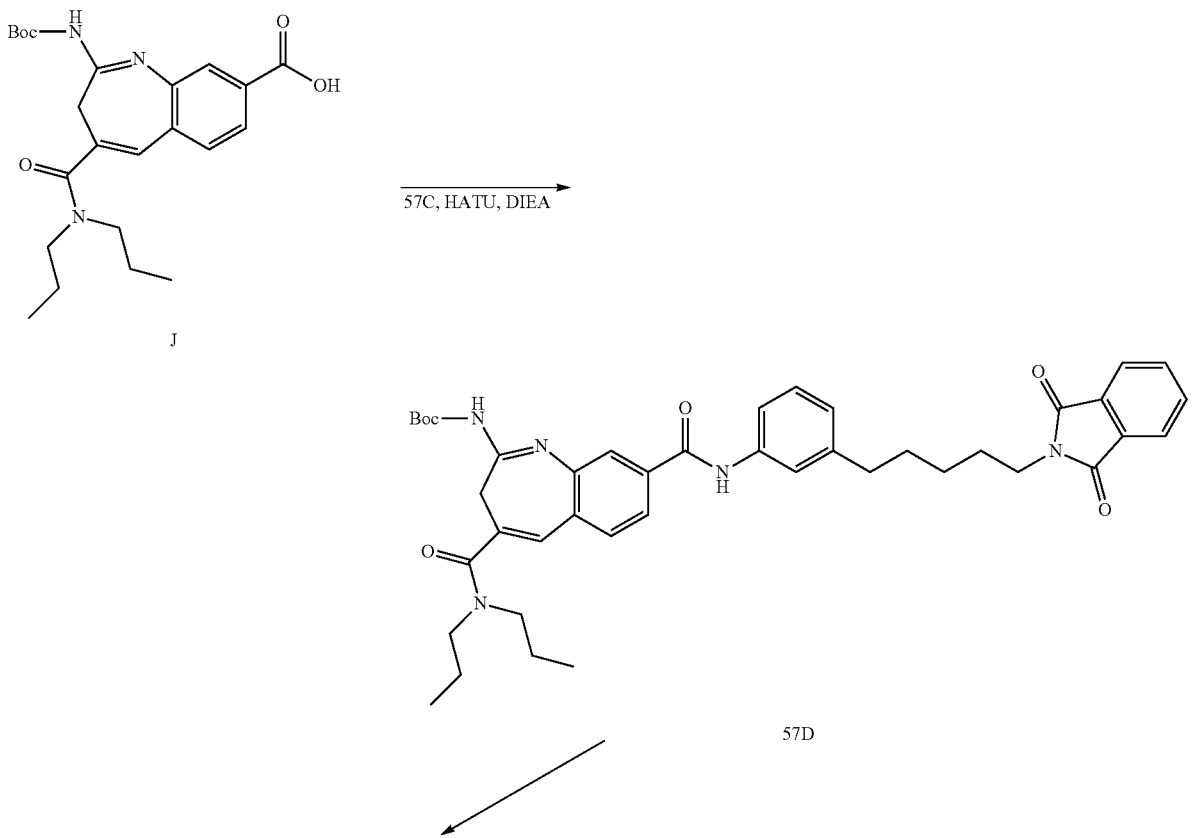

-continued
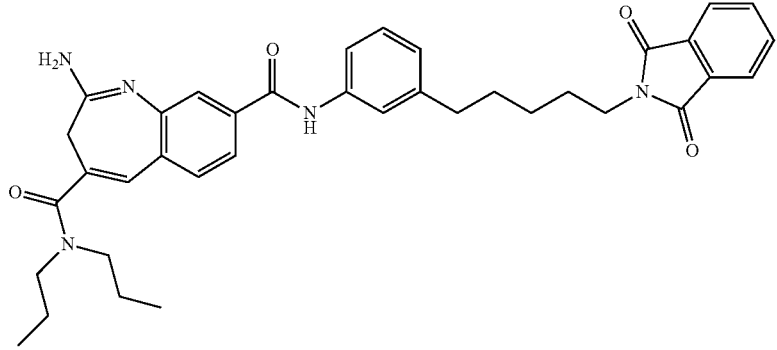
57E
↓ MeNH$_2$/EtOH
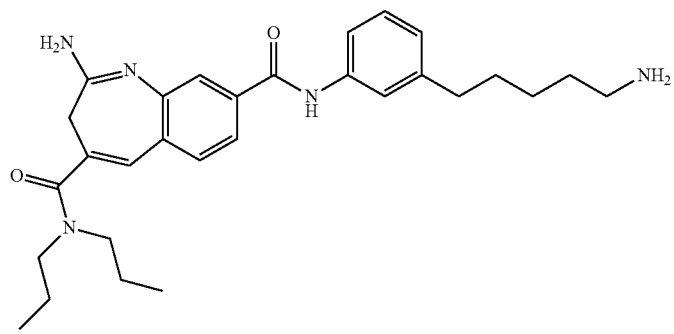
57
Preparation of Compound 57C
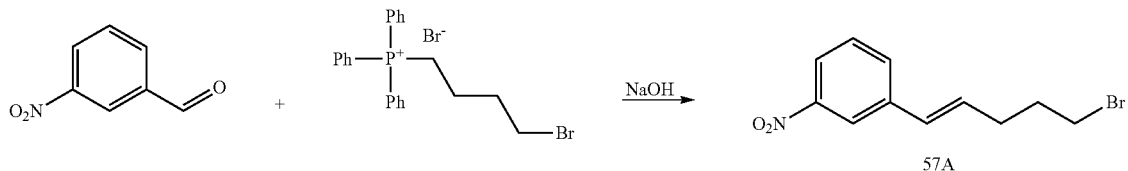
↓ DMA
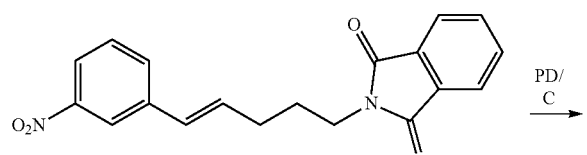
57B
→ Pd/C
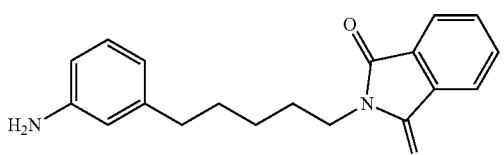
57C

Preparation of Compound 57A

To a mixture of 3-nitrobenzaldehyde (1.0 g, 6.60 mmol) and (4-bromobutyl)triphenyl-phosphonium bromide (3.5 g, 7.26 mmol) in a mixed solvent of THF (20 mL) and water (3 drops) was added NaOH (331 mg, 8.25 mmol). After the mixture was heated to 70° C. for 18 hours, it was filtered and the filtrate was concentrated to give the crude product. The crude product was purified by column chromatography (PE: EA=20:1) to give 1-(5-bromopent-1-en-1-yl)-3-nitrobenzene (compound 57A, 400 mg, 22.5%) as a white solid. MS: calc'd 270 $(M+H)^+$. measured 270 $(M+H)^+$.

Preparation of Compound 57B

A solution of 1-(5-bromopent-1-en-1-yl)-3-nitrobenzene (compound 57A, 300 mg, 1.11 mmol) and potassium 1,3-dioxoisoindolin-2-ide (210 mg, 1.11 mmol) in dimethylaniline (15 mL) was stirred under $N_2$ at 110° C. for 18 hours. The reaction mixture was diluted with water (30 mL), then extracted with EtOAc (25 mL×3). The combined organic phase was washed with brine (30 mL×3), dried over anhydrous $Na_2SO_4$ and concentrated to give 2-(5-(3-nitrophenyl)pent-4-en-1-yl)-isoindoline-1,3-dione (compound 57B, 300 mg) as a yellow oil. MS: calc'd 337 $(M+H)^+$. measured 337 $(M+H)^+$.

Preparation of Compound 57C

Pd/C (60 mg) was added into a solution of 2-(5-(3-nitrophenyl)pent-4-en-1-yl)-isoindoline-1,3-dione (compound 57B, 300 mg, 0.89 mmol) in MeOH (10 mL). After the mixture was degassed with hydrogen for 3 times with a hydrogen balloon, it was stirred under hydrogen (1103 hPA) at 16° C. for 18 hrs. The reaction mixture was filtered on celite, and the solid was washed with MeOH (5 mL×2). The combined filtrates were concentrated to give 2-(5-(3-aminophenyl)pentyl)isoindoline-1,3-dione (compound 57C, 0.2 g, 72.7%) as a yellow solid. MS: calc'd 309 $(M+H)^+$. measured 309 $(M+H)^+$.

Preparation of Compound 57D

To a solution of 2-((tert-butoxycarbonyl)amino)-4-(dipropylcarbamoyl)-3H-benzo[b]azepine-8-carboxylic acid (compound J, 200 mg, 0.46 mmol) in DMF (5 mL) at 0° C. was added DIPEA (148 mg, 1.15 mmol), HATU (209.7 mg, 0.55 mmol) and 2-(5-(3-aminophenyl)pentyl)isoindoline-1,3-dione (compound 57C, 158 mg, 0.51 mmol). After the mixture was stirred at 25° C. for 16 hours, it was diluted with brine (20 mL) and then extracted with EtOAc (25 mL×2). The combined organic phase was washed with saturated $NH_4Cl$ (20 mL), brine (30 mL×3), dried over anhydrous $Na_2SO_4$ and concentrated to give tert-butyl (5-(1,3-dioxoisoindolin-2-yl)pentyl)phenyl)carbamoyl)-4-(dipropylcarbamoyl)-3H-benzo[b]azepin-2-yl)carbamate (compound 57D, 200 mg, 59.6%) as a yellow solid. MS: calc'd 720 $(M+H)^+$. measured 720 $(M+H)^+$.

Preparation of Compound 57E

TFA (561 mg) was added drop-wise to a solution of tert-butyl (8-((3-(5-(1,3-dioxoisoindolin-2-yl)pentyl)phenyl)carbamoyl)-4-(dipropylcarbamoyl)-3H-benzo[b]azepin-2-yl)carbamate (compound 57D, 200 mg, 0.28 mmol) in DCM (5 mL) at 0° C. After the mixture was stirred for 3 hours at 20° C., it was concentrated to give the crude product. The crude product was added to aq.$NaHCO_3$ (20 mL), extracted with DCM (5 mL). The organic layer was washed with brine, dried over anhydrous $Na_2SO_4$ and concentrated to give 2-amino-N8-(3-(5-(1,3-dioxoisoindolin-2-yl)pentyl)phenyl)-N4,N4-dipropyl-3H-benzo[b]azepine-4,8-dicarboxamide (compound 57E, 150 mg, 87.2%) as a brown oil. MS: calc'd 620 $(M+H)^+$. measured 620 $(M+H)^+$.

Preparation of Example 57

A mixture of 2-amino-N8-(3-(5-(1,3-dioxoisoindolin-2-yl)pentyl)phenyl)-N4, N4-dipropyl-3H-benzo[b]azepine-4, 8-dicarboxamide (compound 57E, 50 mg, 0.08 mmol) in ethanolic methylamine (1.0 mL) was stirred for 2 hours at 20° C. The solvent was removed in vacuo at 16° C. The residue was acidified with TFA (0.2 mL in 1 mL EtOH), and then concentrated to an oil. The oil was purified by Pre-HPLC (TFA-system) to give 2-amino-N8-[3-(5-aminopentyl)phenyl]-N4,N4-dipropyl-3H-1-benzazepine-4,8-dicarboxamide example 57 (8.5 mg, 21.5%) as a white solid. 1H NMR (400 MHz, METHANOL-d4) δ ppm=7.99-7.93 (m, 2H), 7.71 (d, J=8.8 Hz, 1H), 7.66 (s, 1H), 7.49 (d, J=8.0 Hz, 1H), 7.32 (t, J=7.8 Hz, 1H), 7.13 (s, 1H), 7.06 (d, J=7.5 Hz, 1H), 3.49 (br. s., 4H), 3.38 (d, J=8.8 Hz, 2H), 2.94 (t, J=7.5 Hz, 2H), 2.71 (t, J=7.5 Hz, 2H), 1.72 (qd, J=7.1, 14.8 Hz, 8H), 1.55-1.42 (m, 2H), 0.98 (br. s., 6H). MS: calc'd 490 $(M+H)^+$. measured 490 $(M+H)^+$.

Example 58

2-Amino-N8-[4-(5-aminopentyl)phenyl]-N4,N4-dipropyl-3H-1-benzazepine-4,8-dicarboxamide

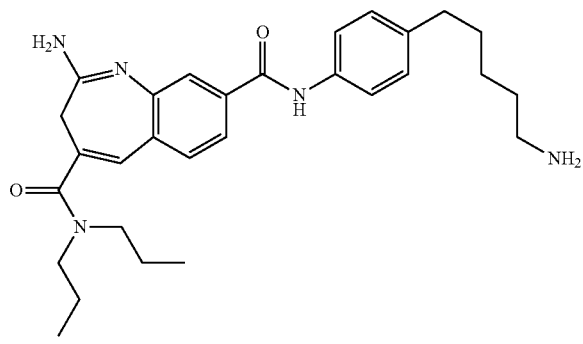 [SMILES: CCCN(CCC)C(=O)C1=Cc2ccc(C(=O)Nc3ccc(CCCCCN)cc3)cc2N=C(N)C1]

The title compound was prepared in analogy to Example 57 by using 4-nitrobenzaldehyde instead of 3-nitrobenzaldehyde. Example 58 was obtained as a white solid (13.5 mg). 1H NMR (400 MHz, $CD_3OD$) δ ppm=7.94 (d, J=1.63 Hz, 2H), 7.71-7.65 (m, 1H), 7.62 (d, J=8.41 Hz, 2H), 7.26-7.19 (m, 2H), 7.12-7.08 (m, 1H), 3.53-3.40 (m, 4H), 3.38-3.35 (m, 1H), 3.35-3.33 (m, 1H), 2.95-2.88 (m, 2H), 2.70-2.62 (m, 2H), 1.75-1.65 (m, 8H), 1.50-1.39 (m, 2H), 1.07-0.81 (m, 6H) MS: calc'd 490 $(M+H)^+$. measured 490 $(M+H)^+$.

Example 59

2-Amino-N8-[3-(3-aminopropyl)phenyl]-N4,N4-dipropyl-3H-1-benzazepine-4,8-dicarboxamide

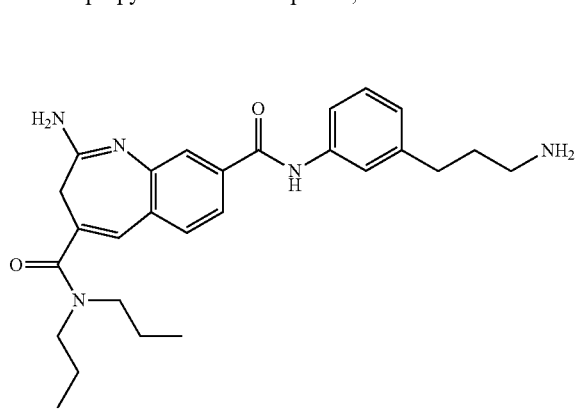

The title compound was prepared in analogy to Example 1 by using tert-butyl (3-(3-aminophenyl)propyl)carbamate instead of pyridin-3-amine. Example 59 was obtained as a yellow solid (49 mg). 1H-NMR (400 MHz, CD$_3$OD) δ ppm=7.82-7.97 (m, 2H), 7.60-7.76 (m, 2H), 7.51 (d, J=8.3 Hz, 1H), 7.35 (t, J=7.8 Hz, 1H), 6.98-7.14 (m, 2H), 3.48 (br. s., 4H), 2.90-3.06 (m, 2H), 2.83 (s, 2H), 2.64-2.81 (m, 2H), 1.92-2.12 (m, 2H), 1.72 (sxt, J=7.5 Hz, 4H), 0.96 ppm (d, J=18.6 Hz, 6H). MS: calc'd 462 (M+H)$^+$. measured 462 (M+H)$^+$.

Example 60

2-Amino-N4-[[4-(aminomethyl)phenyl]methyl]-N8-(m-tolyl)-N4-propyl-3H-1-benzazepine-4,8-dicarboxamide

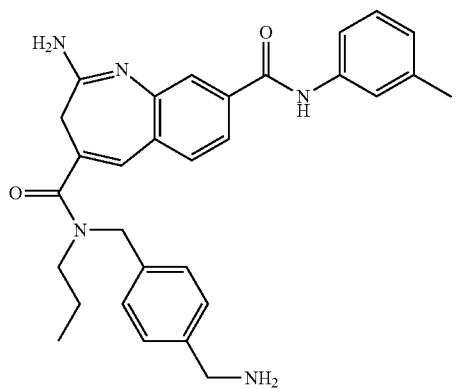 [SMILES: CCCN(Cc1ccc(CN)cc1)C(=O)C1=Cc2ccc(C(=O)Nc3cccc(C)c3)cc2N=C(N)C1]

The title compound was prepared in analogy to Example 26 by using tert-butyl N-[[4-(propylaminomethyl)phenyl]methyl]carbamate (compound 60B) instead of 3-(propylamino)-propan-1-ol. Example 60 was obtained as a white solid (9.9 mg). 1H NMR (400 MHz, CD$_3$OD) δ ppm=7.82-7.78 (m, 2H), 7.53-7.40 (m, 7H), 7.25 (t, J=8 Hz, 1H), 7.09 (s, 1H), 7.00 (d, J=8 Hz, 1H), 4.80 (s, 2H), 4.13 (s, 2H), 3.49-3.45 (m, 2H), 3.31 (s, 2H), 2.37 (s, 3H), 1.71-1.66 (m, 2H), 0.90 (br, 3H). MS: calc'd 496 (M+H)$^+$. measured 496 (M+H)$^+$.

Preparation of Compound 60B

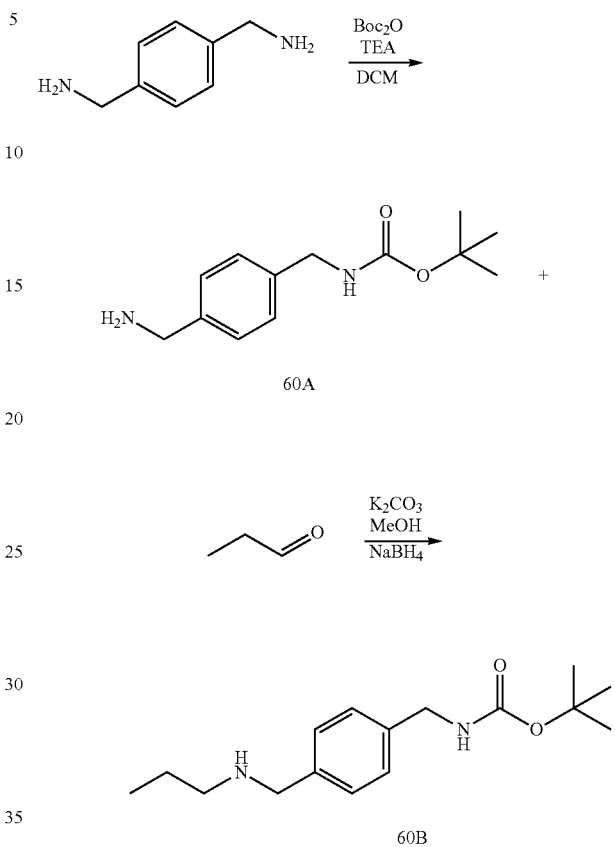

To a 50 mL flask was added 1,4-phenylenedimethanamine (1 g, 7.34 mmol), TEA (1.11 g, 1.54 mL, 11 mmol) and DCM (10 mL). Then a solution of Boc-anhydride (801 mg, 852 μL, 3.67 mmol) in DCM (10 mL) was added drop-wise at 0° C. The mixture was warmed to r.t. and stirred for 2 hours. The mixture was then diluted with 20 mL DCM and 30 mL water. The suspension was separated and the water layer was extracted with 20 mL DCM. The organic layers were combined and washed with sat. NH$_4$Cl, dried over Na$_2$SO$_4$ and concentrated to give a 0.5 g tert-butyl 4-(aminomethyl)benzylcarbamate (compound 60A) as a white solid. MS: calc'd 237 (M+H)$^+$. measured 237 (M+H)$^+$.

To a flask was added tert-butyl-4-(aminomethyl)benzylcarbamate (0.5 g, 2.12 mmol), propionaldehyde (184 mg, 230 μl, 3.17 mmol) and methanol (15 mL) followed by K$_2$CO$_3$ (292 mg, 2.12 mmol) at r.t. After the mixture was stirred at r.t. overnight, the precipitate was filtered through celite. The filtrate was cooled with ice bath and NaBH$_4$ (120 mg, 3.17 mmol) was added portion-wise. The mixture was warmed to r.t. and stirred for about 2 hours. The mixture was concentrated to give a sticky solid which was purified via combiflash (eluted with EA/PE=0~100%) to give about 123 mg of tert-butyl N-[[4-(propylaminomethyl)phenyl]methyl]-carbamate (Compound 60B) as sticky oil. MS: calc'd 279 (M+H)$^+$. measured 279 (M+H)$^+$.

Example 61

2-Amino-N8-[4-(3-aminopropyl)phenyl]-N4,N4-dipropyl-3H-1-benzazepine-4,8-dicarboxamide

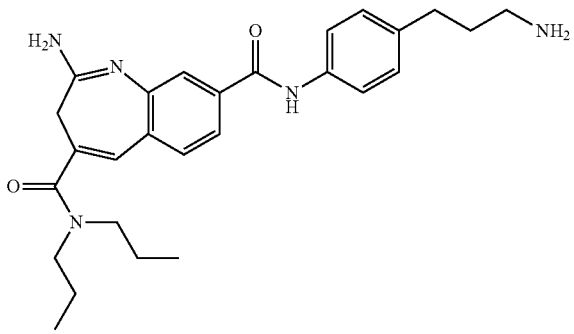 [SMILES: CCCN(CCC)C(=O)C1=Cc2ccc(C(=O)Nc3ccc(CCCN)cc3)cc2N=C(N)C1]

The title compound was prepared in analogy to Example 1 by using tert-butyl (3-(4-aminophenyl)propyl)carbamate instead of pyridin-3-amine. Example 61 was obtained as a yellow solid (22 mg). 1H NMR (400 MHz, CD$_3$OD) δ ppm=7.87-8.01 (m, 2H), 7.57-7.73 (m, 3H), 7.29 (d, J=8.5 Hz, 2H), 7.05-7.13 (m, 1H), 3.48 (br. s., 4H), 3.20 (m, 2H), 2.91-3.02 (m, 2H), 2.65-2.82 (m, 2H), 2.00 (dt, J=15.5, 7.7 Hz, 2H), 1.72 (dq, J=15.1, 7.5 Hz, 4H), 0.97 ppm (br. s., 6H). MS: calc'd 462 (M+H)$^+$. measured 462 (M+H)$^+$.

Example 62

2-Amino-N8-[4-(3-aminopropyl)phenyl]-N4,N4-dipropyl-3H-1-benzazepine-4,8-dicarboxamide

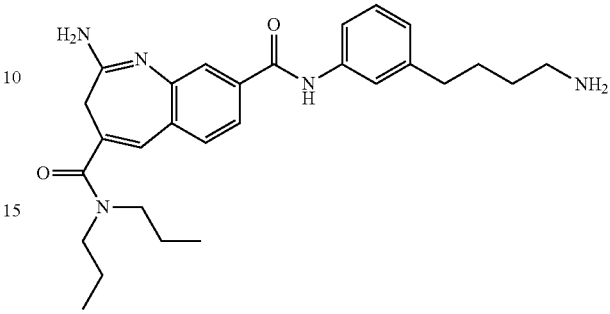

The title compound was prepared in analogy to Example 1 by using tert-butyl (3-(4-aminophenyl)butyl)carbamate (compound 62F) instead of pyridin-3-amine. Example 62 was obtained as a yellow solid (21 mg). 1H NMR (400 MHz, CD$_3$OD) δ ppm=7.98-7.93 (m, 2H), 7.72-7.63 (m, 2H), 7.55-7.50 (m, 1H), 7.35-7.29 (m, 1H), 7.12-7.09 (m, 1H), 7.09-7.04 (m, 1H), 3.55-3.41 (m, 4H), 3.38 (s, 2H), 3.00-2.92 (t, J=6.8 Hz, 2H), 2.77-2.69 (t, J=6.8 Hz, 2H), 1.82-1.63 (m, 8H), 1.07-0.84 (m, 6H). MS: calc'd 476 (M+H)$^+$. measured 476 (M+H)$^+$.

Preparation of Compound 62F

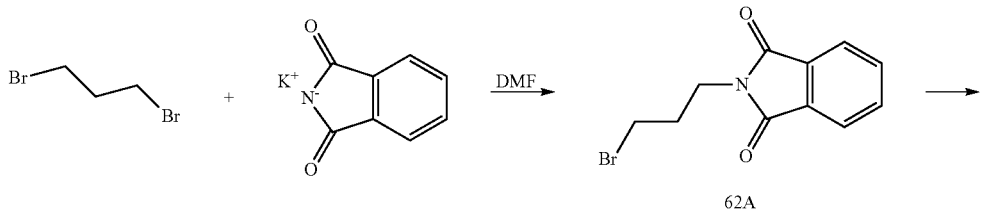

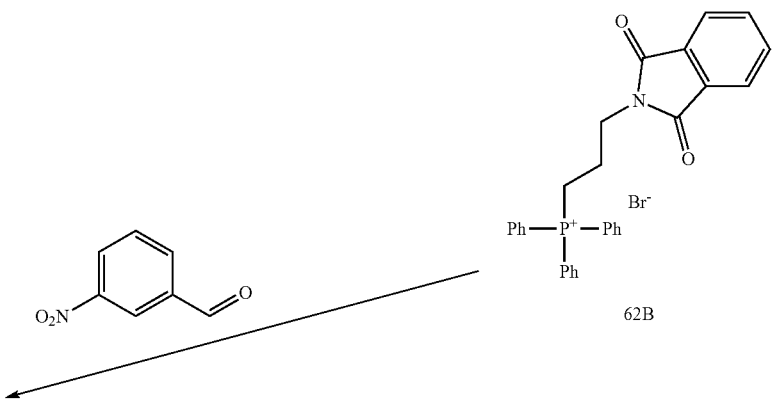

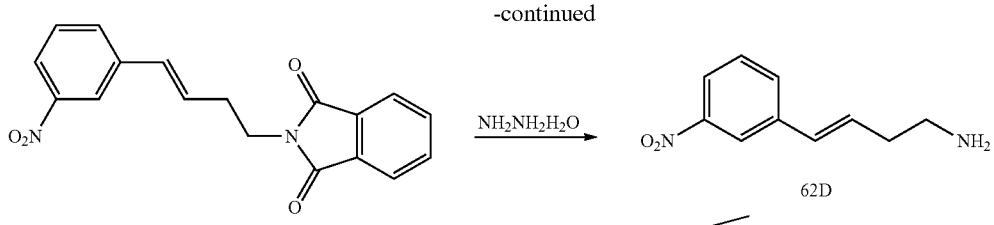

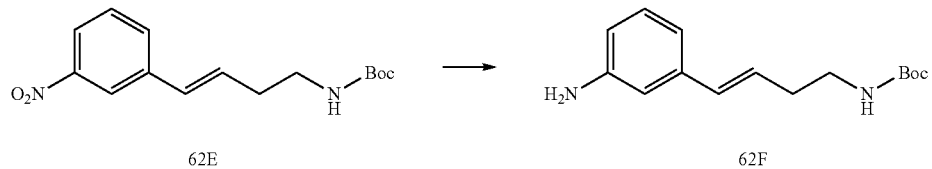

Preparation of Compound 62A

A solution of 1,3-dibromopropane (16.4 g, 81.0 mmol) and potassium phthalimide (5.0 g, 27.0 mmol) in DMF (100 mL) was stirred under $N_2$ at 18° C. for 20 hours. The reaction mixture was concentrated, and the residue was diluted with EtOAc (30 mL). The organic phase was washed with water (20 mL), brine (20 mL×2), dried by anhydrous $Na_2SO_4$ and concentrated. The residue was triturated with PE (30 mL), filtered to give 2-(3-bromopropyl)isoindoline-1,3-dione (compound 62A, 4.3 g, 59.7%) as a white solid. MS: calc'd 268 $(M+H)^+$. measured 268 $(M+H)^+$.

Preparation of Compound 62B

A solution of 2-(3-bromopropyl)isoindoline-1,3-dione (compound 62A, 1.0 g, 4.0 mmol), triphenylphosphine (1.0 g, 4.0 mmol) in toluene (50 mL) was stirred under $N_2$ at 110° C. for 18 hours. The product was precipitated and collected by filtration to give [3-(1,3-dioxo-1,3-dihydro-isoindol-2-yl)-propyl]-triphenyl-phosphonium bromide (compound 62B, 280 mg, 13.2%) as a white solid.

Preparation of Compound 62C

To a stirred solution of 3-nitrobenzaldehyde (80 mg, 0.53 mmol), [3-(1,3-dioxo-1,3-dihydro-isoindol-2-yl)-propyl]-triphenyl-phosphonium bromide (compound 62B, 280 mg, 0.53 mmol) in THF (5 mL) was added potassium tert-butoxide (65 mg, 0.58 mmol) at 0° C. Then the reaction mixture was stirred under $N_2$ at 70° C. for 19 hours. The reaction mixture was filtered and the filtrate was concentrated to give a residue which was purified by silica gel chromatography (PE:EA=20:1-10:1) to give (E)-2-(4-(3-nitrophenyl)but-3-en-1-yl)isoindoline-1,3-dione (compound 62C, 80 mg, 46.8%) as a white solid. MS: calc'd 323 $(M+H)^+$. measured 323 $(M+H)^+$.

Preparation of Compound 62D

To a stirred solution of (E)-2-(4-(3-nitrophenyl)but-3-en-1-yl)isoindoline-1,3-dione (compound 62C, 80 mg, 0.25 mmol) in EtOH (4 mL) was added $NH_2NH_2 \times H_2O$ (25 mg, 0.50 mmol) drop-wise at 0° C. Then the mixture was stirred at 10° C. for 48 hrs. The reaction mixture was concentrated and the residue was diluted with DCM (30 mL) and stirred for 30 min. The undissolved material was filtered and the filtrate was concentrated to give a residue which was purified by Pre-TLC (DCM/MeOH=20:1 twice) to give (E)-4-(3-nitrophenyl)but-3-en-1-amine (compound 62D, 23 mg, 47.9%) as a colorless oil. MS: calc'd 193 $(M+H)^+$. measured 193 $(M+H)^+$.

Preparation of Compound 62E

A solution of (E)-4-(3-nitrophenyl)but-3-en-1-amine (compound 62D, 23 mg, 0.12 mmol), $Et_3N$ (24 mg, 0.24 mmol) and $Boc_2O$ (39 mg, 0.18 mmol) in DCM (1 mL) was stirred under $N_2$ at 18° C. for 16 hrs. TLC (PE: EA=1:1) showed the (E)-4-(3-nitrophenyl)but-3-en-1-amine was consumed completely. The reaction mixture was concentrated to give crude product. The crude product was purified by Pre-TLC (PE:EA=2:1) to give (E)-tert-butyl (4-(3-nitrophenyl)but-3-en-1-yl)carbamate (compound 62E, 28 mg, 80.0%) as colorless oil. MS: calc'd 315 $(M+Na)^+$. measured 315 $(M+Na)^+$.

Preparation of Compound 62F

Pd/C (3 mg) was added into a solution of (E)-tert-butyl (4-(3-nitrophenyl)but-3-en-1-yl)carbamate (compound 62E, 28 mg, 0.09 mmol) in MeOH (1.5 mL). The mixture was degassed with $H_2$ for 3 times with a hydrogen balloon. Then the mixture was stirred under $H_2$ (1103 hPa) at 18° C. for 4 hrs. The reaction mixture was filtered and the filtrate was concentrated to give crude tert-butyl (4-(3-aminophenyl)butyl)carbamate (compound 62F, 30 mg) as a colorless oil. MS: calc'd 265 $(M+H)^+$. measured 265 $(M+H)^+$.

Example 63

2-Amino-N8-[3-(2-aminoethyl)-4-fluoro-phenyl]-N4,N4-dipropyl-3H-1-benzazepine-4,8-dicarboxamide

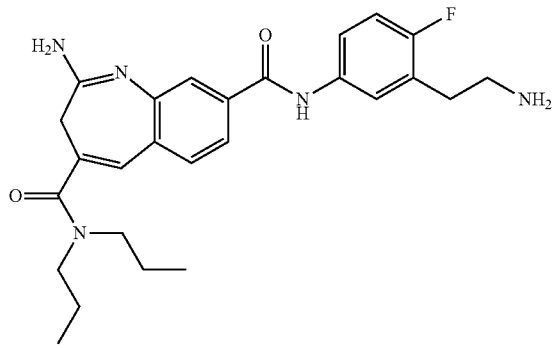 [SMILES: CCCN(CCC)C(=O)C1=Cc2ccc(C(=O)Nc3ccc(F)c(CCN)c3)cc2N=C(N)C1]

The title compound was prepared in analogy to Example 1 by using tert-butyl 5-amino-2-fluorophenethylcarbamate (compound 63E) instead of pyridin-3-amine. Example 63 was obtained as a yellow solid (21 mg). 1H NMR (400 MHz, CD$_3$OD) δ ppm=7.93-8.00 (m, 2H), 7.82 (br. s., 1H), 7.72 (d, J=8.66 Hz, 1H), 7.57 (br. s., 1H), 7.20 (t, J=9.35 Hz, 1H), 7.13 (s, 1H), 3.49 (d, J=6.65 Hz, 4H), 3.39 (s, 2H), 3.20-3.27 (m, 2H), 3.04-3.11 (m, 2H), 1.66-1.78 (m, 4H), 0.97 (d, J=5.52 Hz, 6H). MS: calc'd 466 (M+H)$^+$. measured 466 (M+H)$^+$.

Preparation of Compound 63E

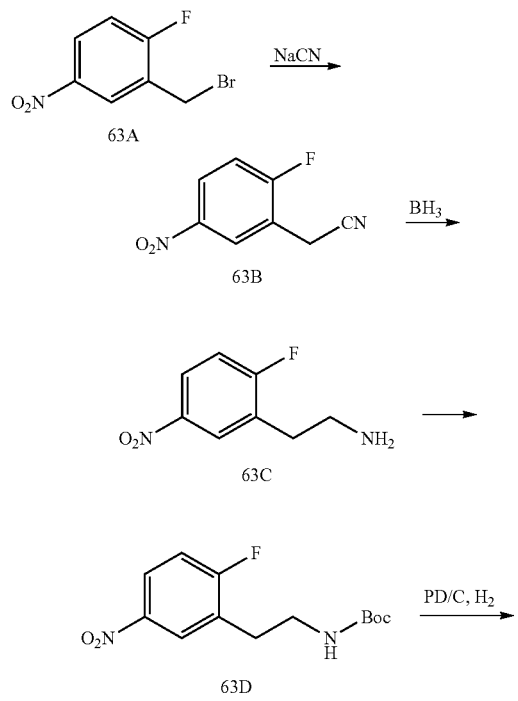

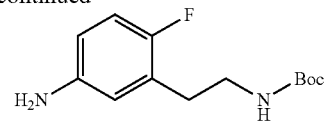

Preparation of Compound 63B

To a solution of NaCN (0.63 g, 12.9 mmol) in H$_2$O (6.0 mL) was added drop-wise 2-(bromomethyl)-1-fluoro-4-nitrobenzene (compound 63A, 2.0 g, 8.6 mmol) in EtOH (30 mL) at 20° C. After the reaction mixture was stirred for 4 hrs, it was quenched with 2 N NaOH (10 mL).

The mixture was diluted with H$_2$O (100 mL) and extracted with EA (50 mL×3). The combined organic layers were washed with brine (30 mL×2), dried over Na$_2$SO$_4$, filtered and concentrated to give 2-(2-fluoro-5-nitrophenyl)acetonitrile (compound 63B, 1.6 g) as yellow oil without further purification. MS: calc'd 180 (M+H)$^+$. measured 180 (M+H)$^+$.

Preparation of Compound 63C

To a solution of 2-(2-fluoro-5-nitrophenyl)acetonitrile (compound 63B, 0.7 g, 3.9 mmol) in THF (20 mL) was added BH$_3$/THF (1 M, 16 mL, 15.5 mmol) at 25° C. After the reaction mixture was stirred for 2 hrs at 70° C., it was quenched with MeOH (10 mL). The mixture was diluted with H$_2$O (200 mL) and extracted with EA (50 mL×3). The combined organic layers were washed with brine (30 mL×2), dried over anhydrous Na$_2$SO$_4$) and concentrated to give 2-(2-fluoro-5-nitrophenyl)ethanamine (compound 63C, 700 mg) as yellow oil without further purification. MS: calc'd 184 (M+H)$^+$. measured 184 (M+H)$^+$.

Preparation of Compound 63D

To a solution of 2-(2-fluoro-5-nitrophenyl)ethanamine (compound 63C, 700 mg, 3.9 mmol) and DIPEA (1.5 g, 11.7 mmol) in DCM (30 mL) was added Boc$_2$O (932 mg, 4.3 mmol) at 0° C.

Then the mixture was stirred for 1 h at 25° C. The reaction solution was quenched with saturated NH$_4$Cl (20 mL), diluted with H$_2$O (100 mL) and extracted with DCM (30 mL×3). The combined organic layers were washed with brine (20 mL×2), dried over anhydrous Na$_2$SO$_4$ and concentrated. The crude product was purified by silica gel column chromatography (PE: EA=4:1) to give tert-butyl 2-fluoro-5-nitrophenethylcarbamate (compound 63D, 600 mg, 54.5%) as yellow oil. MS: calc'd 284 (M+H)$^+$. measured 284 (M+H)$^+$.

Preparation of Compound 63E

To a solution of tert-butyl 2-fluoro-5-nitrophenethylcarbamate (compound 63D, 600 mg, 2.11 mmol) in MeOH (15 mL) was added Pd/C (100 mg). The reaction mixture was stirred for 18 hours at 25° C. under hydrogen atmosphere. The solution was filtered and the filtrate was concentrated to give tert-butyl 5-amino-2-fluorophenethylcarbamate (compound 63E, 500 mg) as green oil without further purification. MS: calc'd 254 (M+H)$^+$. measured 254 (M+H)$^+$.

Example 64

2-Amino-N8-[3-(2-aminoethyl)-5-chloro-phenyl]-N4,N4-dipropyl-3H-1-benzazepine-4,8-dicarboxamide

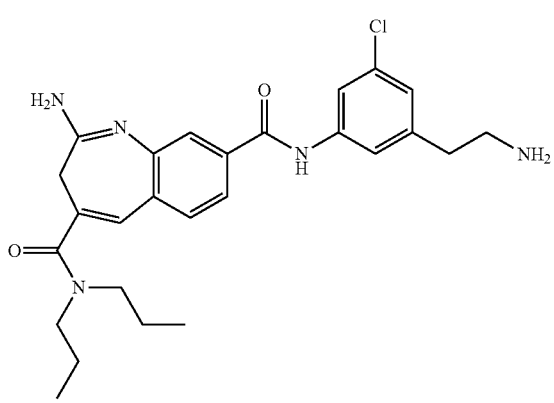 [SMILES: CCCN(CCC)C(=O)C1=Cc2ccc(C(=O)Nc3cc(Cl)cc(CCN)c3)cc2N=C(N)C1]

The title compound was prepared in analogy to Example 1 by using tert-butyl 3-amino-5-chlorophenethylcarbamate (compound 64A) instead of pyridin-3-amine. Example 64 was obtained as a yellow solid (20 mg). 1H NMR (400 MHz, METHANOL-d4) δ ppm=7.96-7.93 (m, 2H), 7.73-7.68 (m, 3H), 7.16 (s, 1H), 7.10 (s, 1H), 3.46 (br. s., 4H), 3.37 (s, 2H), 3.22-3.20 (m, 2H), 3.00-2.96 (m, 2H), 1.73-1.67 (m, 4H), 0.97 (br. s., 6H). MS: calc'd 482 (M+H)$^+$. measured 482 (M+H)$^+$, 482 (M+H)$^+$.

Preparation of Compound 64A

The title compound was prepared in analogy to Example 63E by using 1-(bromomethyl)-3-chloro-5-nitrobenzene instead of 2-(bromomethyl)-1-fluoro-4-nitrobenzene.

Example 65

2-Amino-N4-butyl-N4-(2-hydroxyethyl)-N8-(m-tolyl)-3H-1-benzazepine-4,8-dicarboxamide

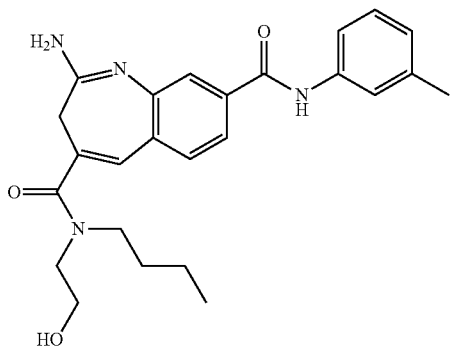 [SMILES: CCCCN(CCO)C(=O)C1=Cc2ccc(C(=O)Nc3cccc(C)c3)cc2N=C(N)C1]

The title compound was prepared in analogy to Example 26 by using 2-(butylamino)-ethanol (compound 65A) instead of 3-(propylamino)-propan-1-ol. Example 65 was obtained as a white solid (48 mg). 1H NMR (400 MHz, CD$_3$OD) δ ppm=7.94-7.92 (m, 2H), 7.69-7.67 (d, J=8.0 Hz, 1H), 7.53-7.48 (m, 2H), 7.28-7.24 (m, 1H), 7.17 (s, 1H), 7.02-7.00 (d, J=7.2, 1H), 3.70-3.53 (br, 6H), 3.34 (s, 2H), 2.37 (s, 3H), 1.71-1.63 (m, 2H), 1.40 (br, 2H), 0.98 (br, 3H). MS: calc'd 435.2 (M+H)$^+$. measured 435.2 (M+H)$^+$.

Preparation of Compound 65A

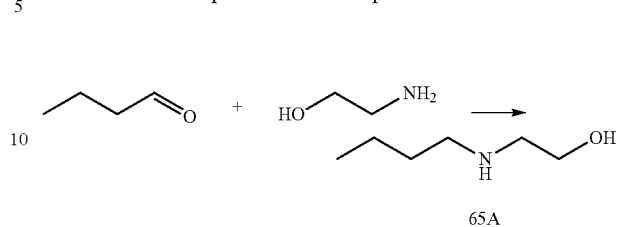

To a solution of butyraldehyde (1.0 g, 13.8 mmol) and 2-aminoethanol (847 mg, 13.8 mmol) in MeOH (20.0 mL) was added MgSO$_4$ (6.65 g, 55.5 mmol). The mixture was stirred at 20° C. for 12 hrs. The reaction mixture was filtered. To the filtrate was added NaBH$_4$ (0.58 g, 15.3 mmol) under ice-bath. The solution was stirred at 20° C. for 1 h. TLC (DCM/MeOH=10/1) showed a new point was formed. The reaction solution was concentrated in vacuo. The residue was dissolved in water (50 mL) and extracted with DCM (100 mL×3). The combined organic layers were dried over Na$_2$SO$_4$ and concentrated in vacuo to give crude 2-(butylamino)ethanol (compound 65A, 1.3 g, 80.2%) as colorless oil which was used for the next step directly.

Example 66

2-Amino-N8-[5-(2-aminoethoxy)-3-pyridyl]-N4,N4-dipropyl-3H-1-benzazepine-4,8-dicarboxamide

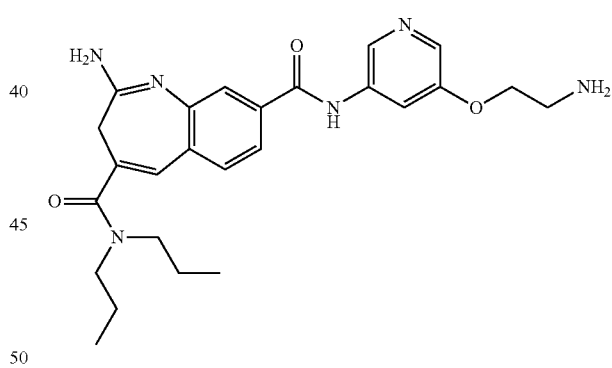

The title compound was prepared in analogy to Example 1 by using tert-butyl N-[2-[(5-amino-3-pyridyl)oxy]ethyl]carbamate (compound 66C) instead of pyridin-3-amine. Example 66 was obtained as a white solid (9.9 mg). 1H NMR (400 MHz, CD$_3$OD) δ ppm=8.57 (s, 1H), 8.20-8.17 (m, 2H), 8.00-7.97 (m, 2H), 7.72 (d, J=8 Hz, 1H), 7.12 (s, 1H), 4.37 (t, J=4 Hz, 2H), 3.45-3.43 (m, 6H), 3.38 (s, 2H), 1.75-1.66 (m, 4H), 0.97-0.93 (br, 6H). MS: calc'd 465 (M+H)$^+$. measured 465 (M+H)$^+$.

Preparation of Compound 66C

The title compound was prepared in analogy to compound 45C by using 2-aminoethanol instead of 2-(2-aminoethoxy)ethanol and 5-nitropyridin-3-ol instead of 3-nitrophenol. MS: calc'd 254 (M+H)$^+$. measured 254 (M+H)$^+$.

Example 67

Benzyl N-[[5-[[2-amino-4-(dipropylcarbamoyl)-3H-1-benzazepine-8-carbonyl]amino]-3-pyridyl]methyl]carbamate

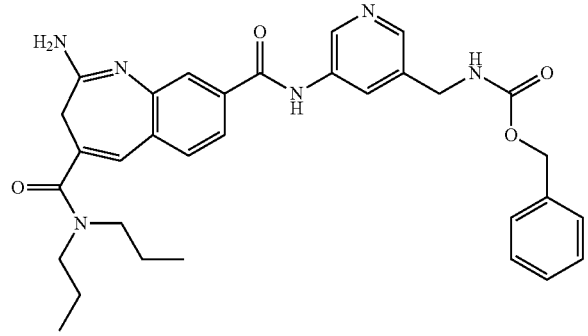 [SMILES: CCCN(CCC)C(=O)C1=Cc2ccc(C(=O)Nc3cncc(CNC(=O)OCc4ccccc4)c3)cc2N=C(N)C1]

The title compound was prepared in analogy to Example 1 by using benzyl N-[(5-amino-3-pyridyl)methyl]carbamate instead of pyridin-3-amine. Example 67 was obtained as a white solid (17 mg). 1H NMR (400 MHz, CD$_3$OD) δ ppm=9.12 (s, 1H) 8.44 (d, J=10.54 Hz, 2H) 7.98-8.05 (m, 2H) 7.75 (d, J=8.03 Hz, 1H) 7.22-7.42 (m, 5H) 7.14 (s, 1H) 5.14 (s, 2H) 4.47 (s, 2H) 3.50 (br. s., 4H) 3.36-3.43 (m, 2H) 1.67-1.79 (m, 4H) 0.98 (d, J=19.07 Hz, 6H). MS: calc'd 569.3 (M+H)$^+$. measured 569.3 (M+H)$^+$.

Example 68

2-Amino-N8-[5-[(E)-3-aminoprop-1-enyl]-3-pyridyl]-N4,N4-dipropyl-3H-1-benzazepine-4,8-dicarboxamide

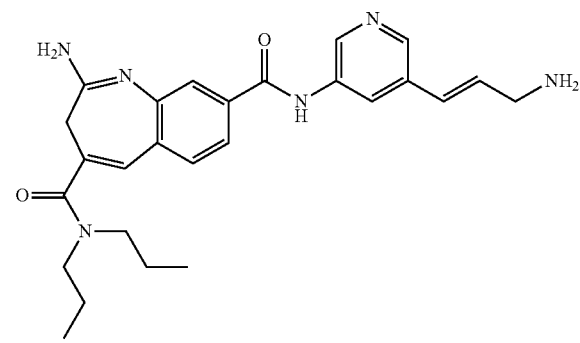 [SMILES: CCCN(CCC)C(=O)C1=Cc2ccc(C(=O)Nc3cncc(/C=C/CN)c3)cc2N=C(N)C1]

The title compound was prepared in analogy to Example 1 by using tert-butyl N-RE)-3-(5-amino-3-pyridypallylicarbamate (compound 68C) instead of pyridin-3-amine. Example 68 was obtained as a white solid (23 mg). 1H NMR (400 MHz, CD$_3$OD) δ ppm=8.73 (s, 1H), 8.56 (s, 1H), 8.39 (s, 1H), 7.82 (s, 1H), 7.75-7.74 (m, 1H), 7.57 (d, J=8 Hz, 1H), 6.99 (s, 1H), 6.89 (d, J=16 Hz, 1H), 6.49-6.45 (m, 1H), 3.78 (d, J=4 Hz, 2H), 3.46-3.43 (m, 4H), 3.31 (s, 2H), 1.72-1.67 (m, 4H), 0.98-0.89 (br, 6H). MS: calc'd 461 (M+H)$^+$. measured 461 (M+H)$^+$.

Preparation of Compound 68C

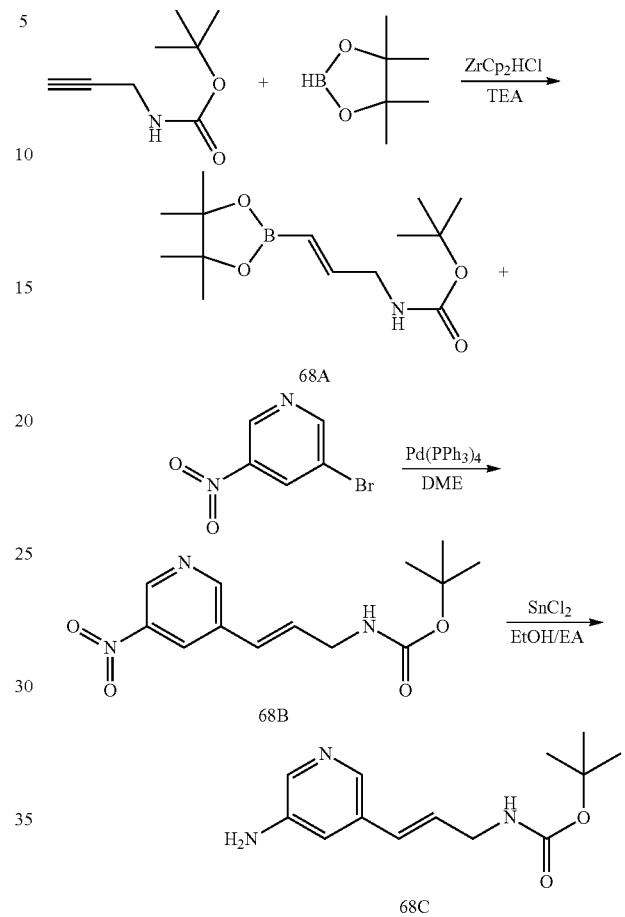

Preparation of Compound 68A

To a sealed tube was added tert-butyl prop-2-yn-1-ylcarbamate (1 g, 6.44 mmol), bis(cyclopentadienyl)zirconium chloride hydride (166 mg, 644 μmol), TEA (65.2 mg, 89.8 μl, 644 μmol) and 4,4,5,5-tetramethyl-1,3,2-dioxaborolane (1.24 g, 1.4 ml, 9.67 mmol). The tube was sealed and heated to 65° C. (oil bath) for 18 hours. The mixture was diluted with 25 mL EA and quenched with sat. NH$_4$Cl. Then another 25 mL EA was added and the mixture was washed sequentially with sat. NH$_4$Cl, sat. NaHCO$_3$ and brine. The organic layer was dried over Na$_2$SO$_4$ and concentrated to give 2.1 g pale yellow sticky oil. After purification via combiflash (eluted with EA/PE=0~40%), about 1.1 g (E)-tert-butyl (3-(4,4,5,5-tetramethyl-1,3,2-dioxaborolan-2-yl)allyl)carbamate (Compound 68A) was obtained as pale yellow oil. MS: calc'd 284 (M+H)$^+$. measured 284 (M+H)$^+$.

Preparation of Compound 68B

To a 25 mL flask was added (E)-tert-butyl (3-(4,4,5,5-tetramethyl-1,3,2-dioxaborolan-2-yl)allyl)carbamate (200 mg, 706 μmol), 3-bromo-5-nitropyridine (143 mg, 706 μmol), K$_2$CO$_3$ (293 mg, 2.12 mmol), dimethyl ether (4 mL), water (0.5 mL) and Pd(Ph3P)4 (81.6 mg, 70.6 μmol). Then the mixture was degassed for five times and was heated to 85° C. (oil bath) for 23 hours. The mixture was diluted with EA and water, filtered through celite. The organic layer was separated and the aqueous layer was extracted with EA. The combined organic layers were washed with brine, dried over Na₂SO₄ and concentrated to give a brown oil. After purification via combifalsh (eluted with EA/PE=0~35%), about 160 mg (E)-tert-butyl (3-(5-nitropyridin-3-yl)allyl)carbamate (Compound 68B) was obtained as yellow sticky solid. MS: calc'd 280 (M+H)⁺. measured 280 (M+H)⁺.

Preparation of Compound 68C

To a flask was added (E)-tert-butyl (3-(5-nitropyridin-3-yl)allyl)carbamate (160 mg, 573 μmol), EtOAc (3 mL) and ethanol (2 mL). A pale yellow solution was formed and then heated to about 60° C. (oil bath). The stannous chloride (652 mg, 165 μl, 3.44 mmol) was added in small portions. The reaction was stirred at 60° C. for 3 hours. The mixture was cooled and diluted with 20 mL EA. A 25 wt. % aqueous solution of KOH was added (pH>7). The precipitate was filtered through celite and the filtrate was extracted with EA (15 mL×4). The combined organic layers were washed with brine, dried over Na₂SO₄ and concentrated to give about 90 mg tert-butyl N-[(E)-3-(5-amino-3-pyridyl)allyl]carbamate (Compound 68C) as yellow solid. MS: calc'd 250 (M+H)⁺. measured 250 (M+H)⁺.

Example 69

2-Amino-N8-[5-(2-phenylethyl)-3-pyridyl]-N4,N4-dipropyl-3H-1-benzazepine-4,8-dicarboxamide

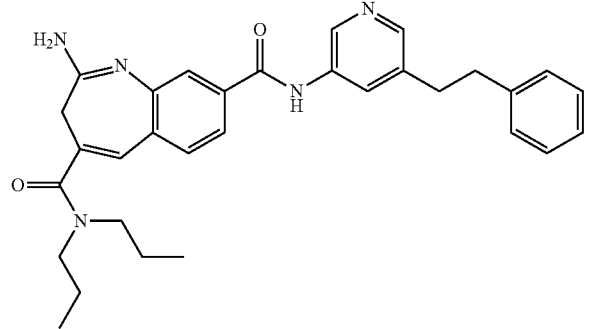 [SMILES: CCCN(CCC)C(=O)C1=Cc2ccc(C(=O)Nc3cncc(CCc4ccccc4)c3)cc2N=C(N)C1]

The title compound was prepared in analogy to Example 1 by using 5-(2-phenylethyl)pyridin-3-amine (compound 69B) instead of pyridin-3-amine. Example 69 was obtained as a white solid (45.7 mg). 1H NMR (400 MHz, CD₃OD) δ ppm=8.74 (s, 1H), 8.11 (s, 2H), 7.96 (d, J=4 Hz, 2H), 7.70 (dd, J=12 Hz, 4 Hz, 1H), 7.27-7.24 (m, 2H), 7.19-7.15 (m, 3H), 7.11 (s, 1H), 3.47 (br, 4H), 3.31 (s, 2H), 3.01-2.99 (m, 4H), 1.75-1.66 (m, 4H), 0.97-0.93 (br, 6H). MS: calc'd 510 (M+H)⁺. measured 510 (M+H)⁺.

Preparation of Compound 69B

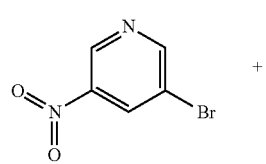

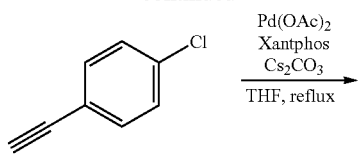

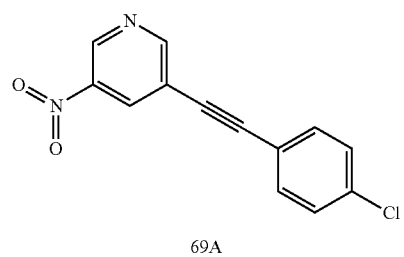

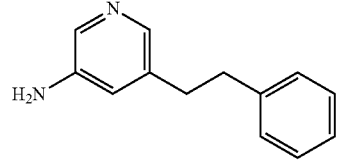

To a flask was added 3-bromo-5-nitropyridine (203 mg, 1 mmol), 1-chloro-4-ethynylbenzene (164 mg, 1.2 mmol), Pd(OAc)₂ (11.2 mg, 50 μmol), 4,5-bis(diphenylphosphino)-9,9-dimethylxanthene (57.9 mg, 100 μmol), Cs₂CO₃ (652 mg, 2 mmol) and THF (4 mL). A pale brown suspension was formed. Then it was bubbled with N2 for 5 min and heated to reflux (70° C. oil bath) for about 16 hours. The mixture was filtered through celite and the filtrate was concentrated to give a dark oil. The oil was purified via combiflash (eluting with EA/PE=0~20%~30%). About 200 mg 3-[2-(4-chlorophenyl)ethynyl]-5-nitro-pyridine (Compound 69A) was obtained as yellow solid. MS: calc'd 259 (M+H)⁺. measured 259 (M+H)⁺.

To a flask was added 3-((4-chlorophenyl)ethynyl)-5-nitropyridine (200 mg, 773 μmol) and EtOH (15 mL). A yellow suspension was formed. Then Pd(OH)₂ on carbon (20 wt %, 50% H₂O) (20 mg, 142 μmol) was added. After the mixture was sucked in vacuo and back-filled with H₂ for 5 times, it was stirred with hydrogen balloon at r.t. for about 18 hours. The mixture was filtered through celite to remove the catalyst and the filtrate was concentrated to give about 170 mg 5-(2-phenylethyl)pyridin-3-amine (Compound 69B) as yellow oil. MS: calc'd 199 (M+H)⁺. measured 199 (M+H)⁺.

Example 70

2-Amino-N8-[5-[2-(4-methoxyphenyl)ethyl]-3-pyridyl]-N4,N4-dipropyl-3H-1-benzazepine-4,8-dicarboxamide

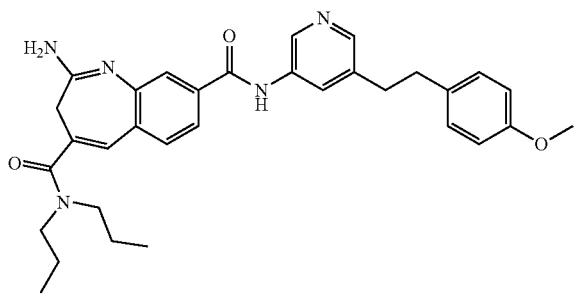 [SMILES: CCCN(CCC)C(=O)C1=Cc2ccc(C(=O)Nc3cncc(CCc4ccc(OC)cc4)c3)cc2N=C(N)C1]

The title compound was prepared in analogy to Example 1 by using 5-[2-(4-methoxyphenyl)ethyl]pyridin-3-amine (compound 70B) instead of pyridin-3-amine. Example 70 was obtained as a white solid (50 mg). 1H NMR (400 MHz, CD$_3$OD) δ ppm=8.73 (s, 1H), 8.09 (s, 1H), 8.06 (s, 1H), 7.85 (s, 1H), 7.80 (d, J=8 Hz, 1H), 7.60 (d, J=8 Hz, 1H), 7.08 (d, J=8 Hz, 2H), 7.02 (s, 1H), 6.81 (d, J=8 Hz, 2H), 3.74 (s, 3H), 3.45 (br, 4H), 3.31 (s, 2H), 2.98-2.89 (m, 4H), 1.74-1.65 (m, 4H), 0.97-0.90 (br, 6H). MS: calc'd 540 (M+H)$^+$. measured 540 (M+H)$^+$.

Preparation of Compound 70B

The title compound was prepared in analogy to compound 69B by using 1-ethynyl-4-methoxy-benzene instead of 1-chloro-4-ethynyl-benzene. MS: calc'd 229 (M+H)$^+$. measured 229 (M+H)$^+$.

Example 71

2-Amino-N8-[5-[2-[4-(aminomethyl)phenyl]ethyl]-3-pyridyl]-N4,N4-dipropyl-3H-1-benzazepine-4,8-dicarboxamide

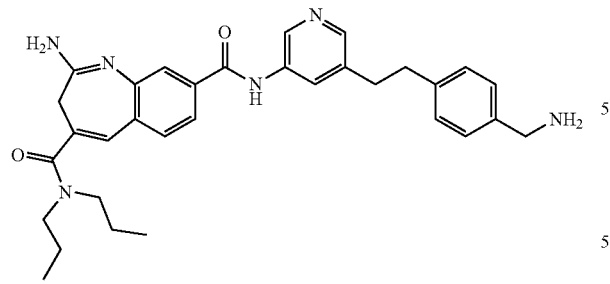

The title compound was prepared in analogy to Example 1 by using tert-butyl N-[[4-[2-(5-amino-3-pyridyl)ethyl]phenyl]methyl]carbamate (compound 71C) instead of pyridin-3-amine. Example 71 was obtained as a white solid (20.9 mg). 1H NMR (400 MHz, CD$_3$OD) δ ppm=8.76 (br, 1H), 8.21 (s, 1H), 8.08 (br, 1H), 7.99-7.97 (m, 2H), 7.72 (d, J=12 Hz, 1H), 7.36 (d, J=8 Hz, 2H), 7.29 (d, J=8 Hz, 2H), 7.12 (s, 1H), 4.07 (s, 2H), 3.48 (br, 4H), 3.38 (s, 2H), 3.04 (s, 4H), 1.75-1.66 (m, 4H), 1.00-0.94 (br, 6H). MS: calc'd 539 (M+H)$^+$. measured 539 (M+H)$^+$.

Preparation of Compound 71C

The 4-[2-(5-amino-3-pyridyl)ethyl]benzonitrile (compound 71B) was prepared in analogy to compound 69B by using 4-ethynylbenzonitrile instead of 1-chloro-4-ethynyl-benzene. MS: calc'd 224 (M+H)+. measured 224 (M+H)+.

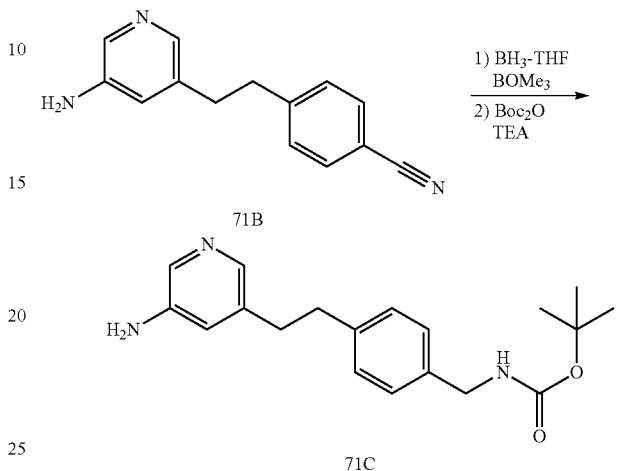

To a flask was added 4-(2-(5-aminopyridin-3-yl)ethyl)benzonitrile (compound 71B, 223 mg, 1 mmol), trimethyl borate (935 mg, 1.01 ml, 9 mmol) and borane tetrahydrofuran complex (3 mL, 3 mmol) at r.t. After the reaction mixture was stirred at 25° C. for about 13.5 hours, it was quenched with 10 mL MeOH and stirred for 1 h. Then it was filtered through celite and the filtrate was concentrated to give a brown oil. To this brown oil was added DCM (8 mL) and TEA (121 mg, 167 μl, 1.2 mmol). After the mixture was cooled with ice bath, Boc-anhydride (218 mg, 232 μl, 1.0 mmol) was added. The reaction mixture was stirred for about 2 hours. The mixture was filtered through celite and the filtrate was concentrated to give a brown slurry. After purification via combiflash (eluted with EA/PE=0~50%~100% and MeOH/EA=10%), about 110 mg tert-butyl N-[[4-[2-(5-amino-3-pyridyl)ethyl]phenyl]methyl]carbamate (compound 71C) was obtained as yellow sticky oil. MS: calc'd 328 (M+H)$^+$. measured 328 (M+H)$^+$.

Example 72

2-Amino-N8-[5-(5-aminopentyl)-3-pyridyl]-N4,N4-dipropyl-3H-1-benzazepine-4,8-dicarboxamide

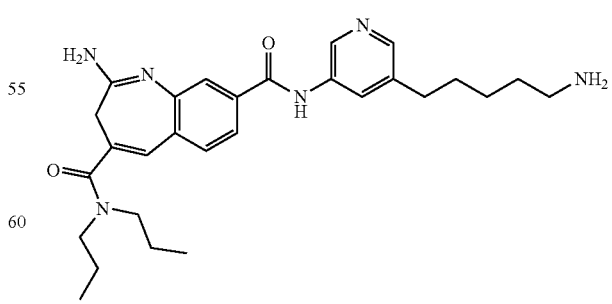

The title compound was prepared in analogy to Example 1 by using tert-butyl N-[5-(5-amino-3-pyridyl)pentyl]carbamate (compound 72B) instead of pyridin-3-amine.

Example 72 was obtained as a white solid (23.9 mg). 1H NMR (400 MHz, CD$_3$OD) δ ppm=8.70 (s, 1H), 8.20 (s, 2H), 7.88 (s, 1H), 7.85-7.82 (m, 1H), 7.64-7.62 (m, 1H), 7.04 (s, 1H), 3.46 (br, 4H), 3.31 (s, 2H), 2.94 (t, J=8 Hz, 2H), 2.75 (t, J=8 Hz, 2H), 1.80-1.65 (m, 8H), 1.52-1.48 (m, 2H), 0.97-0.88 (m, 6H). MS: calc'd 491 (M+H)$^+$. measured 491 (M+H)$^+$.

Preparation of Compound 72B

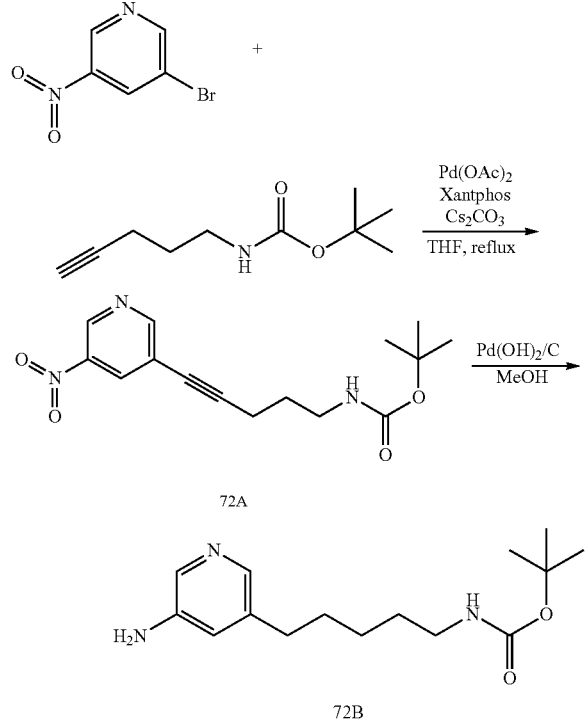

72A

72B

To a flask was added 3-bromo-5-nitropyridine (60 mg, 296 μmol), THF (2 mL), tert-butyl pent-4-yn-1-ylcarbamate (59.6 mg, 325 μmol), Pd(OAc)$_2$ (3.32 mg, 14.8 μmol), 4,5-bis(diphenylphosphino)-9,9-dimethylxanthene (17.1 mg, 29.6 μmol) and Cs$_2$CO$_3$ (193 mg, 591 μmol). Then the mixture was bubbled with N$_2$ for 5 mins and heated to reflux (70° C. oil bath) for about 4.5 hours. The mixture was filtered through celite and the filtrate was concentrated to give a brown solid. After purification via combiflash (eluted with EA/PE=0~20%~40%), tert-butyl N-[5-(5-nitro-3-pyridyl)pent-4-ynyl]carbamate (Compound 72A) was obtained as pale brown oil.

Compound 72A was dissolved in ethanol (8 mL). Then Pd(OH)$_2$ (20% on carbon with 50% H$_2$O) (10 mg, 71.2 μmol) was added. The mixture was degassed in vacuo and backfilled with H2 for five times. Then it was stirred at r.t. with hydrogen balloon for about 14 h. The mixture was filtered through celite and the filtrate was concentrated directly to give about 55 mg tert-butyl N-[5-(5-amino-3-pyridyl)pentyl]carbamate (compound 72B) as pale brown oil. MS: calc'd 280 (M+H)$^+$. measured 280 (M+H)$^+$.

Example 73

2-Amino-N8-[5-[2-(3-methoxyphenyl)ethyl]-3-pyridyl]-N4,N4-dipropyl-3H-1-benzazepine-4,8-dicarboxamide

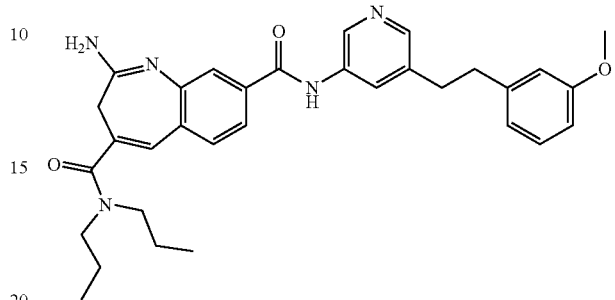

The title compound was prepared in analogy to Example 1 by using 5-[2-(3-methoxyphenyl)ethyl]pyridin-3-amine (compound 73B) instead of pyridin-3-amine. Example 73 was obtained as a white solid (29.4 mg). 1H NMR (400 MHz, CD$_3$OD) δ ppm=8.74 (s, 1H), 8.10 (s, 2H), 7.91-7.88 (m, 2H), 7.65 (d, J=8 Hz, 1H), 7.16 (t, J=8 Hz, 1H), 7.07 (s, 1H), 6.77-6.73 (m, 3H), 3.74 (s, 3H), 3.46 (br, 4H), 3.31 (s, 2H), 3.02-2.94 (m, 4H), 1.75-1.65 (m, 4H), 0.97-0.92 (br, 6H). MS: calc'd 540 (M+H)$^+$. measured 540 (M+H)$^+$.

Preparation of Compound 73B

The title compound was prepared in analogy to compound 69B by using 1-ethynyl-3-methoxy-benzene instead of 1-chloro-4-ethynyl-benzene. MS: calc'd 229 (M+H)$^+$. measured 229 (M+H)$^+$.

Example 74

2-Amino-N8-[5-(6-aminohexyl)-3-pyridyl]-N4,N4-dipropyl-3H-1-benzazepine-4,8-dicarboxamide

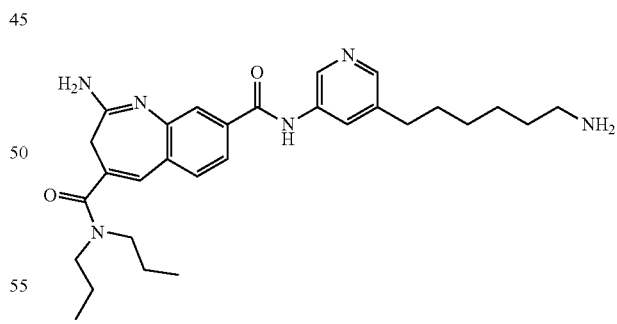

The title compound was prepared in analogy to Example 1 by using tert-butyl N-[6-(5-amino-3-pyridyl)hexyl]carbamate (compound 74B) instead of pyridin-3-amine. Example 74 was obtained as a white solid (17.0 mg). 1H NMR (400 MHz, CD$_3$OD) δ ppm=8.68 (s, 1H), 8.20-8.19 (m, 2H), 7.83 (s, 1H), 7.77 (d, J=8 Hz, 1H), 7.58 (d, J=8 Hz, 1H), 7.01 (s, 1H), 3.47-3.43 (br, 4H), 3.31 (s, 2H), 2.92 (t, J=8 Hz, 2H), 2.73 (t, J=8 Hz, 2H), 1.75-1.65 (m, 8H), 1.47-1.45 (m, 4H), 0.98-0.90 (m, 6H). MS: calc'd 505 (M+H)$^+$. measured 505 (M+H)$^+$.

Preparation of Compound 74B

The title compound was prepared in analogy to compound 72B by using tert-butyl N-but-5-ynylcarbamate instead of tert-butyl N-pent-4-ynylcarbamate. MS: calc'd 294 (M+H)+. measured 294 (M+H)+.

Example 75

2-Amino-N8-[6-(3-aminopropyl)-3-pyridyl]-N4,N4-dipropyl-3H-1-benzazepine-4,8-dicarboxamide

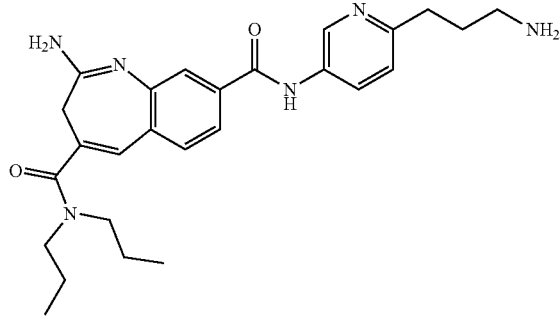 [SMILES: CCCN(CCC)C(=O)C1=Cc2ccc(C(=O)Nc3ccc(CCCN)nc3)cc2N=C(N)C1]

The title compound was prepared in analogy to Example 1 by using tert-butyl N-[3-(5-amino-2-pyridyl)propyl]carbamate (compound 75B) instead of pyridin-3-amine. Example 75 was obtained as a white solid (33.6 mg). 1H NMR (400 MHz, CD$_3$OD) δ ppm=8.88 (s, 1H), 8.18 (dd, J=8 Hz, 4 Hz, 1H), 7.92 (s, 1H), 7.88 (d, J=12 Hz, 1H), 7.65 (d, J=8 Hz, 1H), 7.38 (d, J=8 Hz, 1H), 7.06 (s, 1H), 3.46 (br, 4H), 3.31 (s, 2H), 3.00 (t, J=8 Hz, 2H), 2.91 (t, J=8 Hz, 2H), 2.11-2.03 (m, 2H), 1.74-1.65 (m, 4H), 0.9-0.92 (br, 6H). MS: calc'd 463 (M+H)+. measured 463 (M+H)+.

Preparation of Compound 75B

The title compound was prepared in analogy to compound 72B by using 2-bromo-5-nitro-pyridine instead of 3-bromo-5-nitro-pyridine and tert-butyl N-prop-2-ynylcarbamate instead of tert-butyl N-pent-4-ynylcarbamate. MS: calc'd 252 (M+H)+. measured 252 (M+H)+.

Example 76

2-Amino-N8-[5-(4-aminobutyl)-3-pyridyl]-N4,N4-dipropyl-3H-1-benzazepine-4,8-dicarboxamide

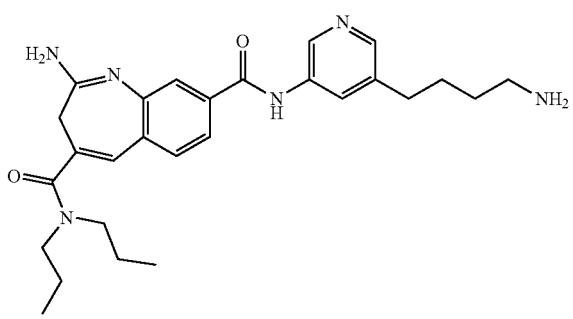 [SMILES: CCCN(CCC)C(=O)C1=Cc2ccc(C(=O)Nc3cncc(CCCCN)c3)cc2N=C(N)C1]

The title compound was prepared in analogy to Example 1 by using tert-butyl N-[4-(5-amino-3-pyridyl)butyl]carbamate (compound 76B) instead of pyridin-3-amine. Example 76 was obtained as a white solid (51.7 mg). 1H NMR (400 MHz, CD$_3$OD) δ ppm=8.91 (s, 1H), 8.35-8.31 (m, 2H), 8.02 (s, 1H), 7.99 (d, J=8 Hz, 1H), 7.72 (d, J=8 Hz, 1H), 7.12 (s, 1H), 3.48 (br, 4H), 3.38 (s, 2H), 2.98 (t, J=8 Hz, 2H), 2.82 (t, J=8 Hz, 2H), 1.83-1.66 (m, 8H), 0.99-0.92 (br, 6H). MS: calc'd 477 (M+H)+. measured 477 (M+H)+.

Preparation of Compound 76B

The title compound was prepared in analogy to compound 72B by using tert-butyl N-but-3-ynylcarbamate instead of tert-butyl N-pent-4-ynylcarbamate. MS: calc'd 266 (M+H)+. measured 266 (M+H)+.

Example 77

2-Amino-N8-[6-(4-aminobutyl)-3-pyridyl]-N4,N4-dipropyl-3H-1-benzazepine-4,8-dicarboxamide

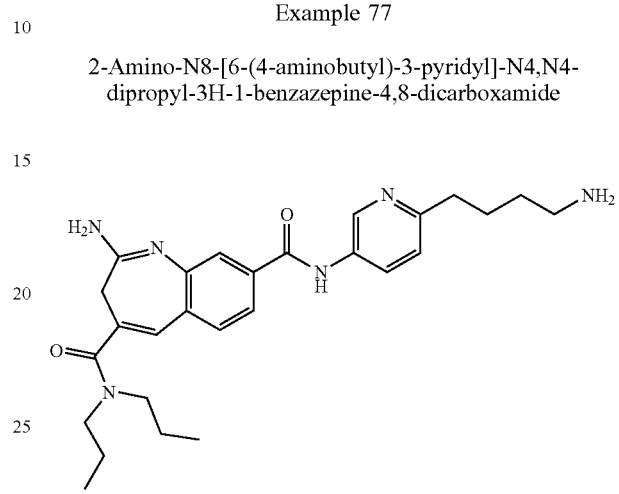

The title compound was prepared in analogy to Example 1 by using tert-butyl N-[4-(5-amino-2-pyridyl)butyl]carbamate (compound 77B) instead of pyridin-3-amine. Example 77 was obtained as a white solid (51.6 mg). 1H NMR (400 MHz, CD$_3$OD) δ ppm=9.10 (m, 1H), 8.38 (m, 1H), 8.02-7.98 (m, 2H), 7.72 (d, J=8 Hz, 1H), 7.64-7.62 (m, 1H), 7.12 (s, 1H), 3.48 (br, 4H), 3.38 (s, 2H), 3.01-2.94 (m, 4H), 1.87-1.82 (m, 2H), 1.78-1.69 (m, 6H), 0.99-0.92 (br, 6H). MS: calc'd 477 (M+H)+. measured 477 (M+H)+.

Preparation of Compound 77B

The title compound was prepared in analogy to compound 72B by using 2-bromo-5-nitro-pyridine instead of 3-bromo-5-nitro-pyridine and tert-butyl N-but-3-ynylcarbamate instead of tert-butyl N-pent-4-ynylcarbamate. MS: calc'd 266 (M+H)+. measured 266 (M+H)+.

Example 78

2-Amino-N8-[5-[(dimethylamino)methyl]-3-pyridyl]-N4,N4-dipropyl-3H-1-benzazepine-4,8-dicarboxamide

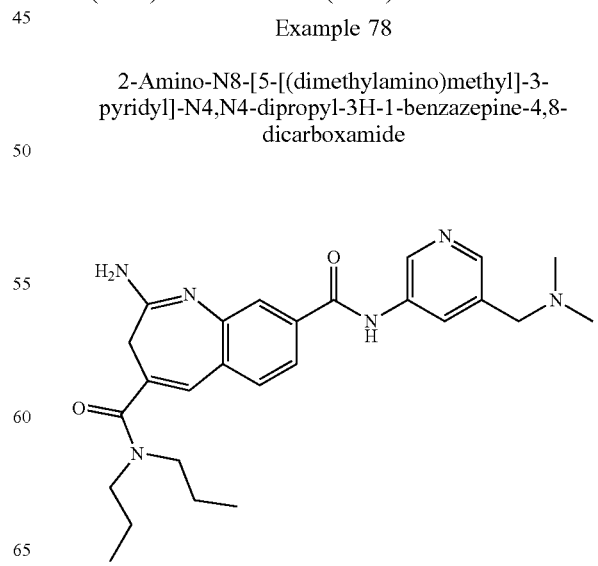

The title compound was prepared in analogy to Example 1 by using 5-[(dimethyl-amino)methyl]pyridin-3-amine instead of pyridin-3-amine. Example 78 was obtained as a white solid (16 mg). 1H NMR (400 MHz, CD₃OD) δ ppm=8.99 (br. s., 1H), 8.65 (br. s., 1H), 8.52 (br. s., 1H), 7.98-8.09 (m, 2H), 7.74 (d, J=8.03 Hz, 1H), 7.14 (br. s., 1H), 4.48 (br. s., 2H), 3.49 (br. s., 4H), 3.40 (br. s., 2H), 2.96 (br. s., 6H), 1.72 (d, J=6.40 Hz, 4H), 0.88-1.08 (m, 6H). MS: calc'd 463 (M+H)⁺. measured 463 (M+H)⁺.

Example 79

2-Amino-N4-(cyclopropylmethyl)-N8-(5-ethoxy-3-pyridyl)-N4-propyl-3H-1-benzazepine-4,8-dicarboxamide

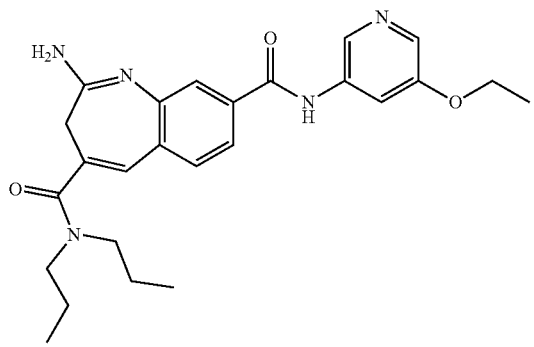 [SMILES: CCCN(CCC)C(=O)C1=Cc2ccc(C(=O)Nc3cncc(OCC)c3)cc2N=C(N)C1]

The title compound was prepared in analogy to Example 26 by using 5-ethoxypyridin-3-amine instead of m-toluidine and N-(cyclopropylmethyl)propan-1-amine instead of 3-(propylamino)propan-1-ol. Example 79 was obtained as a white solid (16.5 mg). 1H NMR (400 MHz, CD₃OD) δ ppm=8.74 (br, 1H), 8.17-8.12 (m, 2H), 8.02-7.98 (m, 2H), 7.73 (d, J=8 Hz, 1H), 7.14 (s, 1H), 4.25-4.20 (m, 2H), 3.58 (t, J=8 Hz, 2H), 3.42 (d, J=8 Hz, 2H), 3.39 (s, 2H), 1.78-1.69 (m, 2H), 1.48 (t, J=8 Hz, 3H), 1.11 (brs, 1H), 0.96 (br s, 3H), 0.63-0.61 (br, 2H), 0.31 (br s, 2H). MS: calc'd 462 (M+H)⁺. measured 462 (M+H)⁺.

Example 80

2-Amino-N8-[5-(2-aminoethyl)-3-pyridyl]-N4,N4-dipropyl-3H-1-benzazepine-4,8-dicarboxamide

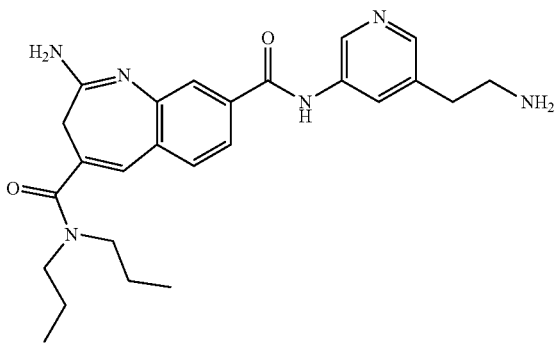 [SMILES: CCCN(CCC)C(=O)C1=Cc2ccc(C(=O)Nc3cncc(CCN)c3)cc2N=C(N)C1]

The title compound was prepared in analogy to Example 1 by using tert-butyl N-[2-(5-amino-3-pyridyl)ethyl]carbamate (compound 80E) instead of pyridin-3-amine. Example 80 was obtained as a white solid (63 mg). 1H NMR (400 MHz, CD₃OD) δ ppm=9.02 (s, 1H), 8.49 (s, 1H), 8.40 (s, 1H), 8.04 (s, 1H), 8.01-7.98 (d, J=10 Hz, 1H), 7.73-7.71 (d, J=8.4 Hz, 1H), 7.11 (s, 1H), 3.47 (br. s., 4H), 3.37 (s, 2H), 3.31-3.28 (m, 2H), 3.14-3.10 (m, 2H), 1.73-1.67 (m, 4H), 0.96 (br. s., 6H). MS: calc'd 449.4 (M+H)⁺. measured 449.4 (M+H)⁺.

Preparation of Compound 80E

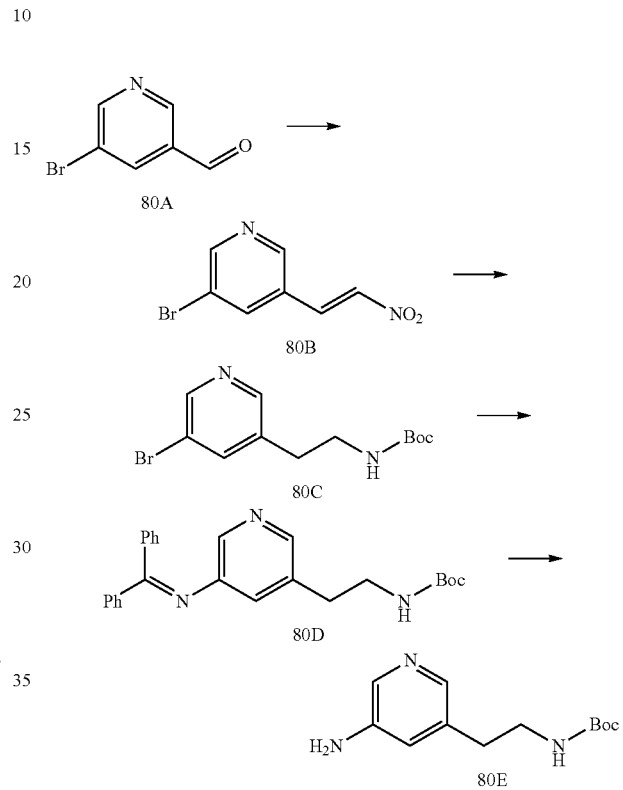

Preparation of Compound 80B

To the solution of 5-bromonicotinaldehyde (5.0 g, 27.0 mmol) in DCM (100 mL) was added Et₃N (5.46 g, 54.1 mmol) and CH₃NO₂ (8.2 g, 135.1 mmol). The solution was stirred at 20° C. for 15 hrs. The reaction solution was concentrated in vacuo to give a crude product (6.7 g) as yellow oil, which was dissolved in DCM (100 mL). Then DMAP (3.63 g, 29.7 mmol) and acetic anhydride (3.58 g, 35.1 mmol) was added at 0° C. After the solution was stirred at 20° C. for 2 hours, it was poured into water (200 mL). The mixture was extracted with DCM (500 mL). The organic layer was washed with brine (200 mL) and concentrated in vacuo. The residue was purified through column chromatography (PE/EtOAc=10/1) to give (E)-3-bromo-5-(2-nitrovinyl)pyridine (compound 80B, 4.1 g, 66.5% of yield for two steps) as a yellow solid. 1H NMR (400 MHz, CDCl₃)=8.78 (s, 1H), 8.71 (s, 1H), 8.02 (s, 1H), 7.97-7.92 (d, J=18.4 Hz, 1H), 7.63-7.59 (d, J=18.4 Hz, 1H).

Preparation of Compound 80C

To the solution of (E)-3-bromo-5-(2-nitrovinyl)pyridine (compound 80B, 2.0 g, 8.7 mmol) in THF (60 mL) was added LiAlH₄ (1.33 g, 35.1 mmol) in portions at −30° C. Then the mixture was warmed to −10° C. and stirred for 3 hours. The reaction was quenched by water and then Boc₂O (2.3 g, 10.5 mmol) was added. After the solution was stirred at 20° C. for 3 hours, it was poured into water (50 mL) and then extracted with EtOAc (100 mL×2). The combined organic layers were washed with brine (100 mL), dried over $Na_2SO_4$ and concentrated in vacuo. The residue (with another batch from 1.0 g of compound 80B) was purified through column chromatography (DCM/MeOH=100/1~30/1) to give tert-butyl (2-(5-bromopyridin-3-yl)ethyl)carbamate (compound 80C, 1.1 g, 28.0% of yield for two batches from 3.0 g of compound 80B) as yellow oil. MS: calc'd 301 $(M+H)^+$. measured 301.1 ($\{79Br\}M+H)^+$, 303.1 ($\{81Br\}M+H)^+$.

Preparation of Compound 80D

To the solution of tert-butyl (2-(5-bromopyridin-3-yl)ethyl)carbamate (compound 80C, 800 mg, 2.67 mmol) in dioxane (20 mL) was added diphenylmethanimine (482 mg, 2.67 mmol), Xant-phos (463 mg, 0.80 mmol) and $Cs_2CO_3$ (2.61 g, 8.01 mmol). The mixture was degassed for three times and then $Pd_2(dba)_3$ (244 mg, 0.267 mmol) was added. The mixture was further degassed for three times and stirred at 80° C. for 12 hrs. The reaction solution was diluted with EtOAc (50 mL) and then washed with brine (50 mL), dried over $Na_2SO_4$ and concentrated in vacuo to give crude tert-butyl (2-(5-((diphenylmethylene)amino)pyridin-3-yl)ethyl)carbamate (compound 80D, 1.07 g) as a yellow oil, which was dissolved in MeOH (30 mL) followed by the addition of AcONa (1.09 g, 13.35 mmol) and $NH_2OH\times HCl$ (278 mg, 4.0 mmol). After the mixture was stirred at 25° C. for 2 hours, it was concentrated in vacuo. The residue was diluted with water (50 mL) and then extracted with DCM (50 mL×3). The combined organic layers were dried over $Na_2SO_4$, concentrated in vacuo. The residue was purified (with another batch from 0.3 g compound 80C) through column chromatography (DCM/MeOH=100/1~20/1) to give tert-butyl (2-(5-aminopyridin-3-yl)ethyl)carbamate (compound 80E, 230 mg, 26.4% of yield from a total of 1.1 g compound 80C) as a yellow solid. MS: calc'd 238 $(M+H)^+$. measured 238 $(M+H)^+$.

The invention claimed is:

1. A compound of the formula

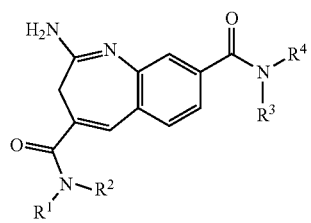

wherein
R$^1$ is $C_{3-7}$-alkyl or $C_{3-7}$-cycloalkyl;
R$^2$ is selected from the group consisting of $C_{1-7}$-alkyl, hydroxy-$C_{1-7}$-alkyl, $C_{2-7}$-alkenyl, $C_{3-7}$-alkinyl, amino-$C_{1-7}$-alkoxy-$C_{1-7}$-alkyl, amino-$C_{1-7}$-alkoxy-$C_{1-7}$-alkoxy-$C_{1-7}$-alkyl, halogen-$C_{1-7}$-alkyl, $C_{3-7}$-cycloalkyl-$C_{1-7}$-alkyl and phenyl-$C_{1-7}$-alkyl, wherein phenyl is unsubstituted or substituted by amino-$C_{1-7}$-alkyl;
R$^3$ is hydrogen;
R$^4$ is selected from the group consisting of
phenyl, said phenyl being unsubstituted or substituted by one or two groups selected from the group consisting of $C_{1-7}$-alkyl, halogen, halogen-$C_{1-7}$-alkyl, $C_{1-7}$-alkoxy, hydroxy-$C_{1-7}$-alkyl, amino-$C_{1-7}$-alkyl, $C_{1-7}$-alkyl-amino-$C_{1-7}$-alkyl, di-$C_{1-7}$-alkyl-amino-$C_{1-7}$-alkyl, amino-$C_{2-7}$-alkenyl, $C_{1-7}$-alkyl-amino-$C_{2-7}$-alkenyl, di-$C_{1-7}$-alkyl-amino-$C_{2-7}$-alkenyl, amino-$C_{2-7}$-alkinyl, $C_{1-7}$-alkyl-amino-$C_{2-7}$-alkinyl, di-$C_{1-7}$-alkyl-amino-$C_{2-7}$-alkinyl, benzyloxycarbonylamino-$C_{1-7}$-alkyl, amino-$C_{1-7}$-alkoxy, amino-$C_{1-7}$-alkoxy-$C_{1-7}$-alkoxy, amino-$C_{1-7}$-alkoxy-$C_{1-7}$-alkyl, amino-$C_{1-7}$-alkoxy-$C_{1-7}$-alkoxy-$C_{1-7}$-alkyl, $C_{1-7}$-alkylsulfonyl, heterocyclylcarbonyl and phenyl-$C_{1-7}$-alkyl, wherein phenyl is unsubstituted or substituted by $C_{1-7}$-alkoxy or amino-$C_{1-7}$-alkyl, and
heteroaryl, said heteroaryl being a 5- or 6-membered aromatic ring containing one, two or three heteroatoms selected from N, O or S and being unsubstituted or substituted by one or two groups selected from the group consisting of $C_{1-7}$-alkyl, halogen, halogen-$C_{1-7}$-alkyl, $C_{1-7}$-alkoxy, hydroxy-$C_{1-7}$-alkyl, amino-$C_{1-7}$-alkyl, $C_{1-7}$-alkyl-amino-$C_{1-7}$-alkyl, di-$C_{1-7}$-alkyl-amino-$C_{1-7}$-alkyl, amino-$C_{2-7}$-alkenyl, $C_{1-7}$-alkyl-amino-$C_{2-7}$-alkenyl, di-$C_{1-7}$-alkyl-amino-$C_{2-7}$-alkenyl, amino-$C_{2-7}$-alkinyl, $C_{1-7}$-alkyl-amino-$C_{2-7}$-alkinyl, di-$C_{1-7}$-alkyl-amino-$C_{2-7}$-alkinyl, benzyloxycarbonylamino-$C_{1-7}$-alkyl, amino-$C_{1-7}$-alkoxy, amino-$C_{1-7}$-alkoxy-$C_{1-7}$-alkoxy, amino-$C_{1-7}$-alkoxy-$C_{1-7}$-alkyl, amino-$C_{1-7}$-alkoxy-$C_{1-7}$-alkoxy-$C_{1-7}$-alkyl, $C_{1-7}$-alkylsulfonyl, heterocyclylcarbonyl and phenyl-$C_{1-7}$-alkyl, wherein phenyl is unsubstituted or substituted by $C_{1-7}$-alkoxy or amino-$C_{1-7}$-alkyl,
or a pharmaceutically acceptable salt thereof.

2. A compound of formula I according to claim 1, or a pharmaceutically acceptable salt thereof, wherein R$^1$ is $C_{1-7}$-alkyl.

3. A compound of formula I according to claim 1, or a pharmaceutically acceptable salt thereof, wherein R$^1$ is propyl or butyl.

4. A compound of formula I according to claim 1, or a pharmaceutically acceptable salt thereof, wherein R$^2$ is selected from the group consisting of $C_{1-7}$-alkyl, $C_{3-7}$-alkinyl, halogen-$C_{1-7}$-alkyl, $C_{3-7}$-cycloalkyl-$C_{1-7}$-alkyl and hydroxy-$C_{1-7}$-alkyl.

5. A compound of formula I according to claim 1, or a pharmaceutically acceptable salt thereof, wherein R$^2$ is $C_{1-7}$-alkyl.

6. A compound of formula I according to claim 1, or a pharmaceutically acceptable salt thereof, wherein R$^4$ is a 5- or 6-membered heteroaryl ring containing one, two or three heteroatoms selected from N, O or S and being unsubstituted or substituted by one or two groups selected from the group consisting of $C_{1-7}$-alkyl, halogen, halogen-$C_{1-7}$-alkyl, $C_{1-7}$-alkoxy, hydroxy-$C_{1-7}$-alkyl, $C_{1-7}$-alkyl-amino-$C_{1-7}$-alkyl, di-$C_{1-7}$-alkyl-amino-$C_{1-7}$-alkyl, amino-$C_{2-7}$-alkenyl, $C_{1-7}$-alkyl-amino-$C_{2-7}$-alkenyl, di-$C_{1-7}$-alkyl-amino-$C_{2-7}$-alkenyl, $C_{1-7}$-alkyl-amino-$C_{2-7}$-alkinyl, di-$C_{1-7}$-alkyl-amino-$C_{2-7}$-alkinyl, benzyloxycarbonylamino-$C_{1-7}$-alkyl, amino-$C_{1-7}$-alkoxy, amino-$C_{1-7}$-alkoxy-$C_{1-7}$-alkoxy, amino-$C_{1-7}$-alkoxy-$C_{1-7}$-alkyl, amino-$C_{1-7}$-alkoxy-$C_{1-7}$-alkoxy-$C_{1-7}$-alkyl, $C_{1-7}$-alkylsulfonyl, heterocyclylcarbonyl and phenyl-$C_{1-7}$-alkyl, wherein phenyl is unsubstituted or substituted by $C_{1-7}$-alkoxy or amino-$C_{1-7}$-alkyl.

7. A compound of formula I according to claim 1, or a pharmaceutically acceptable salt thereof, wherein R$^4$ is a 5- or 6-membered heteroaryl ring containing one, two or three heteroatoms selected from N, O or S and being substituted by one or two groups selected from the group consisting of $C_{1-7}$-alkyl, halogen, $C_{1-7}$-alkoxy, hydroxy-$C_{1-7}$-alkyl, amino-$C_{1-7}$-alkyl, di-$C_{1-7}$-alkyl-amino-$C_{1-7}$-alkyl, amino-$C_{2-7}$-alkenyl, amino-$C_{2-7}$-alkinyl, benzyloxycarbonylamino-$C_{1-7}$-alkyl, amino-$C_{1-7}$-alkoxy and phenyl-$C_{1-7}$-alkyl, wherein phenyl is unsubstituted or substituted by $C_{1-7}$-alkoxy or amino-$C_{1-7}$-alkyl.

8. A compound of formula I according to claim 1, or a pharmaceutically acceptable salt thereof, wherein $R^4$ is a 5- or 6-membered heteroaryl ring is selected from the group consisting of imidazolyl, pyrazolyl, oxazolyl, thiazolyl, pyridyl, pyridazinyl and pyrimidinyl.

9. A compound of formula I according to claim 1, or a pharmaceutically acceptable salt thereof, wherein the 6-membered heteroaryl ring is pyridyl.

10. A compound of formula I according to claim 1, or a pharmaceutically acceptable salt thereof, wherein $R^4$ is phenyl, said phenyl being unsubstituted or substituted by one or two groups selected from the group consisting of $C_{1-7}$-alkyl, halogen, halogen-$C_{1-7}$-alkyl, $C_{1-7}$-alkoxy, hydroxy-$C_{1-7}$-alkyl, amino-$C_{1-7}$-alkyl, $C_{1-7}$-alkyl-amino-$C_{1-7}$-alkyl, di-$C_{1-7}$-alkyl-amino-$C_{1-7}$-alkyl, amino-$C_{2-7}$-alkenyl, $C_{1-7}$-alkyl-amino-$C_{2-7}$-alkenyl, di-$C_{1-7}$-alkyl-amino-$C_{2-7}$-alkenyl, amino-$C_{2-7}$-alkinyl, $C_{1-7}$-alkyl-amino-$C_{2-7}$-alkinyl, di-$C_{1-7}$-alkyl-amino-$C_{2-7}$-alkinyl, benzyloxycarbonylamino-$C_{1-7}$-alkyl, amino-$C_{1-7}$-alkoxy, amino-$C_{1-7}$-alkoxy-$C_{1-7}$-alkyl, amino-$C_{1-7}$-alkoxy-$C_{1-7}$-alkoxy-$C_{1-7}$-alkyl, $C_{1-7}$-alkylsulfonyl, heterocyclylcarbonyl and phenyl-$C_{1-7}$-alkyl, wherein phenyl is unsubstituted or substituted by $C_{1-7}$-alkoxy or amino-$C_{1-7}$-alkyl.

11. A compound of formula I according to claim 1, or a pharmaceutically acceptable salt thereof, wherein $R^4$ is phenyl, said phenyl being unsubstituted or substituted by one or two groups selected from the group consisting of $C_{1-7}$-alkyl, halogen, halogen-$C_{1-7}$-alkyl, $C_{1-7}$-alkoxy, amino-$C_{1-7}$-alkyl, amino-$C_{1-7}$-alkoxy, amino-$C_{1-7}$-alkoxy-$C_{1-7}$-alkoxy, amino-$C_{1-7}$-alkoxy-$C_{1-7}$-alkyl, amino-$C_{1-7}$-alkoxy-$C_{1-7}$-alkoxy-$C_{1-7}$-alkyl, $C_{1-7}$-alkylsulfonyl and heterocyclylcarbonyl.

12. A compound of formula I according to claim 1, or a pharmaceutically acceptable salt thereof, wherein $R^4$ is phenyl substituted by one group selected from the group consisting of $C_{1-7}$-alkyl, halogen, halogen-$C_{1-7}$-alkyl, $C_{1-7}$-alkoxy, amino-$C_{1-7}$-alkyl, amino-$C_{1-7}$-alkoxy, amino-$C_{1-7}$-alkoxy-$C_{1-7}$-alkoxy, amino-$C_{1-7}$-alkoxy-$C_{1-7}$-alkyl, amino-$C_{1-7}$-alkoxy-$C_{1-7}$-alkoxy-$C_{1-7}$-alkyl, $C_{1-7}$-alkylsulfonyl and heterocyclylcarbonyl.

13. A compound of the formula I according to claim 1, wherein
$R^1$ is $C_{3-7}$-alkyl or $C_{3-7}$-cycloalkyl;
$R^2$ is selected from the group consisting of $C_{1-7}$-alkyl, $C_{2-7}$-alkenyl, $C_{3-7}$-alkinyl, hydroxy-$C_{1-7}$-alkyl, amino-$C_{1-7}$-alkoxy-$C_{1-7}$-alkoxy-$C_{1-7}$-alkyl, halogen-$C_{1-7}$-alkyl and $C_{3-7}$-cycloalkyl-$C_{1-7}$-alkyl;
$R^3$ is hydrogen;
$R^4$ is selected from the group consisting of
phenyl, said phenyl being unsubstituted or substituted by one or two groups selected from the group consisting of $C_{1-7}$-alkyl, halogen, halogen-$C_{1-7}$-alkyl, $C_{1-7}$-alkoxy, hydroxy-$C_{1-7}$-alkyl, amino-$C_{1-7}$-alkyl, amino-$C_{2-7}$-alkenyl, amino-$C_{2-7}$-alkinyl, amino-$C_{1-7}$-alkoxy, amino-$C_{1-7}$-alkoxy-$C_{1-7}$-alkoxy, amino-$C_{1-7}$-alkoxy-$C_{1-7}$-alkoxy-$C_{1-7}$-alkyl, $C_{1-7}$-alkylsulfonyl and heterocyclylcarbonyl, and
heteroaryl, said heteroaryl being a 5- or 6-membered aromatic ring containing one, two or three heteroatoms selected from N, O or S and being unsubstituted or substituted by one or two groups selected from the group consisting of $C_{1-7}$-alkyl, halogen, halogen-$C_{1-7}$-alkyl, $C_{1-7}$-alkoxy, hydroxy-$C_{1-7}$-alkyl, amino-$C_{1-7}$-alkyl, amino-$C_{2-7}$-alkenyl, amino-$C_{2-7}$-alkinyl, amino-$C_{1-7}$-alkoxy, amino-$C_{1-7}$-alkoxy-$C_{1-7}$-alkoxy, amino-$C_{1-7}$-alkoxy-$C_{1-7}$-alkoxy-C alkyl, $C_{1-7}$-alkylsulfonyl and heterocyclylcarbonyl,
or a pharmaceutically acceptable salt thereof.

14. A compound selected from the group consisting of
2-amino-N4,N4-dipropyl-N8-(3-pyridyl)-3H-1-benzazepine-4,8-dicarboxamide,
2-amino-N4,N4-dipropyl-N8-pyrimidin-5-yl-3H-1-benzazepine-4,8-dicarboxamide,
2-amino-N4,N4-dipropyl-N8-(4-pyridyl)-3H-1-benzazepine-4,8-dicarboxamide,
2-amino-N4,N4-dipropyl-N8-phenyl-3H-1-benzazepine-4,8-dicarboxamide,
2-amino-N8-[6-(aminomethyl)-3-pyridyl]-N4,N4-dipropyl-3H-1-benzazepine-4,8-dicarboxamide,
2-amino-N8-[5-(hydroxymethyl)-3-pyridyl]-N4,N4-dipropyl-3H-1-benzazepine-4,8-dicarboxamide,
2-amino-N8-[6-(hydroxymethyl)-3-pyridyl]-N4,N4-dipropyl-3H-1-benzazepine-4,8-dicarboxamide,
2-amino-N8-(3-methylsulfonylphenyl)-N4,N4-dipropyl-3H-1-benzazepine-4,8-dicarboxamide,
2-amino-N4,N4-dipropyl-N8-thiazol-5-yl-3H-1-benzazepine-4,8-dicarboxamide,
2-amino-N8-(4-chlorophenyl)-N4,N4-dipropyl-3H-1-benzazepine-4,8-dicarboxamide,
2-amino-N4,N4-dipropyl-N8-thiazol-2-yl-3H-1-benzazepine-4,8-dicarboxamide,
2-amino-N8-(3-methylimidazol-4-yl)-N4,N4-dipropyl-3H-1-benzazepine-4,8-dicarboxamide,
2-amino-N8-(4-fluorophenyl)-N4,N4-dipropyl-3H-1-benzazepine-4,8-dicarboxamide,
2-amino-N8-(m-tolyl)-N4,N4-dipropyl-3H-1-benzazepine-4,8-dicarboxamide,
2-amino-N4,N4-dipropyl-N8-[3-(pyrrolidine-1-carbonyl)phenyl]-3H-1-benzazepine-4,8-dicarboxamide,
2-amino-N4,N4-dipropyl-N8-[5-(pyrrolidine-1-carbonyl)-3-pyridyl]-3H-1-benzazepine-4,8-dicarboxamide,
2-amino-N8-[3-(2-aminoethyl)phenyl]-N4,N4-dipropyl-3H-1-benzazepine-4,8-dicarboxamide,
2-amino-N8-(5-methyl-3-pyridyl)-N4,N4-dipropyl-3H-1-benzazepine-4,8-dicarboxamide,
2-amino-N8-(3-fluorophenyl)-N4,N4-dipropyl-3H-1-benzazepine-4,8-dicarboxamide,
2-amino-N8-(5-fluoro-3-pyridyl)-N4,N4-dipropyl-3H-1-benzazepine-4,8-dicarboxamide,
2-amino-N8-(2-methyl-3-pyridyl)-N4,N4-dipropyl-3H-1-benzazepine-4,8-dicarboxamide,
2-amino-N8-(6-methyl-3-pyridyl)-N4,N4-dipropyl-3H-1-benzazepine-4,8-dicarboxamide,
2-amino-N8-(3,5-dimethylphenyl)-N4,N4-dipropyl-3H-1-benzazepine-4,8-dicarboxamide,
2-amino-N8-[4-(aminomethyl)phenyl]-N4,N4-dipropyl-3H-1-benzazepine-4,8-dicarboxamide,
2-amino-N8-[4-(2-aminoethyl)phenyl]-N4,N4-dipropyl-3H-1-benzazepine-4,8-dicarboxamide,
2-amino-N4-(3-hydroxypropyl)-N8-(m-tolyl)-N4-propyl-3H-1-benzazepine-4,8-dicarboxamide,
2-amino-N8-(o-tolyl)-N4,N4-dipropyl-3H-1-benzazepine-4,8-dicarboxamide,
2-amino-N4,N4-dipropyl-N8-(p-tolyl)-3H-1-benzazepine-4,8-dicarboxamide,
2-amino-N8-(3-ethylphenyl)-N4,N4-dipropyl-3H-1-benzazepine-4,8-dicarboxamide,
2-amino-N8-(3-methoxyphenyl)-N4,N4-dipropyl-3H-1-benzazepine-4,8-dicarboxamide,
2-amino-N4,N4-dipropyl-N8-[3-(trifluoromethyl)phenyl]-3H-1-benzazepine-4,8-dicarboxamide,
2-amino-N8-(3-chlorophenyl)-N4,N4-dipropyl-3H-1-benzazepine-4,8-dicarboxamide,
2-amino-N8-[5-(aminomethyl)-3-pyridyl]-N4,N4-dipropyl-3H-1-benzazepine-4,8-dicarboxamide,
2-amino-N4,N4-dipropyl-N8-pyridazin-4-yl-3H-1-benzazepine-4,8-dicarboxamide,
2-amino-N8-(6-ethoxy-3-pyridyl)-N4,N4-dipropyl-3H-1-benzazepine-4,8-dicarboxamide,
2-amino-N8-[3-(aminomethyl)phenyl]-N4,N4-dipropyl-3H-1-benzazepine-4,8-dicarboxamide,
2-amino-N8-(1-methylpyrazol-3-yl)-N4,N4-dipropyl-3H-1-benzazepine-4,8-dicarboxamide,
2-amino-N8-oxazol-2-yl-N4,N4-dipropyl-3H-1-benzazepine-4,8-dicarboxamide, 2-amino-N4-(3-hydroxypropyl)-N4-propyl-N8-(3-pyridyl)-3H-1-benzazepine-4,8-dicarboxamide,
2-amino-N8-(5-methoxy-3-pyridyl)-N4,N4-dipropyl-3H-1-benzazepine-4,8-dicarboxamide,
2-amino-N8-(m-tolyl)-N4-propyl-N4-prop-2-ynyl-3H-1-benzazepine-4,8-dicarboxamide,
2-amino-N4,N4-dibutyl-N8-(m-tolyl)-3H-1-benzazepine-4,8-dicarboxamide,
2-amino-N8-[3-(aminomethyl)-5-methyl-phenyl]-N4,N4-dipropyl-3H-1-benzazepine-4,8-dicarboxamide,
2-amino-N8-(5-ethoxy-3-pyridyl)-N4,N4-dipropyl-3H-1-benzazepine-4,8-dicarboxamide,
2-amino-N8-[3-[2-(2-aminoethoxy)ethoxy]phenyl]-N4,N4-dipropyl-3H-1-benzazepine-4,8-dicarboxamide,
2-amino-N8-[5-(5-aminopentoxy)-3-pyridyl]-N4,N4-dipropyl-3H-1-benzazepine-4,8-dicarboxamide,
2-amino-N8-[3-[2-(2-aminoethoxy)ethoxymethyl]phenyl]-N4,N4-dipropyl-3H-1-benzazepine-4,8-dicarboxamide,
2-amino-N8-[5-(3-aminoprop-1-ynyl)-3-pyridyl]-N4,N4-dipropyl-3H-1-benzazepine-4,8-dicarboxamide,
2-amino-N4-[3-[2-(2-aminoethoxy)ethoxy]propyl]-N8-(m-tolyl)-N4-propyl-3H-1-benzazepine-4,8-dicarboxamide,
2-amino-N8-[5-(3-aminopropyl)-3-pyridyl]-N4,N4-dipropyl-3H-1-benzazepine-4,8-dicarboxamide,
2-amino-N8-(m-tolyl)-N4-propyl-N4-(3,3,3-trifluoropropyl)-3H-1-benzazepine-4,8-dicarboxamide,
2-amino-N8-[5-[(E)-3-aminoprop-1-enyl]-3-pyridyl]-N4,N4-dipropyl-3H-1-benzazepine-4,8-dicarboxamide, and
2-amino-N4-(cyclopropylmethyl)-N8-(m-tolyl)-N4-propyl-3H-1-benzazepine-4,8-dicarboxamide,
or a pharmaceutically acceptable salt thereof.

15. A compound selected from the group consisting of
2-amino-N8-[3-(2-aminoethyl)phenyl]-N4,N4-dipropyl-3H-1-benzazepine-4,8-dicarboxamide,
2-amino-N4-isobutyl-N8-(m-tolyl)-N4-propyl-3H-1-benzazepine-4,8-dicarboxamide,
2-amino-N4-[3-(3-aminopropoxy)propyl]-N8-(m-tolyl)-N4-propyl-3H-1-benzazepine-4,8-dicarboxamide,
2-amino-N8-[3-(5-aminopentyl)phenyl]-N4,N4-dipropyl-3H-1-benzazepine-4,8-dicarboxamide,
2-amino-N8-[4-(5-aminopentyl)phenyl]-N4,N4-dipropyl-3H-1-benzazepine-4,8-dicarboxamide,
2-amino-N8-[3-(3-aminopropyl)phenyl]-N4,N4-dipropyl-3H-1-benzazepine-4,8-dicarboxamide,
2-amino-N4-[[4-(aminomethyl)phenyl]methyl]-N8-(m-tolyl)-N4-propyl-3H-1-benzazepine-4,8-dicarboxamide,
2-amino-N8-[4-(3-aminopropyl)phenyl]-N4,N4-dipropyl-3H-1-benzazepine-4,8-dicarboxamide,
2-amino-N8-[4-(3-aminopropyl)phenyl]-N4,N4-dipropyl-3H-1-benzazepine-4,8-dicarboxamide,
2-amino-N8-[3-(2-aminoethyl)-4-fluoro-phenyl]-N4,N4-dipropyl-3H-1-benzazepine-4,8-dicarboxamide,
2-amino-N8-[3-(2-aminoethyl)-5-chloro-phenyl]-N4,N4-dipropyl-3H-1-benzazepine-4,8-dicarboxamide,
2-amino-N4-butyl-N4-(2-hydroxyethyl)-N8-(m-tolyl)-3H-1-benzazepine-4,8-dicarboxamide,
2-amino-N8-[5-(2-aminoethoxy)-3-pyridyl]-N4,N4-dipropyl-3H-1-benzazepine-4,8-dicarboxamide,
benzyl-N-[[5-[[2-amino-4-(dipropylcarbamoyl)-3H-1-benzazepine-8-carbonyl]amino]-3-pyridyl]methyl]carbamate,
2-amino-N8-[5-[(E)-3-aminoprop-1-enyl]-3-pyridyl]-N4,N4-dipropyl-3H-1-benzazepine-4,8-dicarboxamide,
2-amino-N8-[5-(2-phenylethyl)-3-pyridyl]-N4,N4-dipropyl-3H-1-benzazepine-4,8-dicarboxamide,
2-amino-N8-[5-[2-(4-methoxyphenyl)ethyl]-3-pyridyl]-N4,N4-dipropyl-3H-1-benzazepine-4,8-dicarboxamide,
2-amino-N8-[5-[2-[4-(aminomethyl)phenyl]ethyl]-3-pyridyl]-N4,N4-dipropyl-3H-1-benzazepine-4,8-dicarboxamide,
2-amino-N8-[5-(5-aminopentyl)-3-pyridyl]-N4,N4-dipropyl-3H-1-benzazepine-4,8-dicarboxamide,
2-amino-N8-[5-[2-(3-methoxyphenyl)ethyl]-3-pyridyl]-N4,N4-dipropyl-3H-1-benzazepine-4,8-dicarboxamide,
2-amino-N8-[5-(6-aminohexyl)-3-pyridyl]-N4,N4-dipropyl-3H-1-benzazepine-4,8-dicarboxamide,
2-amino-N8-[6-(3-aminopropyl)-3-pyridyl]-N4,N4-dipropyl-3H-1-benzazepine-4,8-dicarboxamide,
2-amino-N8-[5-(4-aminobutyl)-3-pyridyl]-N4,N4-dipropyl-3H-1-benzazepine-4,8-dicarboxamide,
2-amino-N8-[6-(4-aminobutyl)-3-pyridyl]-N4,N4-dipropyl-3H-1-benzazepine-4,8-dicarboxamide,
2-amino-N8-[5-[(dimethylamino)methyl]-3-pyridyl]-N4,N4-dipropyl-3H-1-benzazepine-4,8-dicarboxamide,
2-amino-N4-(cyclopropylmethyl)-N8-(5-ethoxy-3-pyridyl)-N4-propyl-3H-1-benzazepine-4,8-dicarboxamide, and
2-amino-N8-[5-(2-aminoethyl)-3-pyridyl]-N4,N4-dipropyl-3H-1-benzazepine-4,8-dicarboxamide,
or a pharmaceutically acceptable salt thereof.

16. A compound selected from the group consisting of
2-amino-N4,N4-dipropyl-N8-(3-pyridyl)-3H-1-benzazepine-4,8-dicarboxamide,
2-amino-N4,N4-dipropyl-N8-pyrimidin-5-yl-3H-1-benzazepine-4,8-dicarboxamide,
2-amino-N8-(4-chlorophenyl)-N4,N4-dipropyl-3H-1-benzazepine-4,8-dicarboxamide,
2-amino-N8-(m-tolyl)-N4,N4-dipropyl-3H-1-benzazepine-4,8-dicarboxamide,
2-amino-N4,N4-dipropyl-N8-[3-(pyrrolidine-1-carbonyl)phenyl]-3H-1-benzazepine-4,8-dicarboxamide,
2-amino-N8-(6-methyl-3-pyridyl)-N4,N4-dipropyl-3H-1-benzazepine-4,8-dicarboxamide,
2-amino-N8-(3,5-dimethylphenyl)-N4,N4-dipropyl-3H-1-benzazepine-4,8-dicarboxamide,
2-amino-N4-(3-hydroxypropyl)-N8-(m-tolyl)-N4-propyl-3H-1-benzazepine-4,8-dicarboxamide,
2-amino-N4,N4-dipropyl-N8-(p-tolyl)-3H-1-benzazepine-4,8-dicarboxamide,
2-amino-N8-(3-ethylphenyl)-N4,N4-dipropyl-3H-1-benzazepine-4,8-dicarboxamide,
2-amino-N8-(3-methoxyphenyl)-N4,N4-dipropyl-3H-1-benzazepine-4,8-dicarboxamide,
2-amino-N8-(3-chlorophenyl)-N4,N4-dipropyl-3H-1-benzazepine-4,8-dicarboxamide,
2-amino-N8-[5-(aminomethyl)-3-pyridyl]-N4,N4-dipropyl-3H-1-benzazepine-4,8-dicarboxamide,
2-amino-N4,N4-dipropyl-N8-pyridazin-4-yl-3H-1-benzazepine-4,8-dicarboxamide,
2-amino-N8-(6-ethoxy-3-pyridyl)-N4,N4-dipropyl-3H-1-benzazepine-4,8-dicarboxamide,
2-amino-N8-(5-methoxy-3-pyridyl)-N4,N4-dipropyl-3H-1-benzazepine-4,8-dicarboxamide,
2-amino-N8-(5-ethoxy-3-pyridyl)-N4,N4-dipropyl-3H-1-benzazepine-4,8-dicarboxamide,
2-amino-N8-[3-[2-(2-aminoethoxy)ethoxymethyl]phenyl]-N4,N4-dipropyl-3H-1-benzazepine-4,8-dicarboxamide,
2-amino-N8-(m-tolyl)-N4-propyl-N4-(3,3,3-trifluoropropyl)-3H-1-benzazepine-4,8-dicarboxamide, and
2-amino-N4-(cyclopropylmethyl)-N8-(m-tolyl)-N4-propyl-3H-1-benzazepine-4,8-dicarboxamide,
or a pharmaceutically acceptable salt thereof.

17. A compound selected from the group consisting of
2-amino-N8-[3-(2-aminoethyl)phenyl]-N4,N4-dipropyl-3H-1-benzazepine-4,8-dicarboxamide,
2-amino-N4-isobutyl-N8-(m-tolyl)-N4-propyl-3H-1-benzazepine-4,8-dicarboxamide, 2-amino-N8-[3-(3-aminopropyl)phenyl]-N4,N4-dipropyl-3H-1-benzazepine-4,8-dicarboxamide,
benzyl-N-[[5-[[2-amino-4-(dipropylcarbamoyl)-3H-1-benzazepine-8-carbonyl]amino]-3-pyridyl]methyl]carbamate,
2-amino-N8-[5-(2-phenylethyl)-3-pyridyl]-N4,N4-dipropyl-3H-1-benzazepine-4,8-dicarboxamide, and
2-amino-N4-(cyclopropylmethyl)-N8-(5-ethoxy-3-pyridyl)-N4-propyl-3H-1-benzazepine-4,8-dicarboxamide,
or a pharmaceutically acceptable salt thereof.

18. A pharmaceutical composition comprising a compound according to any one of claim 1 or 14-17, or a pharmaceutically acceptable salt thereof, and a pharmaceutically acceptable carrier and/or adjuvant.

19. A process for the manufacture of a compound of formula I, or a pharmaceutically acceptable salt thereof, as defined in claim 1, which process comprises
a) coupling a compound of the formula II

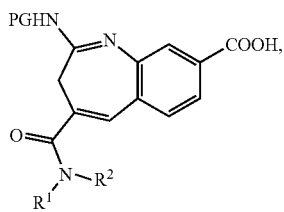

wherein $R^1$ and $R^2$ are as defined in claim 1 and PG is a protecting group, with a compound of the formula III

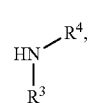

wherein $R^3$ and $R^4$ are as defined in claim 1, under basic conditions in the presence of a coupling agent and removing the protecting group PG under acidic conditions to obtain a compound of the formula I

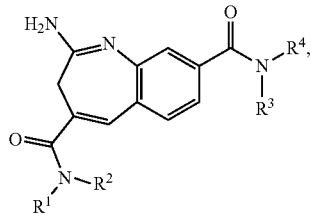

wherein $R^1$ to $R^4$ are as defined in claim 1, and, if desired, converting the compound obtained into a pharmaceutically acceptable salt.

* * * * *